US010369231B2

(12) United States Patent
Banfi et al.

(10) Patent No.: US 10,369,231 B2
(45) Date of Patent: Aug. 6, 2019

(54) MIR-204 AND MIR-211 AND USES THEREOF

(71) Applicant: FONDAZIONE TELETHON, Rome (IT)

(72) Inventors: Sandro Banfi, Naples (IT); Enrico Maria Surace, Naples (IT); Ivan Conte, Naples (IT); Marianthi Karali, Naples (IT); Elena Marrocco, Naples (IT)

(73) Assignee: FONDAZIONE TELETHON, Rome (IT)

( * ) Notice: Subject to any disclaimer, the term of this patent is extended or adjusted under 35 U.S.C. 154(b) by 0 days.

(21) Appl. No.: 14/774,586

(22) PCT Filed: Mar. 11, 2014

(86) PCT No.: PCT/EP2014/054755
§ 371 (c)(1),
(2) Date: Sep. 10, 2015

(87) PCT Pub. No.: WO2014/140051
PCT Pub. Date: Sep. 18, 2014

(65) Prior Publication Data
US 2016/0022836 A1 Jan. 28, 2016

(30) Foreign Application Priority Data
Mar. 11, 2013 (EP) .................... 13158603

(51) Int. Cl.
*A61K 48/00* (2006.01)
*C12N 15/11* (2006.01)
*C12N 15/86* (2006.01)
*C12N 15/113* (2010.01)
*A61K 31/7105* (2006.01)

(52) U.S. Cl.
CPC ........ *A61K 48/005* (2013.01); *A61K 31/7105* (2013.01); *C12N 15/113* (2013.01); *C12N 15/86* (2013.01); *C12N 2310/141* (2013.01); *C12N 2710/10032* (2013.01); *C12N 2710/10043* (2013.01)

(58) Field of Classification Search
CPC .. A61K 31/7105; A61K 48/00; A61K 48/005; C12N 15/11; C12N 15/113; C12N 15/86; C12N 15/8645; C12N 2310/141; C12N 2710/10043
See application file for complete search history.

(56) References Cited

U.S. PATENT DOCUMENTS 7,517,870 B2 * 4/2009 Auricchio ............... A61K 31/00
514/1.1
2010/0190841 A1 * 7/2010 Farrar ................. A61K 31/7105
514/44 R
2011/0229557 A1 * 9/2011 Feinstein ............. A61K 9/0048
424/450
2013/0131142 A1 * 5/2013 Libertine ............. A61K 9/0051
514/44 A
2015/0038549 A1 * 2/2015 Smith .................... C12N 15/111
514/44 A

FOREIGN PATENT DOCUMENTS

WO    WO 10/027838    *    3/2010

OTHER PUBLICATIONS

Grimson et al, Molecular Cell 27:91-105, 2007.*
Oshikawa et al, GenBank accession AB593053.1, Aug. 24, 2011.*
miRBase; http://www.mirbase.org/, last accessed Mar. 14, 2017.*
Klein et al, Arch. Opthalmol. 116:1082-1088, 1998.*
Georgiadis et al, Gene Therapy 17: 486-493, 2010.*
Maguire et al., "Age-dependent effects of RPE65 gene therapy for Leber's congenital amaurosis: a phase 1 dose-escalation trial", The Lancet, Lancet Limited. London, GB., vol. 374, No. 9701, Nov. 7, 2009, pp. 1597-1605 [retrieved on Nov. 5, 2009].
Conte et al., "Studio Del Ruolo Dei MicroRNA miR-204/211 Nella Funzione Oculare in Condizioni Fisiologiche e Patologiche," Nov. 22, 2012, p. C056, http://www.biomedia.net/cdAbstract/sigu2012/pdf/23115.pdf [retrieved on May 12, 2014].
Mussolino et al., "AAV-mediated photoreceptor transduction of the pig cone-enriched retina," Gene Therapy, vol. 18, No. 7, Mar. 17, 2011, pp. 637-645.
Adijanto et al., "Microphthalmia-associated Transcription Factor (MITF) Promotes Differentiation of Human Retinal Pigment Epithelium (RPE) by Regulating microRNAs-204/211 Expression," Journal of Biological Chemistry., vol. 287, No. 24, Jun. 8, 2012, pp. 20491-20503.
PCT International Search Report and the Written Opinion of the International Searching Authority dated May 19, 2014 for PCT/EP2014/054755, filed Mar. 11, 2014 (13 pages).
Bartel et al., 2009, "MicroRNAs: Target Recognition and Regulatory Functions" Cell 136: 215-233.
Mencia et, al., 2009, "Mutations in the seed region of human miR-96 are responsible for nonsyndromic progressive hearing loss" Nat Genet. 41(5):609-13.
Wang, 2014, "Composition of seed sequence is a major determinant of microRNA targeting patterns" Bioinformatics 30: 1377-1383.

(Continued)

Primary Examiner — Kevin K Hill
(74) Attorney, Agent, or Firm — Lucas & Mercanti, LLP

(57) ABSTRACT

The present invention relates to at least one agent capable of increasing the level of one or more miRNA in a cell or cells of a subject, said miRNA comprising the sequence UUC-CCUU, for use in the treatment and/or prevention of a retinal dystrophy, in particular characterized by photoreceptor degeneration, relative pharmaceutical compositions, nucleic acids, vectors and host cells.

Figure 1:
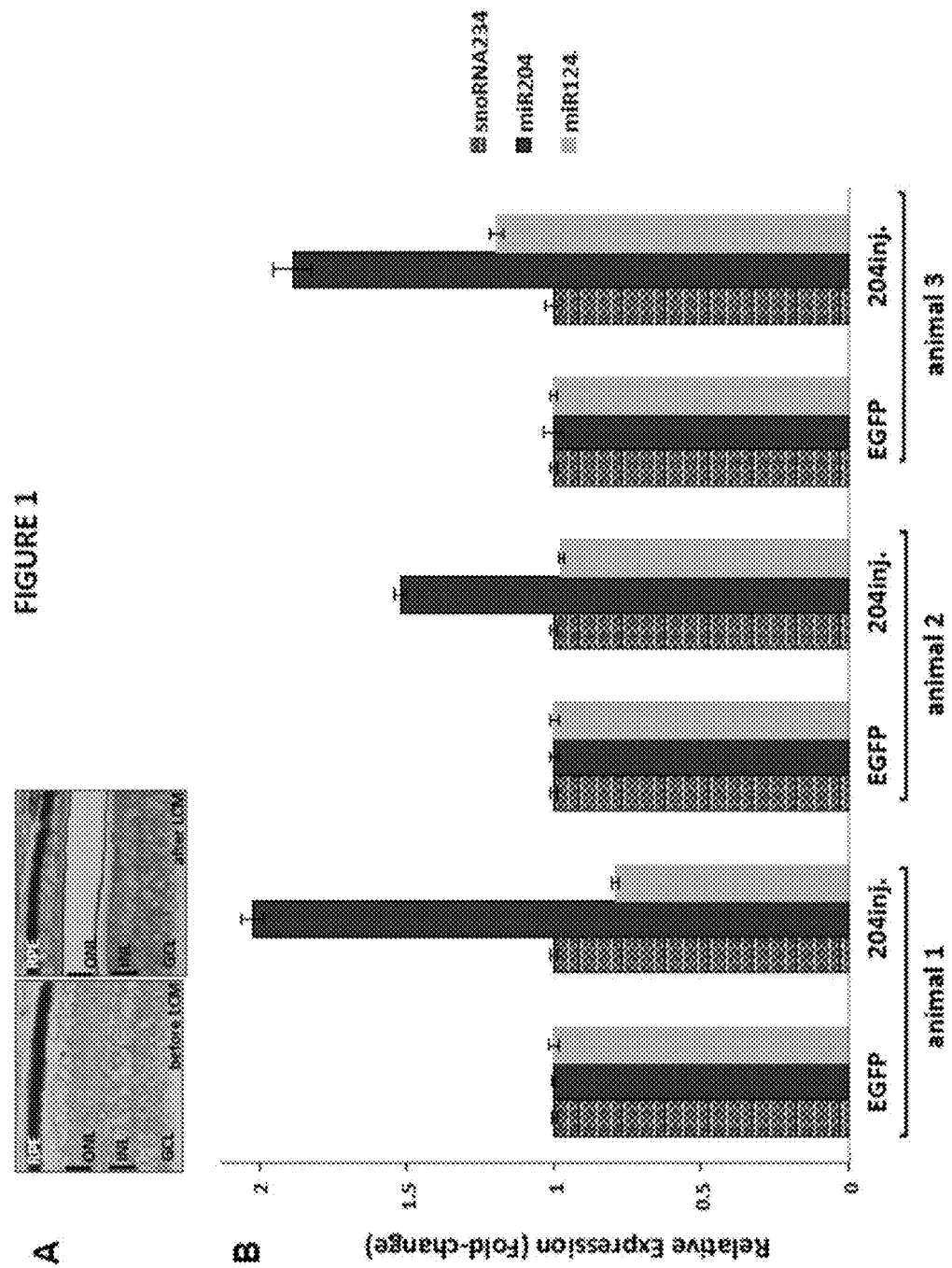

15 Claims, 20 Drawing Sheets
Specification includes a Sequence Listing.

(56) References Cited

OTHER PUBLICATIONS

Lewis et al, 2009, "An ENU-induced mutation of miR-96 associated with progressive hearing loss in mice" Nat Genet. 41(5): 614-61.
Hughes et al, 2011, "Mutation Altering the miR-184 Seed Region Causes Familial Keratoconus with Cataract" The American Journal of Human Genetics 89: 628-633.

* cited by examiner

MIR-204 AND MIR-211 AND USES THEREOF

CROSS-REFERENCE TO RELATED APPLICATIONS

The present application is a 371 of PCT/EP2014/054755, filed Mar. 11, 2014, which claims the benefit of European Patent Application No. 13 158 603.4 filed Mar. 11, 2013.

TECHNICAL FIELD

The present invention relates to at least one agent capable of increasing the level of one or more miRNA in a cell or cells of a subject, said miRNA comprising the sequence UUCCCUU, for use in the treatment and/or prevention of a retinal dystrophy, in particular characterized by photoreceptor degeneration, relative pharmaceutical compositions, nucleic acids, vectors and host cells.

BACKGROUND OF THE INVENTION

MicroRNAs (miRNAs) are post-transcriptional regulators of gene expression that are emerging as key players in the control of fundamental biological processes in both physiological and pathological conditions. Accumulating evidence suggests that miRNAs may control specific functional pathways by targeting gene networks of functionally correlated genes. In humans, deregulation of miRNA expression caused by mutations in either the miRNA itself or its target gene has been correlated with a number of pathological conditions such as diabetes, neurodegenerative diseases, heart failure and hereditary deafness (1, 2), among others. Recently, miRNAs are also emerging as new targets of therapeutic interventions for a variety of diseases. A therapeutic role of miRNAs has already been described in a number of cancer models (3, 4), in heart diseases (5, 6), in muscular dystrophy (7) and in liver disorders (8, 9). The use of a miR-122 inhibitor has already entered the clinic, where it is in phase I trials with the goal of treating hepatitis C infection (10). Therefore, the therapeutic use of miRNAs represents a promising field of research in modern medicine, although its extensive application requires an adequate understanding of the gene expression changes controlled by miRNAs.

Figure 20:
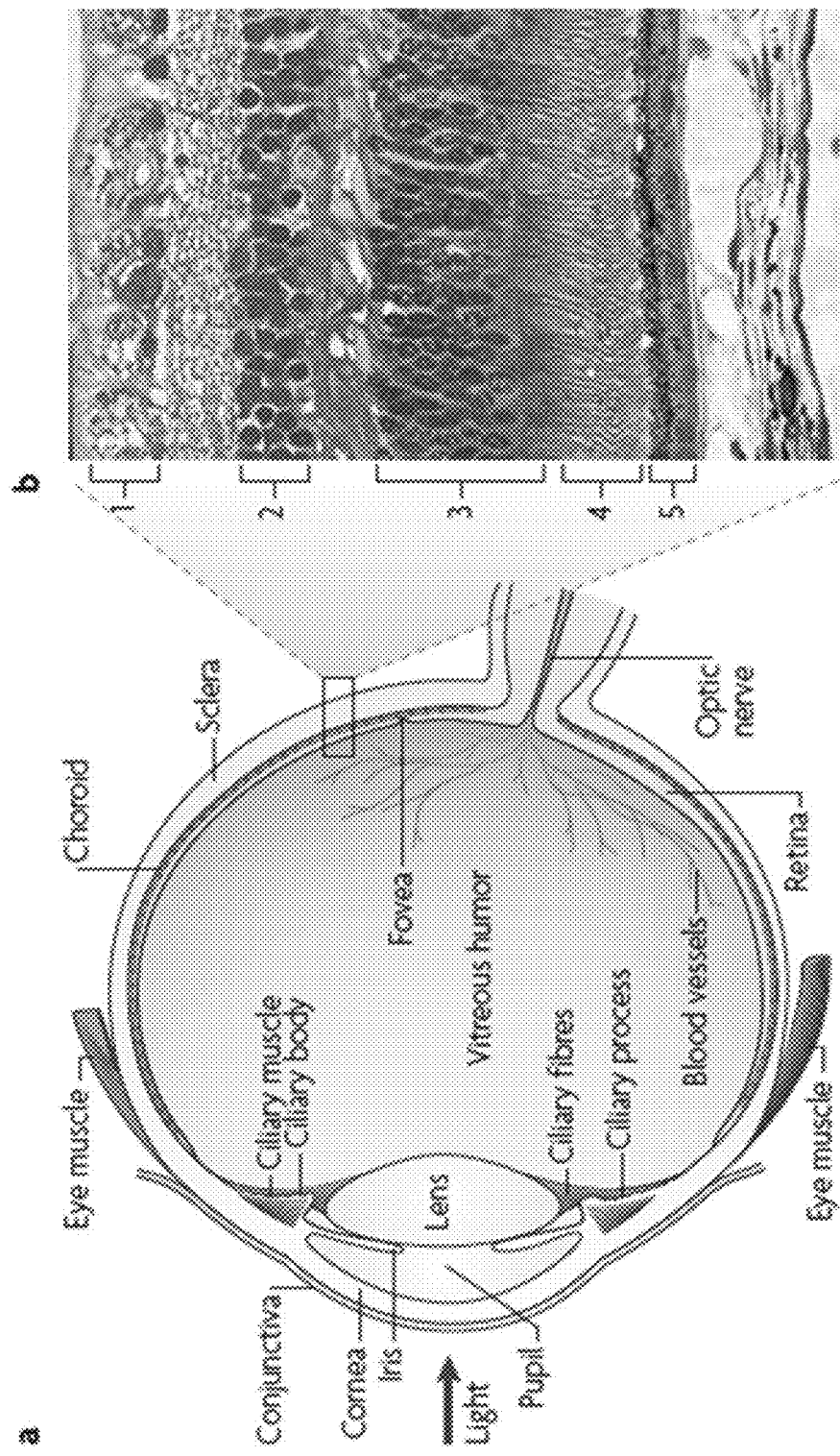

The retina is a layered structure composed of six neuronal and one glial cell type, which are organised in three cellular layers: the ganglion cell layer, comprising retinal ganglion (RGC) and displaced amacrine cells, the inner nuclear layer (INL), which contains bipolar, horizontal and amacrine interneurons and Müller glial cells, and the outer nuclear layer (ONL), where rod and cone photoreceptors are located. The retina is immediately adjacent to the retinal pigment epithelium (RPE), a pigmented cell layer that nourishes retinal visual cells, and is firmly attached to the underlying choroid and overlying retinal visual cells (FIG. 20).

Inherited retinal dystrophies (IRDs) represent one of the most frequent causes of genetic blindness in the western world. The primary condition that underlies this group of diseases is the degeneration of photoreceptors, i.e., the cells that convert the light information into chemical and electrical signals that are then transmitted to the brain through the visual circuits. There are two types of photoreceptor cells in the human retina: rods and cones. Rods represent about 95% of photoreceptor cells in the human retina and are responsible for sensing contrast, brightness and motion, whereas fine resolution, spatial resolution and color vision are perceived by cones.

IRDs can be subdivided into different groups of diseases, namely Retinitis Pigmentosa (RP), Leber Congenital Amaurosis (LCA), cone-rod dystrophies and cone dystrophies.

RP is the most frequent form of inherited retinal dystrophy with an approximate frequency of about 1 in 4,000 individuals (11). At its clinical onset, RP is characterized by night blindness and progressive degeneration of photoreceptors accompanied by bone spicule-like pigmentary deposits and a reduced or absent electroretinogram (ERG). RP can be either isolated or syndromic, i.e., associated with extraocular manifestations such as in Usher syndrome or in Bardet-Biedle syndrome. From a genetic point of view, RP is highly heterogeneous, with autosomal dominant, autosomal recessive and X-linked patterns of inheritance. A significant percentage of RP patients, however, are apparently sporadic. To date, around 50 causative genes/loci have been found to be responsible for non-syndromic forms of RP and over 25 for syndromic RPs (RETnet web site: http://www.sph.uth.tmc.edu/RetNet/).

LCA has a prevalence of about 2-3 in 100,000 individuals and is characterized by a severe visual impairment that starts in the first months/years of life (12). LCA has retinal, ocular as well as extraocular features, and occasionally systemic associations. LCA is inherited as an autosomal recessive trait in the large majority of patients, while autosomal dominant inheritance has been described only in a limited number of cases. LCA is genetically heterogeneous and, to date, mutations have been identified in 15 different genes: GUCY2D (locus name: LCA1), RPE65 (LCA2), SPATA7 (LCA3), AIPL1 (LCA4), LCA5 (LCA5), RPGRIP1 (LCA6), CRX (LCA7), CRB1 (LCA8), CEP290 (LCA10), IMPDH1 (LCA11), RD3 (LCA12), NMNAT1 (LCA9), LRAT (LCA14), TULP1 (LCA15), and RDH12 (LCA13). The diagnosis of LCA is established by clinical findings. Molecular genetic testing is clinically available for the 15 genes currently known to be associated with LCA. Collectively, mutations in these genes are estimated to account for approximately 40%-50% of all LCA cases, depending on the survey. Cone-rod dystrophies (CRDs) have a prevalence of 1/40,000 individuals and are characterized by retinal pigment deposits visible upon fundus examination, predominantly localized to the macular region. In contrast to typical RP, which is characterized by primary loss in rod photoreceptors, later followed by the secondary loss in cone photoreceptors, CRDs reflect the opposite sequence of events. CRD is characterized by a primary cone involvement, or, sometimes, by concomitant loss of both cones and rods that explains the predominant symptoms of CRDs: decreased visual acuity, color vision defects, photo-aversion and decreased sensitivity in the central visual field, later followed by progressive loss in peripheral vision and night blindness (13). Mutations in at least 20 different genes have been associated with CRD (RETnet web site: http://www.sph.uth.tmc.edu/RetNet/).

Cone dystrophies (CD) are conditions in which cone photoreceptors display a selective dysfunction that does not extend to rods. They are characterized by visual deficit, abnormalities of color vision, visual field loss, and a variable degree of nystagmus and photophobia. In CDs, cone function is absent or severely impaired on electroretinography (ERG) and psychophysical testing (14). Similar to the other forms of inherited retinal dystrophies, CDs are heterogeneous conditions that can be caused by mutations in at least 10 different genes (RETnet web site: http://www.sph.uth.tmc.edu/RetNet/).

As also mentioned above, IRDs are due to the degeneration and subsequent death of photoreceptor cells, primarily rods in the case of RP and LCA and primarily cones in the case of CRDs and CDs. Of interest, in RP and in most forms of LCA, rod degeneration is followed by a secondary degeneration of cones. The vast majority of genes responsible for IRDs are expressed predominantly in photoreceptors (either rods or cones). Some IRD genes are prevalently expressed in the retinal pigment epithelium. However, also in the latter case, the main consequence that derives from the dysfunction of these genes is a damage of photoreceptor function, which then translate into photoreceptor degeneration and death. For most forms of the above mentioned diseases an effective therapy is currently unavailable.

The authors are currently investigating the possible use of miRNAs as therapeutic tools in inherited retinal dystrophies. The authors have recently studied the expression pattern of miRNAs during the main stages of mammalian eye development and generated the most comprehensive up-to-date expression atlas of miRNAs in the mammalian eye (15, 16).

As a result, the authors identified a subset of miRNAs displaying significant expression levels in the mammalian eye, and among those miR-204 and miR-211. The authors started a detailed functional characterization of the latter miRNAs, using mostly in vivo models. In particular, the authors previously demonstrated, by using gain- and loss-of-function approaches in the medaka fish [*Oryzias latipes* (ol)] model organism, that alteration of miR-204 activity has a significant impact on multiple aspects of eye differentiation and function. In particular, morpholino-mediated ablation of miR-204 expression resulted in an eye phenotype characterized by microphthalmia and altered dorso-ventral (D-V) patterning of the retina, which causes optic coloboma (17).

Interestingly, miR-204 and miR-211 are closely related paralogs in mammals that share the same seed-region sequence and the same set of predicted targets (TargetScan) (18). They only differ by one nucleotide in mouse and two nucleotides in human.

Recently, miR-204 and miR-211 have been suggested to exert a protective effect on both the integrity of the retinal pigment epithelium (RPE) as a barrier and on preventing its abnormal proliferation (23).

On that basis, it has been proposed that the delivery of these two miRNAs to the RPE may exert a beneficial role in ocular diseases caused by abnormalities in the differentiation and proliferation of the RPE, including vitreal retinopathy, macular degeneration and diabetic retinopathy.

The application WO2010027838 refers to methods of preventing or treating detrimental retinal epithelial cell proliferation, loss of retinal epithelial cell differentiation, age-related macular degeneration and/or proliferative vitreal retinopathy by administering miR-204, miR-211, or a mixture of miR-204 and miR-211.

The document WO2009137807 concerns methods and compositions for diagnosing and/or treating, among others, vascular diseases of the eye, specifically ocular or retinal/choroidal neovascular diseases, by administering an inhibitor of miR-211. The methods involve measuring the levels of one or multiple miRNAs in patient samples and using the test results to diagnose and/or predict an optimal treatment regimen for the patient. Use of miR-211 is claimed for increasing vascularization.

Then, there is still the need for therapy that has a protective effect on the process of photoreceptor degeneration and death which are the primary conditions that underlie inherited retinal dystrophies. In such diseases, abnormal RPE differentiation and proliferation do not play key pathogenic roles.

SUMMARY OF THE INVENTION

The present invention relates to the use of miRNAs miR-204 and/or miR-211 to protect the retina from neuronal degeneration. The authors of the present invention found that the intraretinal administration of miR-204 and/or of miR-211, particularly in photoreceptor cells, exerts a beneficial effect in photoreceptor degeneration, and particularly in IRDs, including retinitis pigmentosa (both isolated and syndromic forms), Leber congenital amaurosis, cone-rod dystrophies and cone dystrophies. Notably, this demonstrates the therapeutic effect obtained by the administration of individual miRNAs in photoreceptors in vivo.

miRNAs are complementary to a part or fragment of one or more mRNAs. Moreover, miRNAs do not require absolute sequence complementarity to bind a mRNA, enabling them to regulate a wide range of target transcripts. miRNAs typically bind to target sequences with gaps between matched nucleotides. As used herein, the term "absolute sequence complementarity" is meant to describe a requirement that each nucleotide pair along the length of two sequences, e.g. a miRNA and a target gene or transcript, bind without gaps. The term "complementary" is meant to describe two sequences in which at least about 50% of the nucleotides bind from one sequence to the other sequence in trans.

miRNAs are frequently complementary to the 3' UTR of the mRNA transcript, however, miRNAs of the invention may bind any region of a target mRNA. Alternatively, or in addition, miRNAs target methylation genomic sites which correspond to genes encoding targeted mRNAs. The methylation state of genomic DNA in part determines the accessibility of that DNA to transcription factors. As such, DNA methylation and de-methylation regulate gene silencing and expression, respectively.

miRNAs of the invention include the sequences in Table 1 (SEQ ID NOs. 1-5) and to homologs and analogs thereof, to miRNA precursor molecules, and to DNA molecules encoding said miRNAs.

TABLE 1

| Mouse miR204 | SEQ ID NO: 1 and SEQ ID NO: 2 |
| Human miR204 | SEQ ID NO: 3 |
| Mouse miR211 | SEQ ID NO: 4 |
| miR211 | SEQ ID NO: 5 |

There are two versions of the mature sequence of mouse miR-204: 5'-UUCCCUUUGUC AUCCUAUGCCU-3' (SEQ ID NO: 1; miRBase Accession No. MIMAT0000237) and 5'-UUCCCUUUGUCAUCCUAUGCCUG-3' (SEQ ID NO: 2; GenBank Accession No. AJ560745) Based on the observation of a closely run doublet, both may exist in mice. The human mature miR-204 has the sequence 5'-UUC-CCUUUGUCAUCCUAUGCCU-3' (SEQ ID NO: 3; miRBase Accession No. MIMAT0000265). The sequence of mature mouse miRNA-211 is 5'-UUCCCUUUGUCAUC-CUUUGCCU-3'; SEQ ID NO: 4 (miRBase Accession No. MIMAT0000668). The human mature miR-211 has the sequence 5'-UUCCCUUUGUC AUCCUUCGCCU-3' (SEQ ID NO: 5; miRBase Accession No. MIMAT0000268).

Preferably the identity of a homolog to a sequence of SEQ ID NOs 1-5 may be at least 90%, more preferably at least 95% identical.

It is therefore an object of the present invention at least one agent capable of increasing the level of one or more miRNA in a cell or cells of a subject, said miRNA comprising the sequence UUCCCUU, for use in the treatment and/or prevention of a retinal dystrophy.

The sequence UUCCCUU is a seed sequence. The seed region forms a tight duplex with the target mRNA. Most miRNAs imperfectly base-pair with the 3' untranslated region (UTR) of target mRNAs, and the 5' proximal "seed" region of miRNAs provides most of the pairing specificity. Without being bound to any theory, it is believed that the first nine miRNA nucleotides (encompassing the seed sequence) provide greater specificity whereas the miRNA ribonucleotides 3' of this region allow for lower sequence specificity and thus tolerate a higher degree of mismatched base pairing, with positions 2-7 being the most important.

In the present invention, preferably the agent is selected from the group consisting of: a miRNA, a miRNA precursor, a mature miRNA, a miRNA mimetic or a mixture of miRNA mimetics, a RNA or DNA molecule encoding for said miRNA, for said miRNA precursor, for said mature miRNA, for said miRNA mimetic or mixture of miRNA mimetics, or any combination thereof.

Still preferably said agent comprises the sequence UUCCCUU or codifies for a nucleotide sequence comprising the sequence UUCCCUU.

Yet preferably the at least one miRNA comprising the sequence UUCCCUU is the mature sequence of miR-204 or the mature sequence of miR-211.

It should be noted that mature miRNAs may usually have a length of about 19-24 nucleotides (and any range in between), particularly 21, 22 or 23 nucleotides. The miRNAs, however, may be also provided as a precursor which may have a length of about 70 to about 100 nucleotides (pre-miRNA). It should be noted that the precursor may be produced by processing of a primary transcript which may have a length of greater than about 100 nucleotides (pri-miRNA). The miRNA as such may usually be a single-stranded molecule, while the miRNA-precursor may usually be in the form of an at least partially self-complementary molecule capable of forming double-stranded portions, e.g. stem- and loop-structures. DNA molecules encoding the miRNA, pre-miRNA and pri-miRNA molecules are also be encompassed by the invention. The nucleic acids may be selected from RNA, DNA or nucleic acid analog molecules, such as sugar- or backbone-modified ribonucleotides or deoxyribonucleotides. It should be noted, however, that other nucleic analogs, such as peptide nucleic acids (PNA) or locked nucleic acids (LNA), may also be suitable.

The nucleic acid molecules of the invention may be obtained by chemical synthesis methods or by recombinant methods, e.g. by enzymatic transcription from synthetic DNA-templates or from DNA-plasmids isolated from recombinant organisms. Typically phage RNA-polymerases are used for transcription, such as T7, T3 or SP6 RNA-polymerases.

The invention may also relate to a recombinant expression vector comprising a recombinant nucleic acid operatively linked to an expression control sequence, wherein expression, i.e. transcription and. optionally further processing results in a miRNA-molecule or miRNA precursor (pri- or pre-miRNA) molecule as described above. The vector may be an expression vector suitable for nucleic acid expression in eukaryotic, more particularly mammalian cells. The recombinant nucleic acid contained in said vector may be a sequence which results in the transcription of the miRNA-molecule as such, a precursor or a primary transcript thereof, which may be further processed to give the miRNA-molecule.

Still preferably said agent comprises the mature sequence of miR-204 or the mature sequence of miR-211.

In a preferred embodiment said agent is provided within a delivery vehicle, optionally wherein the delivery vehicle is selected from a viral vector, microspheres, liposomes, colloidal gold particles, lipopolysaccharides, polypeptides, polysaccharides, or pegylation of viral vehicles.

In a preferred embodiment, the retinal dystrophy is characterized by photoreceptor degeneration. Preferably, the retinal dystrophy is an inherited retinal dystrophy. Still preferably the inherited retinal degeneration is selected from the group consisting of: Retinitis Pigmentosa (RP), Leber Congenital Amaurosis (LCA), cone-rod dystrophies and cone dystrophies.

It is a further object of the invention a pharmaceutical composition comprising at least one agent capable of increasing the level of one or more miRNA, said miRNA comprising the sequence UUCCCUU as defined above, and pharmaceutically acceptable excipients and/or diluents for use in the treatment and/or prevention of a retinal dystrophy.

Preferably said agent is selected from the group consisting of: a miRNA, a miRNA precursor, a mature miRNA, a miRNA mimetic or a mixture of miRNA mimetics, a RNA or DNA molecule encoding for said miRNA, for said miRNA precursor, for said mature miRNA, for said miRNA mimetic or mixture of miRNA mimetics, or any combination thereof, preferably said agent comprises the sequence UUCCCUU or codifies for a nucleotide sequence comprising the sequence UUCCCUU, still preferably said agent comprises the mature sequence of miR-204 or the mature sequence of miR-211.

It is a further object of the invention a nucleic acid sequence coding for the agent as defined above for use in the treatment and/or prevention of a retinal dystrophy.

It is a further object of the invention a recombinant expression vector comprising a coding sequence for the agent as defined above under the control of a suitable promoter for use in the treatment and/or prevention of a retinal dystrophy.

Preferably the suitable promoter is the Rhodopsin promoter sequence.

Still preferably the recombinant expression vector as defined above further comprises one or more wild-type form of a coding sequence responsible for the retinal dystrophy under the control of a suitable promoter. Preferably the suitable promoter is the Rhodopsin promoter sequence or a promoter driving the expression in the RPE.

Preferably, one or more wild-type form of the coding sequence responsible for the retinal dystrophy is selected from the group consisting of: SEQ ID NO: 23 to SEQ ID NO: 414.

Any combination of SEQ ID NO: 23 to SEQ ID NO:414 is suitable for the present invention. Preferably, wild-type form of the coding sequence is the coding sequence of AIPL1.

In a preferred embodiment the recombinant expression vector as defined above is an AAV derivative.

It is a further object of the invention a host cell transformed by the recombinant expression vector as defined above.

It is a further object of the invention a pharmaceutical composition comprising the nucleic acid sequence as defined above or the recombinant expression vector as defined above or the host cell as defined above and pharmaceutically acceptable excipients and/or diluents for use in the treatment and/or prevention of a retinal dystrophy.

Preferably, the pharmaceutical composition further comprises one or more wild-type form of a coding sequence responsible for the retinal dystrophy under the control of a suitable promoter. Preferably the wild-type form of the coding sequence responsible for the retinal dystrophy is inserted in a further separated or independent recombinant expression vector.

Preferably in the pharmaceutical composition defined above, one or more wild-type form of the coding sequence responsible for the retinal dystrophy is selected from the group consisting of: SEQ ID NO: 23 to SEQ ID NO: 414.

Preferably, wild-type form of the coding sequence is the coding sequence of AIPL1.

Preferably the pharmaceutical composition as defined above for intraocular administration.

It is a further object of the invention a method for the treatment and/or prevention of a retinal dystrophy in a subject comprising administering the agent as defined above or the pharmaceutical composition as defined above or the nucleic acid as defined above or the recombinant expression vector as defined above or the host cell as defined above to said subject. Preferably, the retinal dystrophy is characterized by photoreceptor degeneration.

It is contemplated that the therapeutic methods of the present invention may be used in combination with another method of treating a retinal dystrophy. Additional therapeutic agents may include a neuroprotective molecule such as: growth factors such as ciliary neurotrophic factor (CNTF), glial-derived neurotrophic factor (GDNF), cardiotrophin-1, brain-derived neurotrophic factor (BDNF) and basic fibroblast growth factor (bFGF) or the rod-derived cone viability factors such as RdCVF and RdCVF2.

In the present invention the wild-type form of the coding sequence responsible for the retinal dystrophy, in particular characterized by photoreceptor degeneration, in particular inherited retinal dystrophy are selected from the group consisting of the following genes: ABHD12, ACBD5, ADAM9, ADAMTS18, AIPL1, ARL2BP, ARL6, BBIP1, BBS1, BBS10, BBS12, BBS2, BBS4, BBS5, BBS7, BBS9, C21orf2, C2orf71, C8orf37, CACNA2D4, CDH23, CDH3, CDHR1, CEP290, CERKL, CIB2, CLRN1, CNGA1, CNGB1, CNNM4, CRB1, DFNB31, DHDDS, EMC1, EYS, FAM161A, GPR125, GPR98, GUCY2D, HARS, IDH3B, IMPG2, IQCB1, KCNJ13, KCNV2, KIAA1549, LCA5, LRAT, MAK, MERTK, MKKS, MKS1, MVK, MYO7A, NEK2, NMNAT1, OFD1, OTX2, PCDH15, PDE6A, PDE6B, PDE6C, PDE6G, PRCD, PROM1, RAB28, RAX2, RBP3, RD3, RDH12, RGR, RLBP1, RP2, RPE65, RPGR, RPGRIP1, SAG, SDCCAG8, SPATA7, TRIM32, TTC8, TTPA, TULP1, UNC119, USH1A, USH1C, USH1G, USH2A, ZNF513. Relative coding sequences are the sequences consisting of SEQ ID NO: 23 to SEQ ID NO: 414.

Inherited retinal dystrophies (IRDs) represent one of the most frequent causes of genetic blindness in the western world. The primary condition that underlies this group of diseases is the degeneration of photoreceptors, i.e., the cells that convert the light information into chemical and electrical signals that are then transmitted to the brain through the visual circuits. IRDs can be subdivided into different groups of diseases, namely Retinitis Pigmentosa (RP), Leber Congenital Amaurosis (LCA), cone-rod dystrophies and cone dystrophies. The agent of the present invention treats and/or prevent one or more of such diseases.

In the present invention contemplated agents capable of increasing the level of one or more miRNA may include miRNA molecules, single or double-stranded RNA or DNA polynucleotides, peptide nucleic acids (PNAs), proteins, small molecules, ions, polymers, compounds, antibodies, intrabodies, antagomirs or any combination thereof. The agent may augment miRNA expression levels, activity, and/or function.

In some aspects, the agent capable of increasing the level of one or more miRNA may be an RNA- or DNA molecule, which may contain at least one modified nucleotide analog, i.e. a naturally occurring ribonucleotide or deoxyribonucleotide is substituted by a non-naturally occurring nucleotide. The modified nucleotide analog may be located for example at the 5'-end and/or the 3'-end of the nucleic acid molecule.

Nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase, such as uridines or cytidines modified at the 5-position, e.g. 5-(2-amino)propyl uridine, 5-bromo uridine; adenosines and guanostnes modified at the 8-position, e.g. 8-bromo guanosine; deaza nucleotides, e.g. 7-deaza-adenosine; O- and N-alkylated nucleotides, e.g. N6-methyl adenosine may be suitable. In sugar-modified ribonucleotides the 2'-OH-group is replaced by a group selected from H, OR, R, halo, SH, SR, NH 2, NHR, NR 2 or CN, wherein R is C1-C6 alkyl, alkenyl or alkynyl and halo is F, CI, Br or I. In preferred backbone-modified ribonucleotides the phosphoester group connecting to adjacent ribonucleotides is replaced by a modified group, e.g. of phosphothioate group. It should be noted that the above modifications may be combined.

In the present invention "miR mimics or mimetics" are small double-stranded RNA oligonucleotides, that can be chemically modified and that mimic endogenous miRNAs and enable miRNA functional analysis by up-regulation of miRNA activity. The mimic or mimetic sequence corresponds to the sequence of the miRNA mature sequence.

In the present invention photoreceptor degeneration is the progressive deterioration and ultimately death of photoreceptor cells.

Photoreceptor degeneration and death are the primary conditions that underlie inherited photoreceptor degeneration, in particular inherited photoreceptor degeneration as in inherited retinal dystrophies. In photoreceptor degeneration, abnormal RPE differentiation and proliferation do not play key pathogenic roles.

The agent of the present invention have a therapeutic activity in photoreceptor degeneration which is a distinct effect than the one on epithelial cell differentiation or proliferation.

In the present invention miR-204/211 means miR-204 and/or miR-211. Most miRNAs imperfectly base-pair with the 3' untranslated region (UTR) of target mRNAs, and the 5' proximal "seed" region of miRNAs provide most of the pairing specificity. Without being bound to any theory, it is believed that the first nine miRNA nucleotides (encompassing the seed sequence) provide greater specificity whereas the miRNA ribonucleotides 3' of this region allow for lower sequence specificity and thus tolerate a higher degree of mismatched base pairing, with positions 2-7 being the most important. Mimics or mimetic of miR-204, miR-211 may be produced by many techniques known in the art. The 2' hydroxyl group of the ribose sugars may be alkylated, such as by methylation, to increase the stability of the molecule. Also, the ribose sugars may be modified by replacement of the hydroxyl group at the 2' position with a hydrogen, thus generating a DNA backbone. Also, any uracil base of an RNA sequence may be replaced by thymine. These are only a few non-limiting examples of the possible modifications that may be performed by a skilled artisan.

In the present invention miR-204 and/or miR-211 may be delivered to the retina via the subretinal injection of AAV constructs. However, it is important to point out that the mature forms of miRNAs could also be administered to the retina as double stranded RNA oligonucleotides (microRNA mimics) whose delivery can be enhanced by conjugation with other molecular structures or encapsulation with carriers such as liposomes or nanoparticles (24). Moreover, both the miR-204/211 AAV constructs or miR-204/211 mimics can also be prepared in the form of injectable suspension, eye lotion or ophthalmic ointment that can be delivered to the retina with a non-invasive procedure.

The administration of oligonucleotides of the present invention may be carried out by known methods, wherein a nucleic acid is introduced into a desired target cell in vitro or in vivo. An aspect of the present invention comprises a nucleic acid construct comprised within a delivery vehicle. A delivery vehicle is an entity whereby a nucleotide sequence can be transported from at least one media to another. Delivery vehicles may be generally used for expression of the sequences encoded within the nucleic acid construct and/or for the intracellular delivery of the construct. It is within the scope of the present invention that the delivery vehicle may be a vehicle selected from the group of RNA based vehicles, DNA based vehicles/vectors, lipid based vehicles, virally based vehicles and cell based vehicles. Examples of such delivery vehicles include: biodegradable polymer microspheres, lipid based formulations such as liposome carriers, coating the construct onto colloidal gold particles, lipopolysaccharides, polypeptides, polysaccharides, pegylation of viral vehicles.

In one embodiment of the present invention may comprise a virus as a delivery vehicle, where the virus may be selected from: adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector. Such viral vectors are well known in the art.

Commonly used gene transfer techniques include calcium phosphate, DEAE-dextran, transfection, electroporation and microinjection and viral methods (30-34). Another technique for the introduction of DNA into cells is the use of cationic liposomes (35). Commercially available cationic lipid formulations are e.g. Tfx 50 (Promega) or Lipofectamin 2000 (Life Technologies).

The compositions of the present invention may be in form of a solution, e.g. an injectable solution, a cream, ointment, tablet, suspension or the like. The composition may be administered in any suitable way, e.g. by injection, particularly by intraocular injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly cationic liposomes.

An aspect of the present invention further encompasses pharmaceutical compositions comprising one or more miR-NAs or miRNA for administration to subjects in a biologically compatible form suitable for administration in vivo. The miRNAs of the invention may be provided within expression vectors as described above that are formulated in a suitable pharmaceutical composition.

By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result of increasing/decreasing the production of proteins. A therapeutically effective amount of a substance may vary according to factors such as the disease state/health, age, sex, and weight of the recipient, and the inherent ability of the particular polypeptide, nucleic acid coding therefore, or recombinant virus to elicit the desired response. Dosage regimen may be adjusted to provide the optimum therapeutic response. For example, several divided doses may be administered daily or at periodic intervals, and/or the dose may be proportionally reduced as indicated by the exigencies of the therapeutic situation. The amount of miRNA or miRNA modulator for administration will depend on the route of administration, time of administration and varied in accordance with individual subject responses. Suitable administration routes are intramuscular injections, subcutaneous injections, intravenous injections or intraperitoneal injections, oral and intranasal administration. In the case of IRD, injecting the miRNA- and/or miRNA modulator-based composition into the retina of the subject may be preferred. The composition of the invention may also be provided via implants, which can be used for slow release of the composition over time.

In the case of photoreceptor degeneration, such as in IRDs (in particular, Retinitis Pigmentosa (RP), Leber Congenital Amaurosis (LCA), cone-rod dystrophies and cone dystrophies), the miRNA- or miRNA modulator-based compositions of the invention may be administered topically to the eye in effective volumes of from about 5 microliters to about 75 microliters, for example from about 7 microliters to about 50 microliters, preferably from about 10 microliters to about 30 microliters. The miRNAs of the invention may be highly soluble in aqueous solutions. Topical instillation in the eye of miRNA in volumes greater than 75 microliters may result in loss of miRNA from the eye through spillage and drainage. Thus, it is preferred to administer a high concentration of miRNA (e.g., from 1 nM to 100 µM, with a preferred range between 10 and 1000 nM) by topical instillation to the eye in volumes of from about 5 microliters to about 75 microliters.

In one aspect, the parenteral administration route may be intraocular administration. Intraocular administration of the present miRNA-based composition can be accomplished by injection or direct (e.g., topical) administration to the eye, as long as the administration route allows the miRNA to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art (36-39).

The recombinant expression vector of the invention can be any suitable recombinant expression vector, and can be used to transform or transfect any suitable host. Suitable vectors include those designed for propagation and expansion or for expression or both, such as plasmids and viruses. The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell.

Replication systems can be derived, e.g., from ColE1, 2μ plasmid, λ, S V40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes. The recombinant expression vector can comprise a native or normative promoter operably linked to the nucleotide sequence encoding the miR 204, miR 211, and/or mimics thereof (including functional portions and functional variants thereof), or to the nucleotide sequence which is complementary to or which hybridizes to the nucleotide sequence encoding the RNA. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an S V40 promoter, an RSV promoter, and a promoter found in the long-terminal repeat of the murine stem cell virus. Preferred promoter is the Rhodopsin promoter.

The inventive recombinant expression vectors can be designed for either transient expression, for stable expression, or for both. Also, the recombinant expression vectors can be made for constitutive expression or for inducible expression.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α, E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell.

The terms "treat or treatment" and "prevent or prevention" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect, in this respect, the inventive methods can provide any amount of any level of treatment or prevention of a condition associated with miR 204 and/or miR 211, e.g. in a mammal. Furthermore, the treatment or prevention provided by the inventive method can include treatment or prevention of one or more conditions or symptoms of the disease being treated or prevented. Also, for purposes herein, "prevention" can encompass delaying the onset of the disease, or a symptom or condition thereof. An "effective amount" refers to a dose that is adequate to prevent or treat a disease or disorder characterized by photoreceptor degeneration in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the compound selected, method of administration, timing and frequency of administration as well as the existence, nature, and extent of any adverse side-effects that might accompany the administration of a particular compound and the desired physiological effect. It will be appreciated by one of skill in the art that various diseases or disorders could require prolonged treatment involving multiple administrations, perhaps using miR 204, miR 211 and/or mimics thereof in each or various rounds of administration. A miR and mimics thereof can be administered in a composition (e.g., pharmaceutical composition) that can comprise at least one excipient (e.g., a pharmaceutically acceptable excipient), as well as other therapeutic agents (e.g., other miRs and/or mimics thereof). The composition can be administered by any suitable route, including parenteral, topical, oral, or local administration.

The pharmaceutically acceptable excipient is preferably one that is chemically inert to the miR, and/or mimics thereof and one that has little or no side effects or toxicity under the conditions of use. Such pharmaceutically acceptable carriers include, but are not limited to, water, saline, Cremophor EL (Sigma Chemical Co., St. Louis, Mo.), propylene glycol, polyethylene glycol, alcohol, and combinations thereof. The choice of carrier will be determined in part by the particular miR, and/or mimics thereof as well as by the particular method used to administer the composition. Accordingly, there is a wide variety of suitable formulations of the composition.

The pharmaceutical composition in the context of an embodiment of the invention can be, for example, in the form of a pill, capsule, or tablet, each containing a predetermined amount of one or more of the active compounds and preferably coated for ease of swallowing, in the form of a powder or granules, or in the form of a solution or suspension. For oral administration, fine powders or granules may contain diluting, dispersing, and or surface active agents and may be present, for example, in water or in a syrup, in capsules or sachets in the dry state, or in a nonaqueous solution or suspension wherein suspending agents may be included, or in tablets wherein binders and lubricants may be included. Components such as sweeteners, flavoring agents, preservatives (e.g., antimicrobial preservatives), suspending agents, thickening agents, and/or emulsifying agents also may be present in the pharmaceutical composition. When administered in the form of a liquid solution or suspension, the formulation can contain one or more of the active compounds and purified water. Optional components in the liquid solution or suspension include suitable preservatives (e.g., antimicrobial preservatives), buffering agents, solvents, and mixtures thereof. A component of the formulation may serve more than one function.

Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition. Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition. The following formulations for oral, aerosol, parenteral (e.g., subcutaneous, intravenous, intraarterial, intramuscular, intradermal, interperitoneal, and intrathecal), and rectal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art. The miRs and mimics thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Formulations suitable for parenteral administration include aqueous and nonaqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The miR and mimics thereof may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations may include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets. The miRs and mimics thereof may be administered as an injectable formulation. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986). Topical formulations, including those that are useful for transdermal drug release, are well known to those of skill in the art and are suitable in the context of embodiments of the invention for application to skin.

The concentration of a compound of embodiments of the invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected. Methods for preparing administrable (e.g., parenterally administrable) compositions are known or apparent to those skilled in the art and are described in more detail in, for example, Remington's Pharmaceutical Science (17th ed., Mack Publishing Company, Easton, Pa., 1985). In addition to the aforedescribed pharmaceutical compositions, the miRs and mimics thereof can be formulated as inclusion complexes, such as cyclodextrin inclusion complexes, or liposomes. Liposomes can serve to target the miRs and mimics thereof to a particular tissue. Liposomes also can be used to increase the half-life of the miRs and mimics thereof. Many methods are available for preparing liposomes, as described in, for example, Szoka et al., Ann. Rev. Biophys.

Bioeng., 9:467 (1980) and U.S. Pat. Nos. 4,235,871, 4,501,728, 4,837,028, and 5,019,369.

When the agent of the invention such as a miR, a miR mimics thereof are administered with one or more additional therapeutic agents, one or more additional therapeutic agents can be coadministered to the mammal. By "coadministering" is meant administering one or more additional therapeutic agents and the miR and/or mimics thereof sufficiently close in time such that the miR and/or mimics thereof can enhance the effect of one or more additional therapeutic agents. In this regard, the miR and/or mimics thereof can be administered first and the one or more additional therapeutic agents can be administered second, or vice versa. Alternatively, the miR and/or mimics thereof and the one or more additional therapeutic agents can be administered simultaneously. The additional therapeutic agent may be a recombinant expression vector comprising the wild type form of the coding sequence responsible for the inherited retinal dystrophy under the control of an appropriate promoter. Additional therapeutic agents may include a neuroprotective molecule such as: growth factors such as ciliary neurotrophic factor (CNTF), glial-derived neurotrophic factor (GDNF), cardiotrophin-1, brain-derived neurotrophic factor (BDNF) and basic fibroblast growth factor (bFGF) or the rod-derived cone viability factors such as RdCVF and RdCVF2.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The invention will be now illustrated by means of non-limiting examples referring to the following figures.

FIG. 1. miR-204 expression levels in the ONL of eyes injected with AAV.CMV.premiR204. (A) Retinal sections before (left panel) and after (right panel) laser capture microdissection (LCM). Microdissected-samples containing the outer nuclear layer (ONL) were pooled together for RNA extraction. (B) miRNA expression profile analysis on the LCM-collected ONL of three animals injected subretinally with AAV at 6-weeks of age and sacrificed 3 weeks later. Expression levels were determined by RT-qPCR on total RNA extracted from retinas injected with AAV.CMV.premiR204 (204inj) and AAV.CMV.EGFP (EGFP). Expression levels of individual miRNAs were normalized against the levels of sno234, which served as a control. Subretinal administration of the AAV.CMV.premiR204 vector conferred an 1.5- to 2-fold increase of miR-204 compared to the endogenous levels. The levels of miR-124 did not vary significantly. Abbreviations: GCL, ganglion cell layer; INL, inner nuclear layer; ONL, outer nuclear layer; RPE, Retinal Pigment Epithelium.

Figure 2:
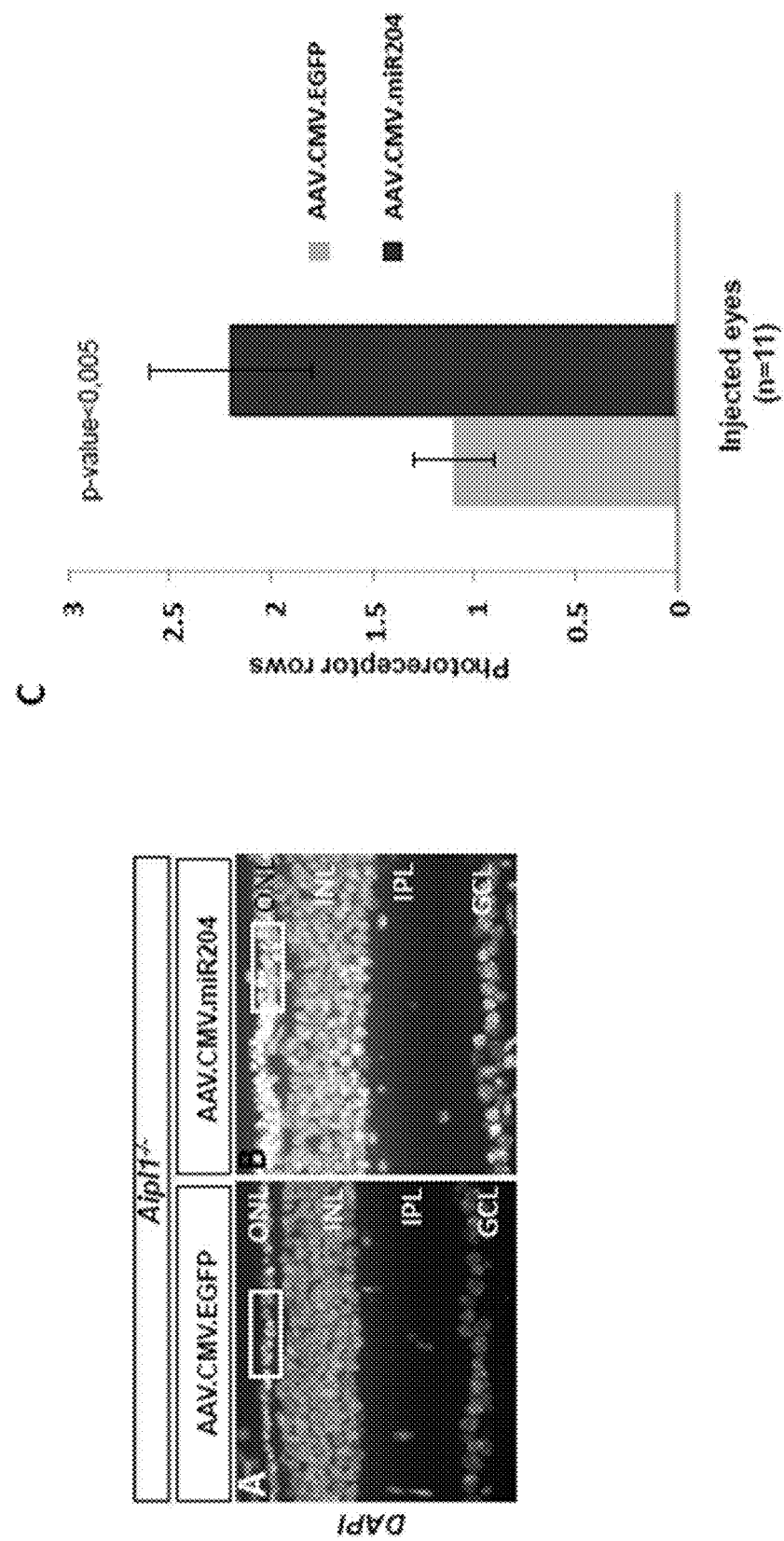

FIG. 2. Histological analysis of retinas from Aipl1$^{-/-}$ mice following subretinal delivery of the AAV.CMV.EGFP and AAV.CMV.premiR204 vectors at P4. (A) DAPI staining of retinal sections at P21. Only one row of nuclei is present in the ONL of Aipl1$^{-/-}$ eyes injected with the AAV.CMV.EGFP control vector (box in A). Instead, there is an increase in the number of rows and density of nuclei at the ONL of the contralateral eye injected with the AAV.CMV.premiR204 vector (box in B). The other retinal layers (INL, IPL and GCL) appear to be unaffected. (C) Plot showing the average number of photoreceptor nuclei rows in treated eyes (n=11) compared to contralateral eyes, injected with the control vector. Abbreviations: ONL, outer nuclear layer; INL, inner nuclear layer; IPL, inner plexiform layer; GCL, ganglion cell layer.

Figure 3:
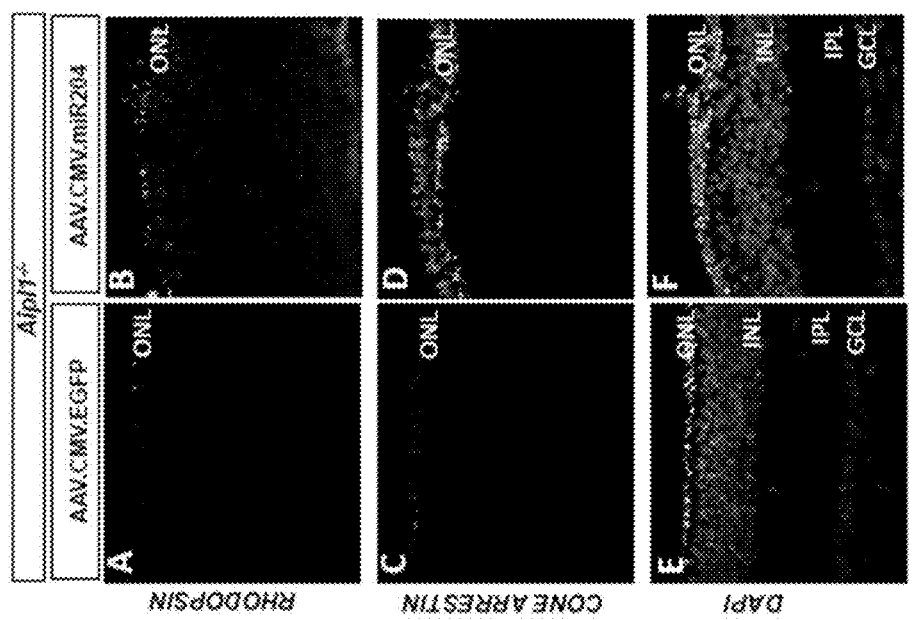

FIG. 3. Immunohistological analysis of retinas from Aipl1$^{-/-}$ mice following subretinal delivery of the AAV.CMV.EGFP and AAV.CMV.premiR204 vectors at postnatal day (P) 4. Confocal microscopy images of rod marker rhodopsin (A, B) and cone marker cone arrestin (C, D) immunolabelling on retinal sections at P21. An increased staining for rod and cone photoreceptor markers is observed at the ONL of eyes injected with the AAV.CMV.premiR204 vector compared to the contralateral eyes injected with the EGFP control vector. DAPI-staining of these sections is shown in E and F. Abbreviations: ONL, outer nuclear layer; INL, inner nuclear layer; IPL, inner plexiform layer; GCL, ganglion cell layer.

Figure 4:
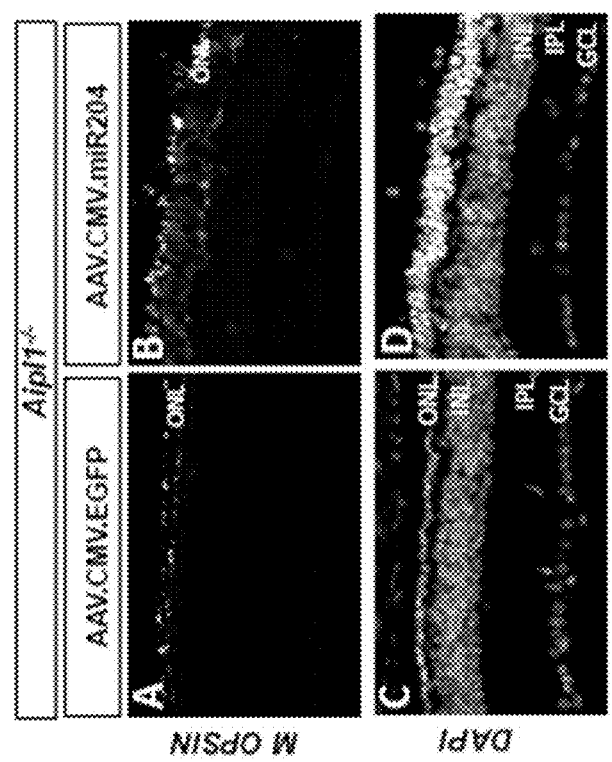

FIG. 4. M Opsin immunolabelling of retinas from Aipl1$^{-/-}$ mice following subretinal delivery of the AAV.CMV.EGFP and AAV.CMV.premiR204 vectors at postnatal day (P) 4. Confocal microscopy images of cone marker M-Opsin (A, B) immunolabelling on retinal sections at P21. An increased staining for M Opsin is observed at the ONL of eyes injected with the AAV.CMV.premiR204 vector compared to the contralateral eyes injected with the EGFP control vector. DAPI-staining of these sections is shown in C and D. Abbreviations: ONL, outer nuclear layer; INL, inner nuclear layer; IPL, inner plexiform layer; GCL, ganglion cell layer.

Figure 5:
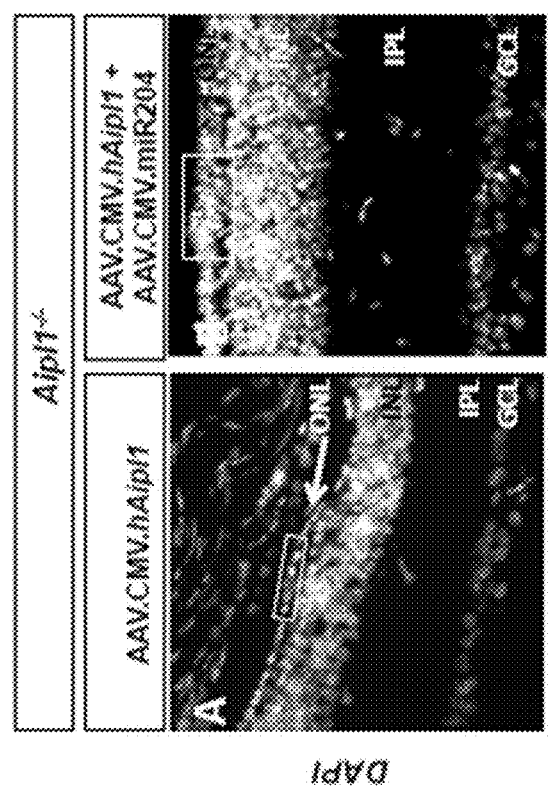

FIG. 5. Partial preservation of retinal structure in Aipl1$^{-/-}$ mice following AAV-mediated combined delivery of miR-204 and of the hAIPL1 gene. DAPI-staining of retinal sections at P30 showing partial preservation of retinal thickness (number of photoreceptor cell nuclei) in Aipl1$^{-/-}$ mice following simultaneous subretinal injection at P4 of two distinct vectors: AAV.CMV.premiR204 in combination with AAV.CMV.hAIPL1 (B), compared to contralateral eyes injected with the AAV.CMV.hAIPL1 alone (A).

Figure 6:
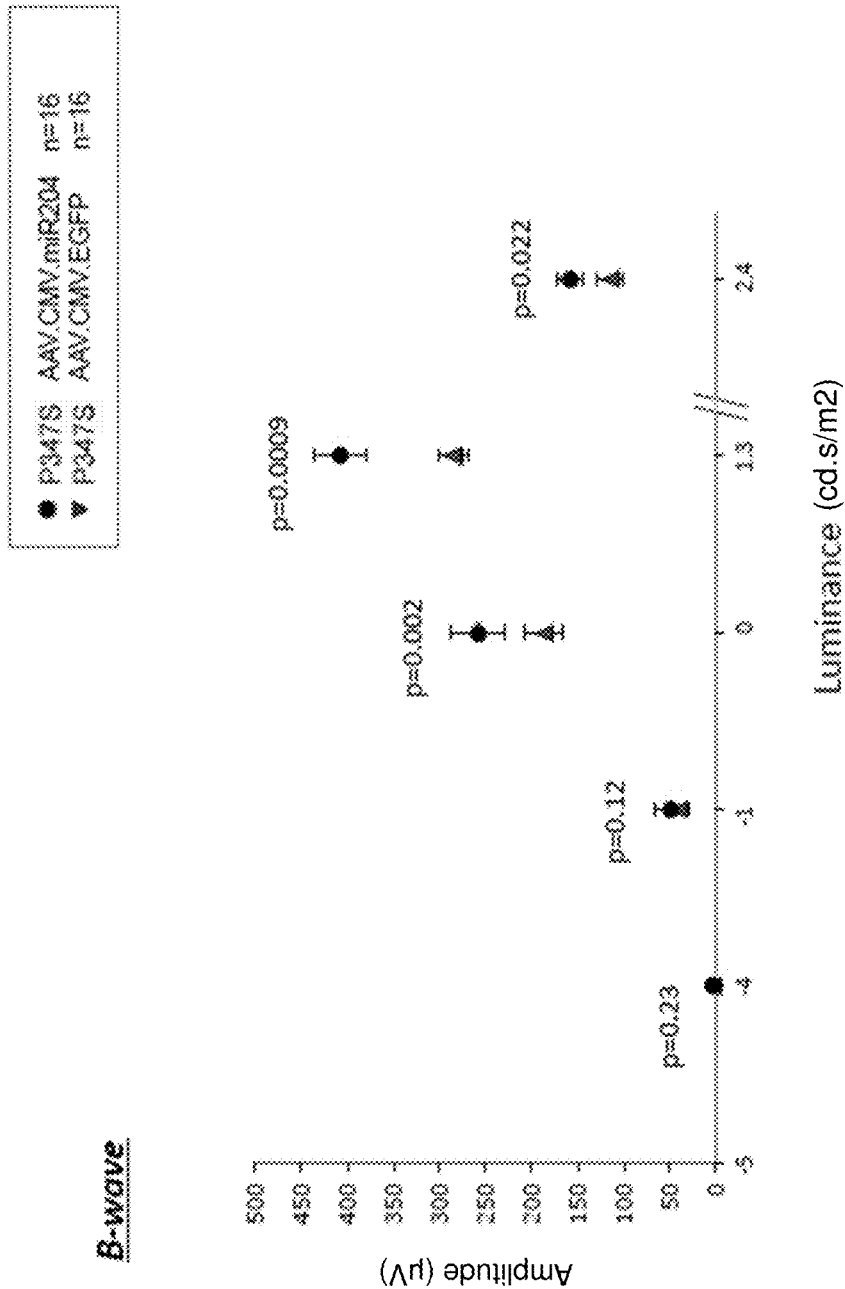

FIG. 6. Retinal function of P347S Rhodopsin transgenic mice following AAV-mediated delivery of miR-204 at postnatal day 4. In P347S mice, subretinal injection of AAV.CMV.premiR204 (n=16) results in an improvement of retinal function one month after injection, indicated by a statistically significant increase in b-wave ERG amplitude (P<0.05), compared to contralateral eyes injected with the control construct AAV.CMV.EGFP (n=16).

Figure 7:
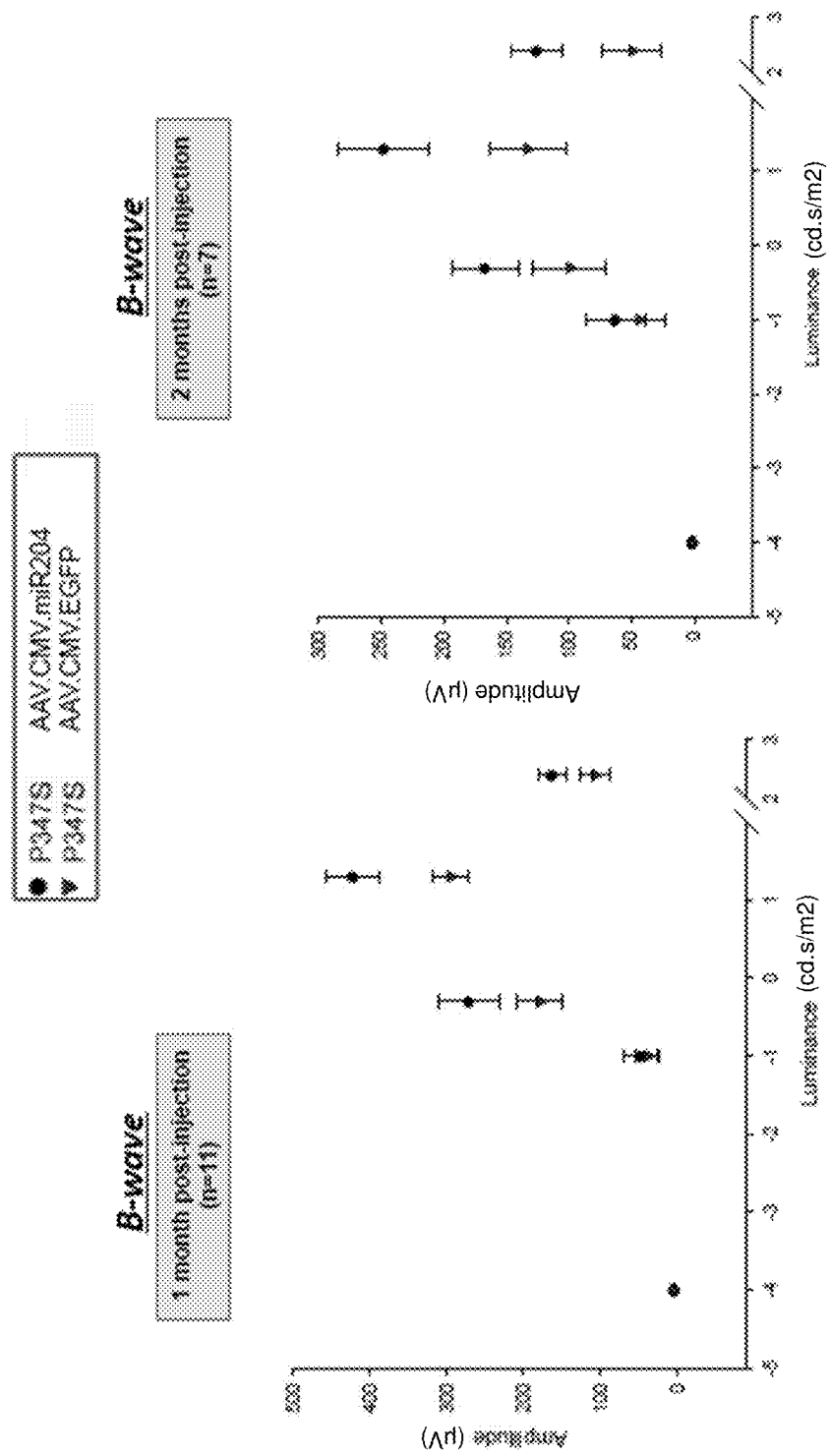

FIG. 7. Retinal function of Rhodopsin P347S transgenic mice 2 months after the AAV-mediated delivery of miR-204 at postnatal day 4. The improvement in retinal function, obtained following subretinal delivery of AAV.CMV.premiR204 in P347S mice was persistent up to at least 2 months post-injection as indicated by the increase in b-wave ERG amplitude, in treated eyes (n=7) compared to contralateral eyes injected with the control AAV.CMV.EGFP.

Figure 8:
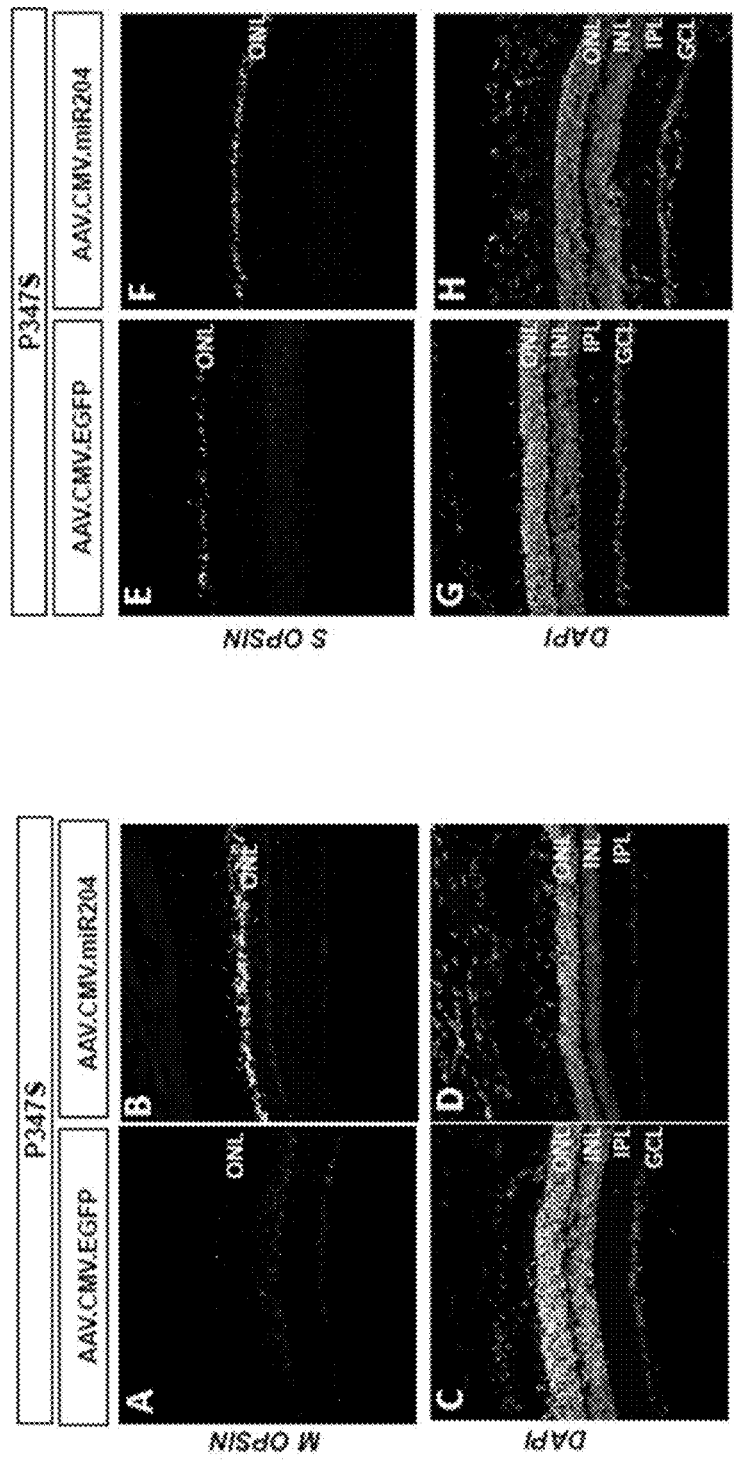

FIG. 8. Immunohistochemical analysis of photoreceptor markers in P347S mice following AAV-mediated delivery of miR-204. Confocal microscopy images of cone markers M-Opsin (A, B) and S-Opsin (E, F) immunolabeling on P40 retinal sections. An increased staining for these markers is observed in eyes injected with the AAV.CMV.premiR204 vectors compared with the contralateral control eyes. DAPI-staining of these sections is shown in C, D, G and H, respectively. Abbreviations: ONL, outer nuclear layer; INL, inner nuclear layer; IPL, inner plexiform layer; RPE, retinal pigment epithelium.

Figure 9:
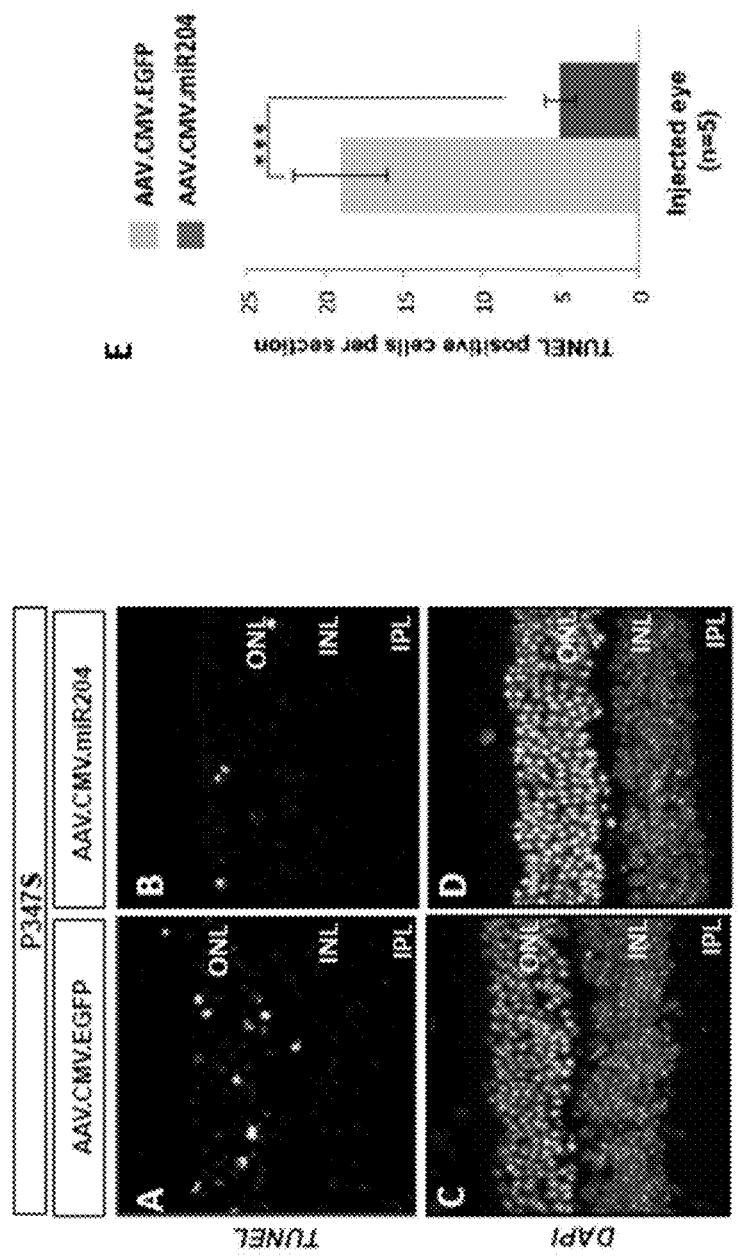

FIG. 9. Reduction of retinal cell-death in P347S mice following AAV-mediated delivery of miR-204. (A, B) Confocal microscopy images of TUNEL-stained retinal sections from eyes injected with the AAV.CMV.premiR204 (B) and control vectors (A). DAPI-staining of these sections is shown in C and D. Abbreviations: ONL, outer nuclear layer; INL, inner nuclear layer; IPL, inner plexiform layer. (E) The number of TUNEL-positive photoreceptors was quantified by counting corresponding sections from serially-sectioned, oriented eyes. There is a significant reduction (70%, P<0.001) in the number of apoptotic photoreceptor cells in the retina of P347S mice following injection of AAV.CMV.premiR204 compared to contralateral eyes injected with the control vector (n=5 retina; Error bars are SEM; *** p<0.001).

Figure 10:
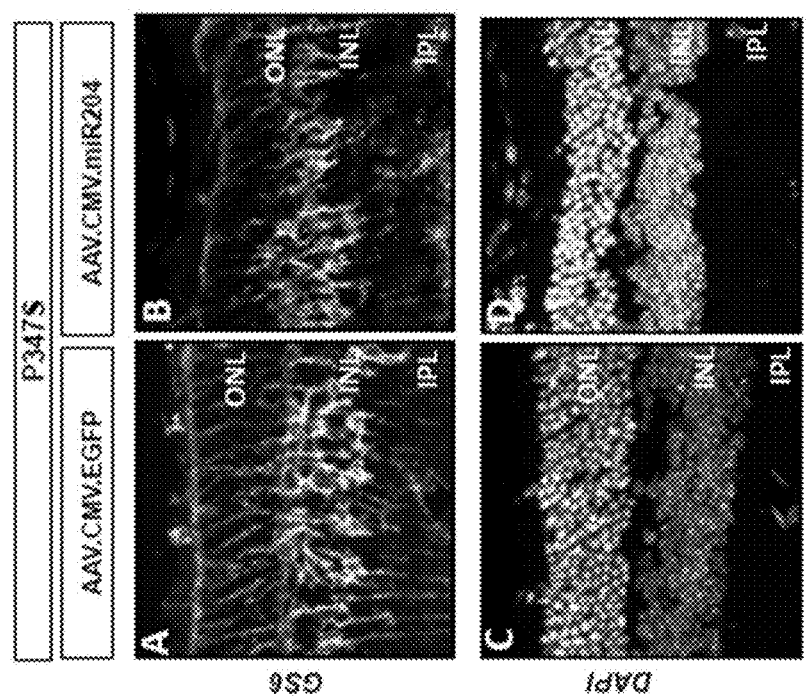

FIG. 10: Decrease of retinal gliosis in P347S mice following AAV-mediated delivery of miR-204. Confocal microscopy images (A, B) of anti-Glutamine Synthetase (GS6) immunolabeling on P40 retinal sections. A decrease in the number of activated retinal microglia cells (detected by staining for GS6) was observed in eyes injected with the AAV.CMV.premiR204 vector compared to the contralateral control eyes. DAPI-staining of these sections is shown in C and D. Abbreviations: ONL, outer nuclear layer; INL, inner nuclear layer; IPL, inner plexiform layer.

Figure 11:
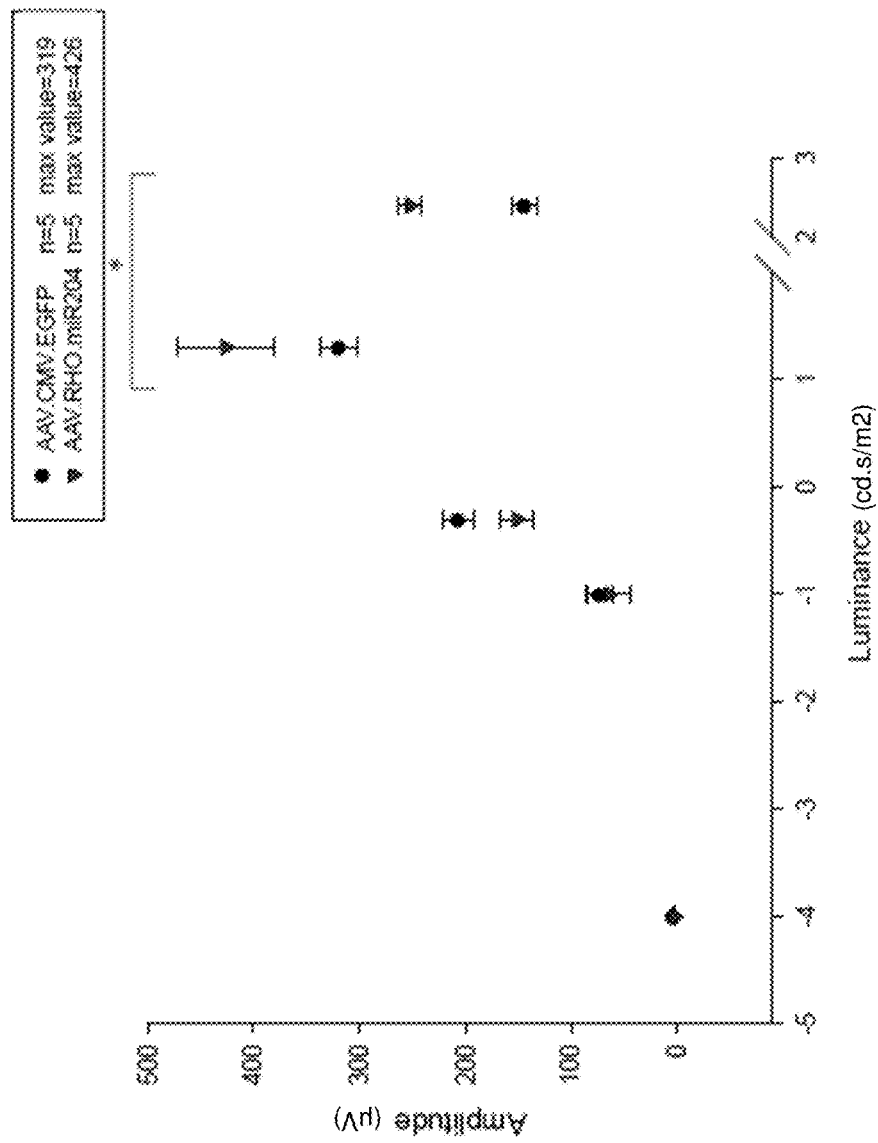

FIG. 11. Retinal function of P347S Rhodopsin transgenic mice following AAV-mediated overexpression of miR-204 under the control of a Rhodopsin (photoreceptor-specific) promoter at postnatal day 4. In P347S mice, subretinal injection of AAV.RHO.premiR204 (n=5), in which expression of the premiR-204 is under the control of a photoreceptor-specific (Rhodopsin) promoter, results in an improvement in retinal function, indicated by a statistically significant increase in b-wave ERG amplitude in treated eyes compared to contralateral eyes injected with the control AAV.CMV.EGFP (n=5).

Figure 12:
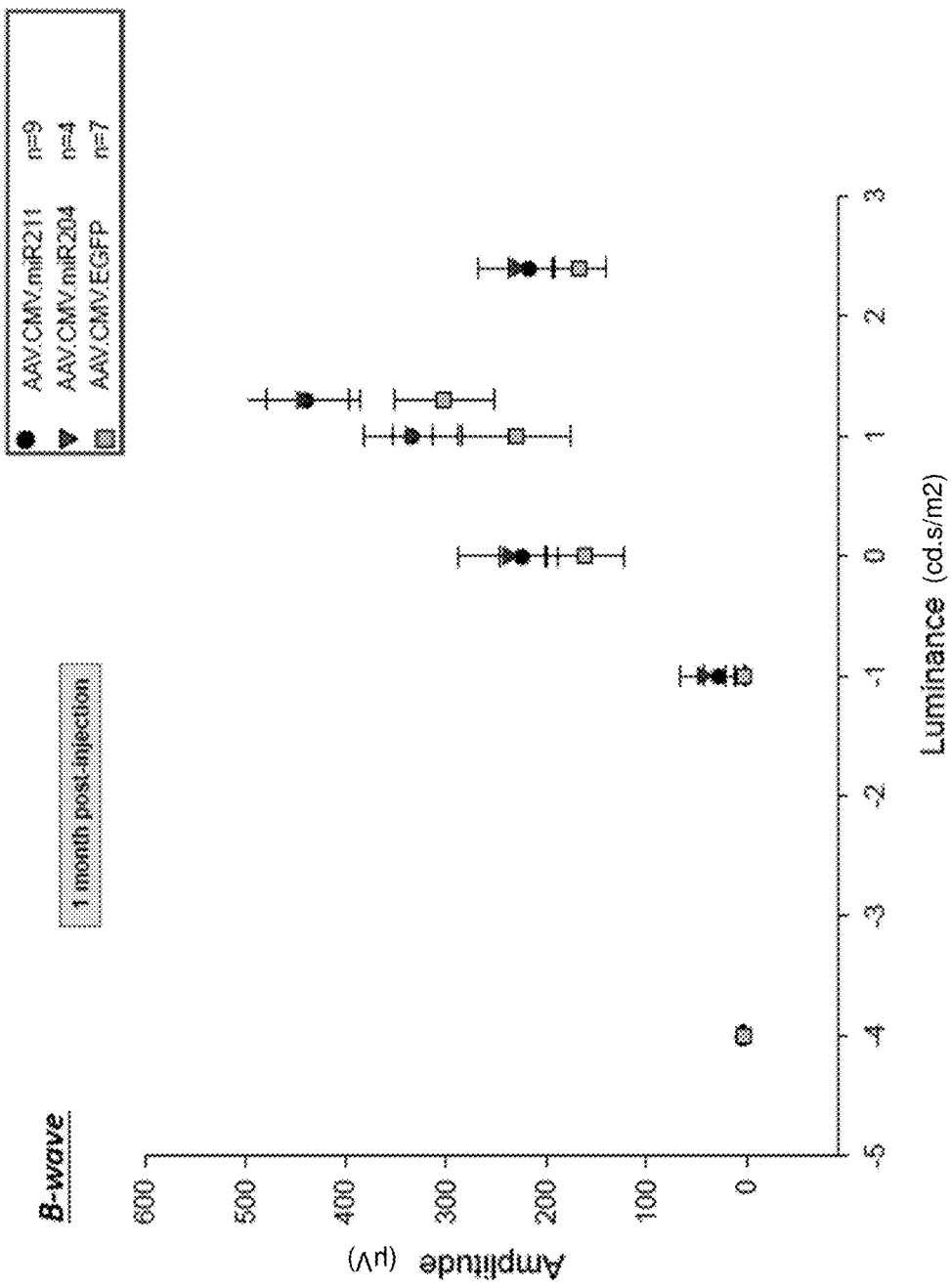

FIG. 12. The improvement of retinal function in P347S Rhodopsin transgenic mice following AAV-mediated delivery of miR-211 at postnatal day 4. In P347S mice, subretinal injection of either AAV.CMV.premiR204 (n=4) and AAV.CMV.premiR211 (n=9) results in a highly similar increase in b-wave ERG amplitude in treated eyes compared to contralateral eyes injected with the control AAV.CMV.EGFP (n=7).

Figure 13:
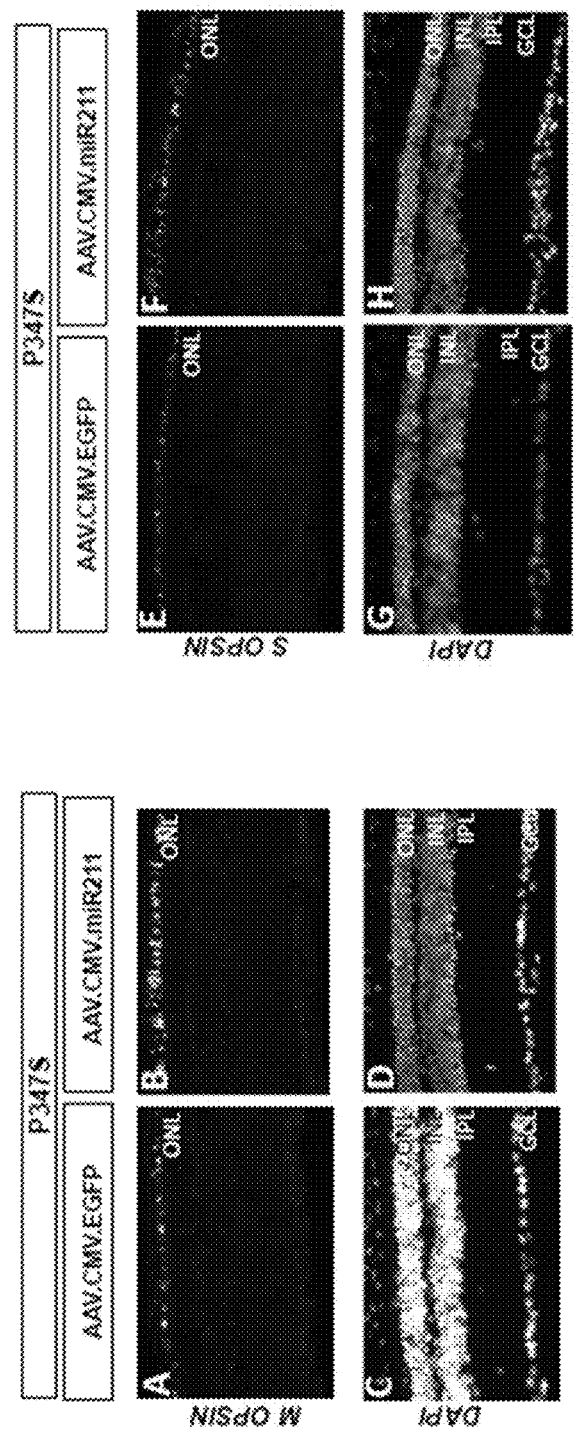

FIG. 13. Immunohistochemical analysis of cone photoreceptor markers in P347S mice following AAV-mediated delivery of miR-211. Fluorescence microscopy images of cone markers M-Opsin (A, B) and S-Opsin (E, F) immunolabeling on P40 retinal sections. An increased staining for these markers is observed in eyes injected with the AAV.CMV.premiR211 vectors compared with the contralateral control eyes. DAPI-staining of these sections is shown in C, D, G and H, respectively. Abbreviations: ONL, outer nuclear layer; INL, inner nuclear layer; IPL, inner plexiform layer; GCL, Ganglion Cell Layer.

Figure 14:
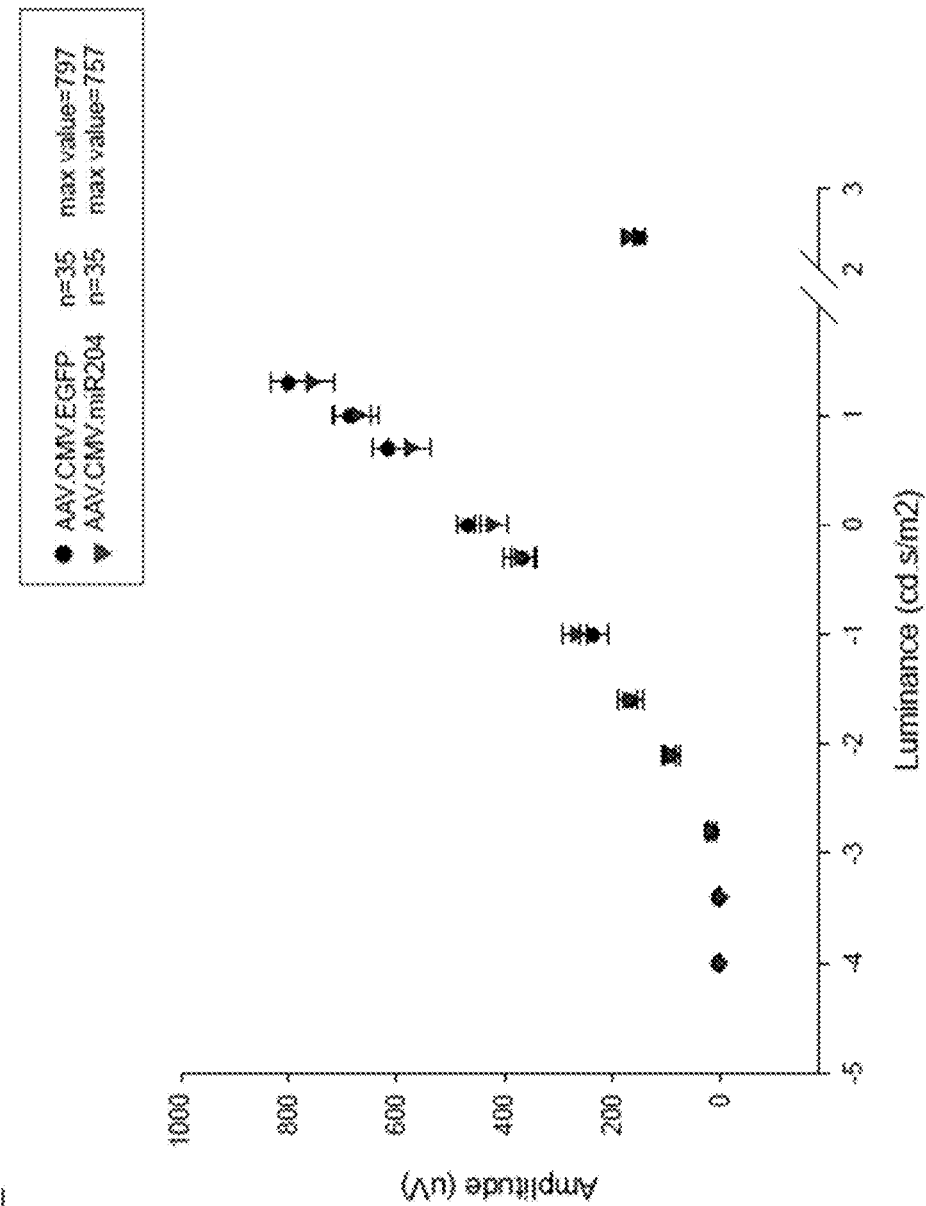

FIG. 14. Retinal function of wild-type C57/BL6 mice following AAV-mediated delivery of miR-204 at adult stages. In adult wild-type mice, subretinal injection of AAV.CMV.premiR204 does not impair retinal function, as indicated by the similarity in b-wave ERG responses, in treated eyes (n=35) compared to contralateral eyes, injected with the control AAV.CMV.EGFP (n=35).

Figure 15:
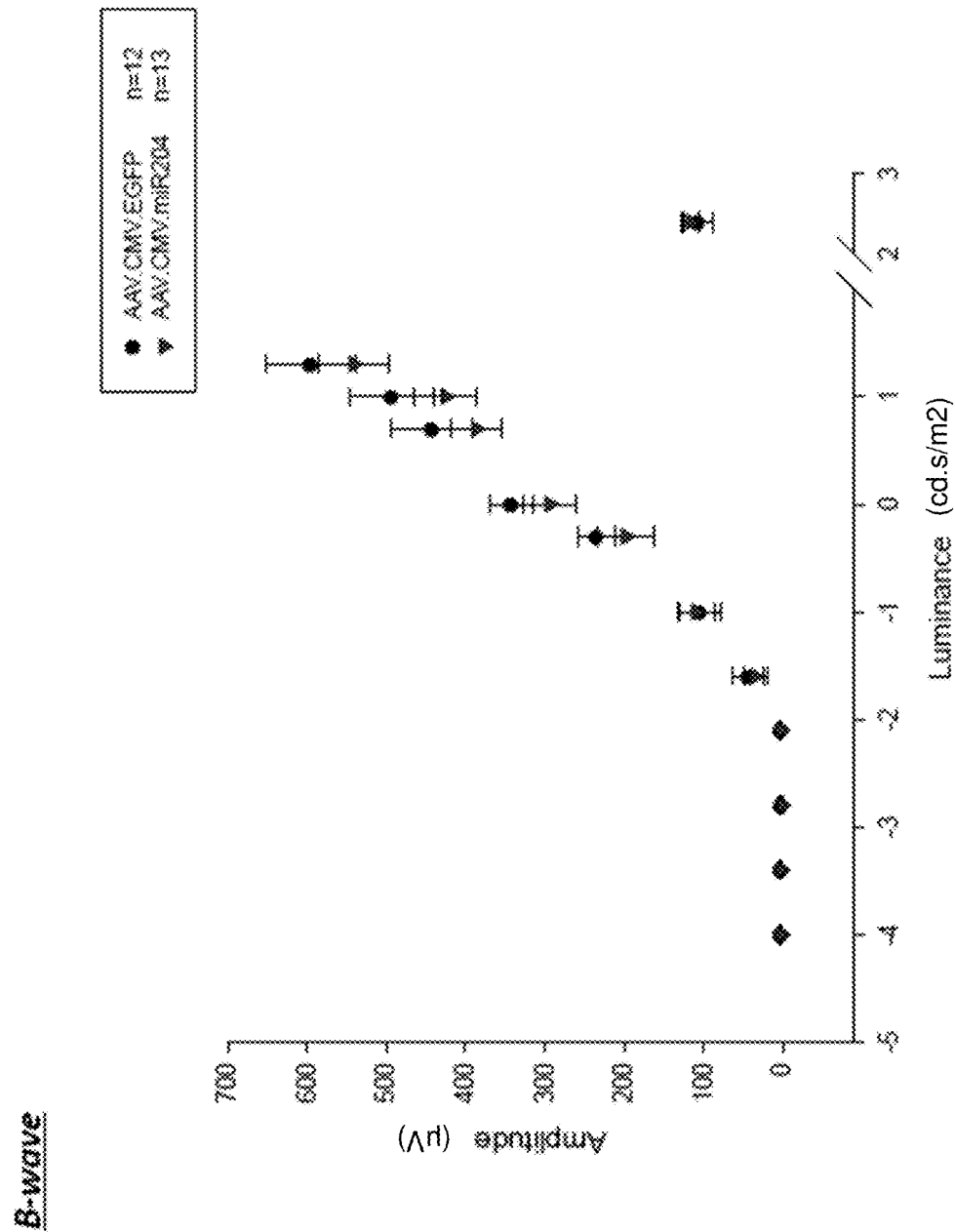

FIG. 15. Retinal function of wild-type C57/BL6 mice following AAV-mediated delivery of miR-204 at postnatal day 4. In wild-type pups, subretinal injection of AAV.CMV.premiR204 at postnatal (P) day 4 does not significantly impair retinal function, as indicated by the similarity of b-wave ERG responses in treated eyes (n=13) compared to contralateral eyes, injected with the control AAV.CMV.EGFP (n=12).

Figure 16:
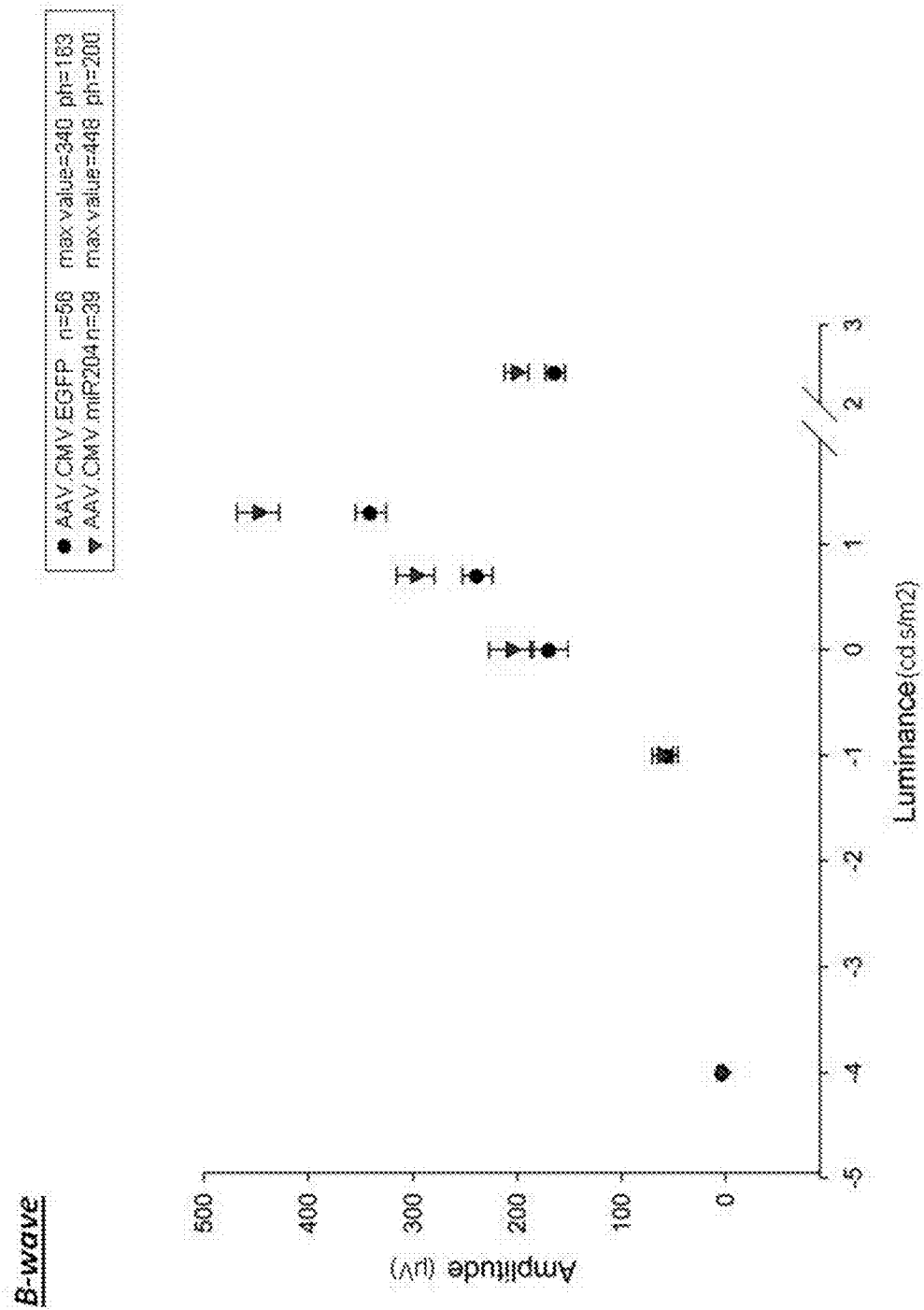

FIG. 16. Retinal function of P347S Rhodopsin transgenic mice following AAV-mediated delivery of miR-204 at postnatal day 4. In P347S mice, subretinal injection of AAV.CMV.premiR204 (n=39) results in an improvement of retinal function one month after injection, indicated by a statistically significant increase in b-wave ERG amplitude (P<0.05), compared to contralateral eyes injected with the control construct AAV.CMV.EGFP (n=56).

Figure 17:
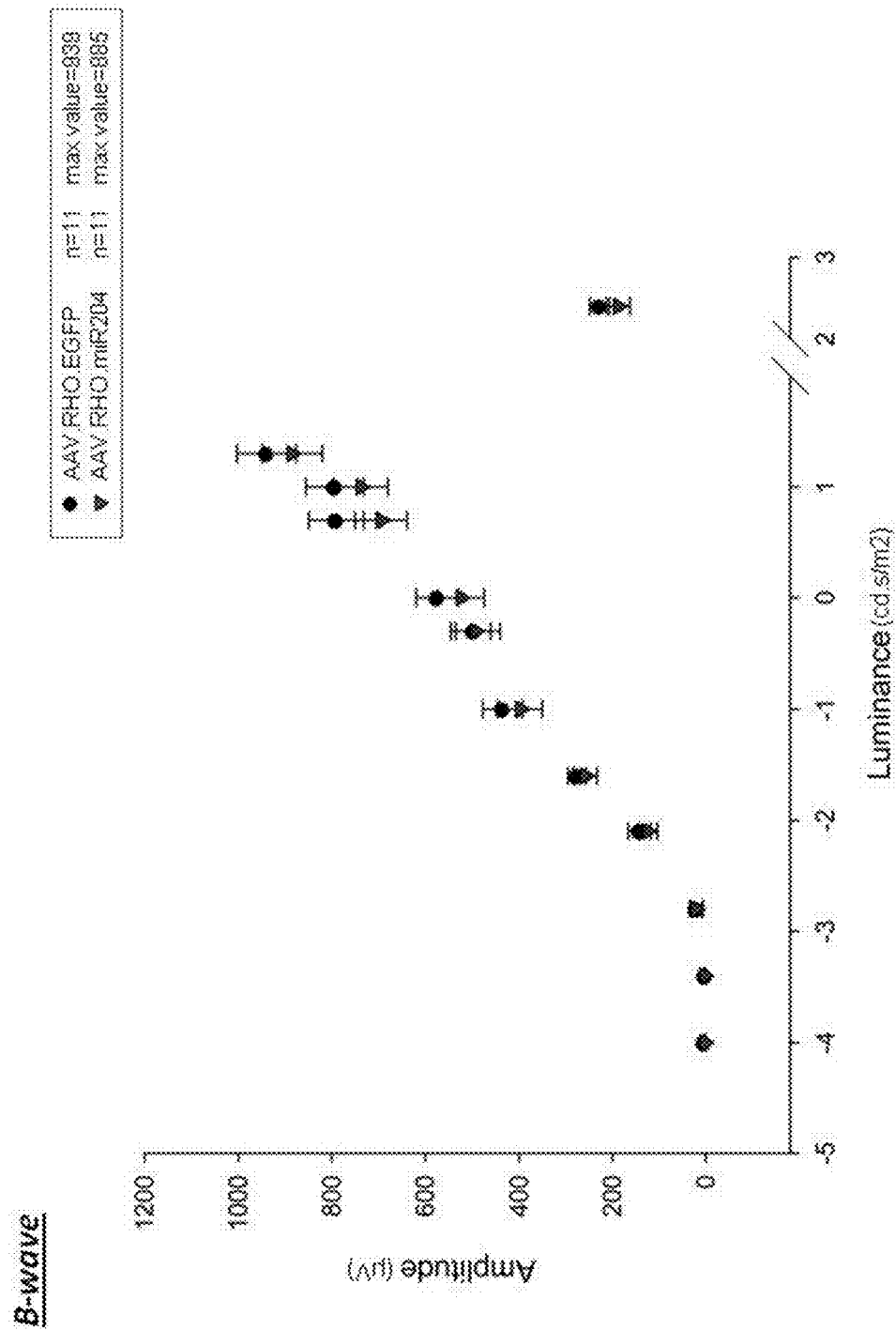

FIG. 17. Retinal function of wild-type C57/BL6 mice following AAV-mediated delivery of miR-204/211 at adult stages. In adult wild-type mice, subretinal injection of AAV.RHO.premiR204/miR211 does not impair retinal function, as indicated by the similarity in b-wave ERG responses, in treated eyes (n=11) compared to contralateral eyes, injected with the control AAV.RHO.EGFP (n=11).

Figure 18:
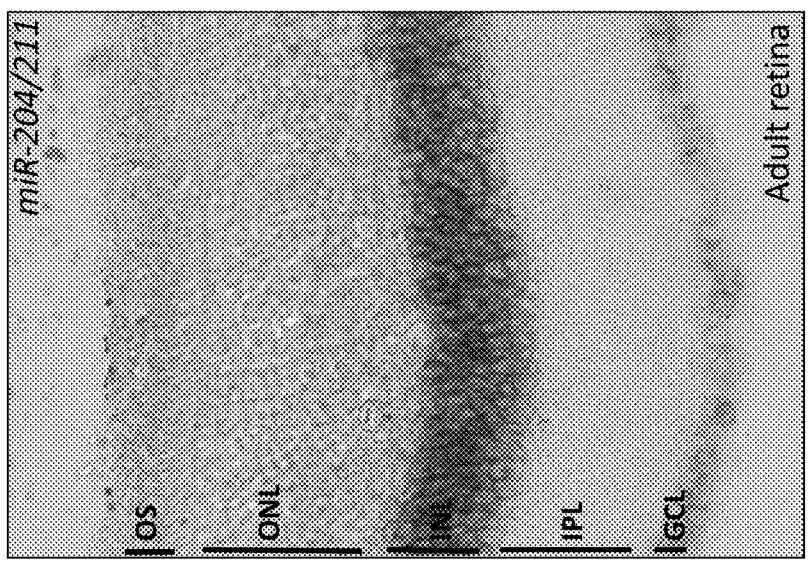

FIG. 18. miR-204/211 expression in retinal sections from adult wild-type mice. RNA ISH for miR-204 using a miRCURY™ LNA Detection probe (Exiqon). In the neural retina, miR-204/211 is strongly expressed in INL and the GCL while no expression is detected in the photoreceptor layers (ONL and OS). Abbreviations: GCL, Ganglion Cell Layer; INL, Inner Nuclear Layer; IPL, Inner Plexiform Layer; ONL, Outer Nuclear FIG. 19. Retinal function of miR-211 knockout mice at 3 months. A statistically significant decrease in b-wave ERG amplitude (P<0.05) was observed in both miR-211 homozygous (OMO) and heterozygous (HET) KO mice compared to wild type (WT).

FIG. 20. The human eye. a) Schematic representation of the human eye b) Cross-section of the human retina, showing its laminated structure, which consists of: (1) the ganglion cell layer, the axons of which form the optic nerve, which connects the retina to the brain; (2) the inner nuclear layer, which contains second-order neurons, such as bipolar, amacrine and horizontal cells; (3) the outer nuclear layer of photoreceptor (PR), which contains the cell bodies and nuclei of the rod and cone PRs; (4) the PR outer segments, which are densely packed with opsin-containing discs and are separated from the inner segments and cell bodies by a narrow 200-500 nm-long connecting cilium (not visible); and (5) the retinal pigment epithelium (RPE), a monolayer of cells containing tight junctions that separates the neural retina from the choroid, which supplies blood to the RPE and PRs (outer retina). Please note that PR cells are present in layers (3) and (4) and are clearly distinct from the RPE (5). Modified from: Photoreceptor degeneration: genetic and mechanistic dissection of a complex trait. Wright A F, Chakarova C F, Abd El-Aziz M M, Bhattacharya S S. Nat Rev Genet. 2010 April; 11(4):273-84.

DETAILED DESCRIPTION OF THE INVENTION

Material and Methods

Sequences

>hsa-mir-204

SEQ ID NO: 6

GGCUACAGUCUUUCUUCAUGUGACUCGUGGACUUCCCUUUGUCAUCCUAUGCCUGAGAAUAUAUGAAGG
AGGCUGGGAAGGCAAAGGGACGUUCAAUUGUCAUCACUGGC

Mature sequence (in bold) from base 33 to base 54
Seed sequence (underscored) from base 33 to base 39

>mmu-mir-204

SEQ ID NO: 7

UGGACUUCCCUUUGUCAUCCUAUGCCUGAGAAUAUAUGAAGGAGGCUGGGAAGGCAAAGGGACGUUCA

Mature sequence (in bold) from base 6 to base 27
Seed sequence (underscored) from base 6 to base 12

>hsa-mir-211

SEQ ID NO: 8

UCACCUGGCCAUGUGACUUGUGGGCUUCCCUUUGUCAUCCUUCGCCUAGGGCUCUGAGCAGGGCAGGGA
CAGCAAAGGGGUGCUCAGUUGUCACUUCCCACAGCACGGAG

Mature sequence (in bold) from base 26 to base 47
Seed sequence (underscored) from base 26 to base 32

>mmu-mir-211

SEQ ID NO: 9

CUGCUUGGACCUGUGACCUGUGGGCUUCCCUUUGUCAUCCUUUGCCUAGGCCUCUGAGUGAGGCAAGGA
CAGCAAAGGGGGCUCAGUGGUCACCUCUACUGCAGA

Mature sequence (in bold) from base 26 to base 47
Seed sequence (underscored) from base 26 to base 32

>pAAV.CMV.premiR204
underscore sequence is the sequence of the pre-miR204

SEQ ID NO: 10

AGCGCCCAATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACACAG
GAAACAGCTATGACCATGATTACGCCAGATTTAATTAAGGCTGCGCGCTCGCTCGCTCACTGAGGCCGC
CCGGGCAAAGCCCGGGCGTCGGGCGACCTTTGGTCGCCCGGCCTCAGTGAGCGAGCGAGCGCGCAGAGA
GGGAGTGGCCAACTCCATCACTAGGGGTTCCTTGTAGTTAATGATTAACCCGCCATGCTACTTATCTAC
GTAGCCATGCTCTAGGAAGATCGGAATTCGCCCTTAAGCTAGCTAGTTATTAATAGTAATCAATTACGG
GGTCATTAGTTCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGTACATCAAGTGTATC
ATATGCCAAGTACGCCCCCTATTGACGTCAATGACGGTAAATGGCCCGCCTGGCATTATGCCCAGTACA
TGACCTTATGGGACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAAGTCTCCACCCCA
TTGACGTCAATGGGAGTTTGTTTTGGCACCAAAATCAACGGGACTTTCCAAAATGTCGTAACAACTCCG
CCCCATTGACGCAAATGGGCGGTAGGCGTGTACGGTGGGAGGTCTATATAAGCAGAGCTGGTTTAGTGA
ACCGTCAGATCCTGCAGAAGTTGGTCGTGAGGCACTGGGCAGGTAAGTATCAAGGTTACAAGACAGGTT
TAAGGAGACCAATAGAAACTGGGCTTGTCGAGACAGAGAAGACTCTTGCGTTTCTGATAGGCACCTATT
GGTCTTACTGACATCCACTTTGCCTTTCTCTCCACAGGTGTCCAGGCGGCCGCCTGTTCAGGACTTGGC
TAAGCATTGCTTTGAACAAAATATCAAACAAGGACTCAAGGGGCAGAGAATGCTGGTCAGTGGCTAAGA
TGCCGGAGAATCAAGATGAGCAGGAAATGAAGAGGTTGGCTAAGAGGGGCAGAGGAGGCAGGCGGAGGA
GCTCCTGACCGTGTACCATGGCTACAGTCCTTCTTCATGTGACTCGTGGACTTCCCTTTGTCATCCTAT
GCCTGAGAATATATGAAGGAGGCTGGGAAGGCAAAGGGACGTTCAATTGTCATCACTGGCATCTTTTTT
GATCATTACACCATCATCAAAAGCATTTGGATAACCATAACATGAAAATTACCATCATTGAGCCCATAA
CTTTCCTAAGACAAGGGTGACAATTTGAAACATCAAAGAACCTTACCCAGGGAATTCAAGAAGTGAGAA
GAGTGAATCAGATTCTCCCAGATTAACAACCCCATGTTGGATCCAATCAACCTCTGGATTACAAAATTT
GTGAAAGATTGACTGGTATTCTTAACTATGTTGCTCCTTTTACGCTATGTGGATACGCTGCTTTAATGC
CTTTGTATCATGCTATTGCTTCCCGTATGGCTTTCATTTTCTCCTCCTTGTATAAATCCTGGTTGCTGT
CTCTTTATGAGGAGTTGTGGCCCGTTGTCAGGCAACGTGGCGTGGTGTGCACTGTGTTTGCTGACGCAA
CCCCCACTGGTTGGGGCATTGCCACCACCTGTCAGCTCCTTTCCGGGACTTTCGCTTTCCCCCTCCCTA
TTGCCACGGCGGAACTCATCGCCGCCTGCCTTGCCCGCTGCTGGACAGGGGCTCGGCTGTTGGGCACTG
ACAATTCCGTGGTGTTGTCGGGGAAGCTGACGTCCTTTCCATGGCTGCTCGCCTGTGTTGCCACCTGGA
TTCTGCGCGGGACGTCCTTCTGCTACGTCCCTTCGGCCCTCAATCCAGCGGACCTTCCTTCCCGCGGCC
TGCTGCCGGCTCTGCGGCCTCTTCCGCGTCTTCGAGATCTGCCTCGACTGTGCCTTCTAGTTGCCAGCC
ATCTGTTGTTTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGGGTGGGGCA

Material and Methods

```
GGACAGCAAGGGGGAGGATTGGGAAGACAATAGCAGGCATGCTGGGGACTCGAGTTAAGGGCGAATTCC
CGATTAGGATCTTCCTAGAGCATGGCTACGTAGATAAGTAGCATGGCGGGTTAATCATTAACTACAAGG
AACCCCTAGTGATGGAGTTGGCCACTCCCTCTCTGCGCGCTCGCTCACTGAGGCCGGGCGACCAA
AGGTCGCCCGACGCCCGGGCTTTGCCCGGGCGGCCTCAGTGAGCGAGCGAGCGCGCAGCCTTAATTAAC
CTAATTCACTGGCCGTCGTTTTACAACGTCGTGACTGGGAAAACCCTGGCGTTACCCAACTTAATCGCC
TTGCAGCACATCCCCCTTTCGCCAGCTGGCGTAATAGCGAAGAGGCCCGCACCGATCGCCCTTCCCAAC
AGTTGCGCAGCCTGAATGGCGAATGGGACGCGCCCTGTAGCGGCGCATTAAGCGCGGCGGGTGTGGTGG
TTACGCGCAGCGTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGGGTTCCGATTTA
GTGCTTTACGGCACCTCGACCCCAAAAAACTTGATTAGGGTGATGGTTCACGTAGTGGGCCATCGCCCC
GATAGACGGTTTTTCGCCCTTTGACGCTGGAGTTCACGTTCCTCAATAGTGGACTCTTGTTCCAAACTG
GAACAACACTCAACCCTATCTCGGTCTATTCTTTTGATTTATAAGGGATTTTTCCGATTTCGGCCTATT
GGTTAAAAAATGAGCTGATTTAACAAAAATTTAACGCGAATTTTAACAAAATATTAACGTTTATAATTT
CAGGTGGCATCTTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAAGGAAGAGTATGAGTA
TTCAACATTTCCGTGTCGCCCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTGGGTTACATCGAACTGGATC
TCAATAGTGGTAAGATCCTTGAGAGTTTTCGCCCCGAAGAACGTTTTCCAATGATGAGCACTTTTAAAG
TTCTGCTATGTGGCGCGGTATTATCCCGTATTGACGCCGGGCAAGAGCAACTCGGTCGCCGCATACACT
ATTCTCAGAATGACTTGGTTGAGTACTCACCAGTCACAGAAAAGCATCTTACGGATGGCATGACAGTAA
GAGAATTATGCAGTGCTGCCATAACCATGAGTGATAACACTGCGGCCAACTTACTTCTGACAACGATCG
GAGGACCGAAGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGTAGTAATGGTAACAA
CGTTGCGCAAACTATTAACTGGCGAACTACTTACTCTAGCTTCCCGGCAACAATTAATAGACTGGATGG
AGGCGGATAAAGTTGCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATGGTAAGCCCTCCCGTA
TCGTAGTTATCTACACGACGGGGAGTCAGGCAACTATGGATGAACGAAATAGACAGATCGCTGAGATAG
GTGCCTCACTGATTAAGCATTGGTAACTGTCAGACCAAGTTTACTCATATATACTTTAGATTGATTTAA
AACTTCATTTTTAATTTAAAAGGATCTAGGTGAAGATCCTTTTTGATAATCTCATGACCAAAATCCCTT
AACGTGAGTTTTCGTTCCACTGAGCGTCAGACCCCGTAGAAAAGATCAAAGGATCTTCTTGAGATCCTT
TTTTTCTGCGCGTAATCTGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACAGCCCAGCTTGGAGCGAA
CGACCTACACCGAACTGAGATACCTACAGCGTGAGCTATGAGAAAGCGCCACGCTTCCCGAAGGGAGAA
AGGCGGACAGGTATCCGGTAAGCGGCAGGGTCGGAACAGGAGAGCGCACGAGGGAGCTTCCAGGGGGAA
ACGCCTGGTATCTTTATAGTCCTGTCGGGTTTCGCCACCTCTGACTTGAGCGTCGATTTTTGTGATGCT
CGTCAGGGGGCGGAGCCTATGGAAAAACGCCAGCAACGCGGCCTTTTTACGGTTCCTGGCCTTTTGCT
GCGGTTTTGCTCACATGTTCTTTCCTGCGTTATCCCCTGATTCTGTGGATAACCGTATTACCGCTTTG
AGTGAGCTGATACCGCTCGCCGCAGCCGAACGACCGAGCGCAGCGAGTCAGTGAGCGAGGAAGCGGAAG
```

>pAAV.CMV.premiR211
underscore sequence is the sequence of the pre-miR211

SEQ ID NO: 11
```
AGCGCCCAATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACACAG
GAAACAGCTATGACCATGATTACGCCAGATTTAATTAAGGCTGCGCGCTCGCTCGCTCACTGAGGCCGC
CCGGGCAAAGCCCGGGCGTCGGGCGACCTTTGGTCGCCCGGCCTCAGTGAGCGAGCGAGCGCGCAGAGA
GGGAGTGGCCAACTCCATCACTAGGGGTTCCTTGTAGTTAATGATTAACCCGCCATGCTACTTATCTAC
GTAGCCATGCTCTAGGAAGATCGGAATTCGCCCTTAAGCTAGCTAGTTATTAATAGTAATCAATTACGG
GGTCATTAGTTCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGTACATCAAGTGTATC
ATATGCCAAGTACGCCCCCTATTGACGTCAATGACGGTAAATGGCCCGCCTGGCATTATGCCCAGTACA
TGACCTTATGGGACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAAGTCTCCACCCCA
TTGACGTCAATGGGAGTTTGTTTTGGCACCAAAATCAACGGGACTTTCCAAAATGTCGTAACAACTCCG
CCCCATTGACGCAAATGGGCGGTAGGCGTGTACGGTGGGAGGTCTATATAAGCAGAGCTGGTTTAGTGA
ACCGTCAGATCCTGCAGAAGTTGGTCGTGAGGCACTGGGCAGGTAAGTATCAAGGTTACAAGACAGGTT
TTTAAGGAGACCAATAGAAACTGGGCTTGTCGAGACAGAGAAGACTCTTGCGTCTGATAGGCACCTATT
GGTCTTACTGACATCCACTTTGCCTTTCTCTCCACAGGTGTCCAGGCGGCCGCTCTGACCATGCAATCA
CAGGTGTGGGGCATCCACTAGAGTGTGGTCAACCTATCAGGGCCGCACACTTAAAAAAAAAAACTGAC
TCCCTTCCCACAGAAGGGAATTTGTCAACTCCTCCCCACCCTCATGCTGGAATACTGACCGGCTTGATC
CTGTGCAGCCAGCCACACTGTGAGTTCATGAGTGCGGAGGTCCTAAGAATCAGATCTTGGTGGATAAAT
CAGTTTGATTTAGTGTTTTTGGACTTGTAAATTCTGCTTGGACCTGTGACCTGTGGGCTTCCCTTTGTC
ATCCTTTGCCTAGGCCTCTGAGTGAGGCAAGGACAGCAAAGGGGGGCTCAGTGGTCACCTCTACTGCAG
AGAGTTCAGAAGCCTAGCCTGAGCCAAGAGCAAGTTCTTCTCTGCTTCTGGAAATGAAGTCGCCATGAT
CCTGACGATGTAAAAATCCCAAGCACGCTTGGATGGAAATCTCAGAGACAGACGATGCCACCCTGATCC
ATTGGATCCAATCAACCTCTGGATTACAAAATTTGTGAAAGATTGACTGGTATTCTTAACTATGTTGCT
CCTTTTACGCTATGTGGATACGCTGCTTTAATGCCTTTGTATCATGCTATTGCTTCCCGTATGGCTTTC
ATTTTCTCCTCCTTGTATAAATCCTGGTTGCTGTCTCTTTATGAGGAGTTGTGGCCCGTTGTCAGGCAA
CGTGGCGTGGTGTGCACTGTGTTTGCTGACGCAACCCCCACTGGTTGGGGCATTGCCACCACCTGTCAG
CTCCTTTCCGGGACTTTCGCTTTCCCCCTCCCTATTGCCACGGCGGAACTCATCGCCGCCTGCCTTGCC
CGCTGCTGGACAGGGGCTCGGCTGTTGGGCACTGACAATTCCGTGGTGTTGTCGGGGAAGCTGACGTCC
TTTCCATGGCTGCTCGCCTGTGTTGCCACCTGGATTCTGCGCGGGACGTCCTTCTGCTACGTCCCTTCG
```

Material and Methods

```
GCCCTCAATCCAGCGGACCTTCCTTCCCGCGGCCTGCTGCCGGCTCTGCGGCCTCTTCCGCGTCTTCGA
GATCTGCCTCGACTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCTGAGTA
GGTGTCATTCTATTCTGGGGGGTGGGGTGGGGCAGGACAGCAAGGGGGAGGATTGGGAAGACAATAGCA
GGCATGCTGGGGACTCGAGTTAAGGGCGAATTCCCGATTAGGATCTTCCTAGAGCATGGCTACGTAGAT
AAGTAGCATGGCGGGTTAATCATTAACTACAAGGAACCCCTAGTGATGGAGTTGGCCACTCCCTCTCTG
CGCGCTCGCTCGCTCACTGAGGCCGGGCGACCAAAGGTCGCCCGACGCCCGGGCTTTGCCCGGGCGGCC
TCAGTGAGCGAGCGAGCGCGCAGCCTTAATTAACCTAATTCACTGGCCGTCGTTTTACAACGTCGTGAC
TGGGAAAACCCTGGCGTTACCCAACTTAATCGCCTTGCAGCACATCCCCCTTTCGCCAGCTGGCGTAAT
AGCGAAGAGGCCCGCACCGATCGCCCTTCCCAACAGTTGCGCAGCCTGAATGGCGAATGGGACGCGCCC
TGTAGCGGCGCATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCCCGTCAAGCT
CTAAATCGGGGGCTCCCTTTAGGGTTCCGATTTAGTGCTTTACGGCACCTCGACCCCAAAAAACTTGAT
TAGGGTGATGGTTCACGTAGTGGGCCATCGCCCCGATAGACGGTTTTTCGCCCTTTGACGCTGGAGTTC
ACGTTCCTCAATAGTGGACTCTTGTTCCAAACTGGAACAACACTCAACCCTATCTCGGTCTATTCTTTT
GATTTATAAGGGATTTTTCCGATTTCGGCCTATTGGTTAAAAAATGAGCTGATTTAACAAAAATTTAAC
GCGAATTTTAACAAAATATTAACGTTTATAATTTCAGGTGGCATCTTTCGGGGAAATGTGCGCGGAACC
CCTATTTGTTTATTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTTATTCCCTTTTTT
GCGGCATTTTGCCTTCCTGTTTTTGCTCACCCAGAAACGCTGGTGAAAGTAAAAGATGCTGAAGATCAG
TTGGGTGCACGAGTGGGTTACATCGAACTGGATCTCAATAGTGGTAAGATCCTTGAGAGTTTTCGCCCC
GAAGAACGTTTTCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAGTACTCACCAGTC
ACAGAAAAGCATCTTACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACCGCTTTTTTGCACAAC
ATGGGGGATCATGTAACTCGCCTTGATCGTTGGGAACCGGAGCTGAATGAAGCCATACCAAACGACGAG
CGTGACACCACGATGCCTGTAGTAATGGTAACAACGTTGCGCAAACTATTAACTGGCGAACTACTTACT
CTAGCTTCCCGGCAACAATTAATAGACTGGATGGAGGCGGATAAAGTTGCAGGACCGTAGTTAGGCCAC
GCCCTTCCGGCTGGCTGGTTTATTGCTGATAAATCTGGAGCCGGTGAGCGTGGGTCTCGCGGTATCATT
GCAGCACTGGGGCCAGATGGTAAGCCCTCCCGTATCGTAGTTATCTACACGACGGGGAGTCAGGCAACT
ATGGATGAACGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATCTAGGTGAAG
ATCCTTTTTGATAATCTCATGACCAAAATCCCTTAACGTGAGTTTTCGTTCCACTGAGCGTCAGACCCC
GTAGAAAAGATCAAAGGATCTTCTTGAGATCCTTTTTTTCTGCGCGTAATCTGCTGCTTGCAAACAAAA
AAACCACCGCTACCAGCGGTGGTTTGTTTGCCGGATCAAGAGCTACCAACTCTTTTTCCGAAGGTAACT
GGCTTCAGCAGAGCGCAGATACCAAATACTGTCCTTCTAGTGTAGCCGTAGTTAGGCCACCACTTCAAG
AACTCTGTAGCACCGCCTACATACCTCGCTCTGCTAATCCTGTTACCAGTGGCTGCTGCCAGTGGCGAT
AAGTCGTGTCTTACCGGGTTGGACTCAAGACGATAGTTACCGGATAAGGCGCAGCGGTCGGGCTGAACG
GGGGGTTCGTGCACACAGCCCAGCTTGGAGCGAACGACCTACACCGAACTGAGATACCTACAGCGTGAG
CTATGAGAAAGCGCCACGCTTCCCGAAGGGAGAAAGGCGGACAGGTATCCGGTAAGCGGCAGGGTCGGA
ACAGGAGAGCGCACGAGGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGGCGGAGCCTATGGAAAAACGCCAGC
AACGCGGCCTTTTTACGGTTCCTGGCCTTTTGCTGCGGTTTTGCTCACATGTTCTTTCCTGCGTTATCC
CCTGATTCTGTGGATAACCGTATTACCGCCTTTGAGTGAGCTGATACCGCTCGCCGCAGCCGAACGACC
GAGCGCAGCGAGTCAGTGAGCGAGGAAGCGGAAG
``` pAAV.RHO.premiR204
underscored sequence is the sequence of the pre-miR204
bold sequence is the sequence of the human RHO promoter

SEQ ID NO: 12

```
AGCGCCCAATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACACAG
GAAACAGCTATGACCATGATTACGCCAGATTTAATTAAGGCTGCGCGCTCGCTCGCTCACTGAGGCCGC
CCGGGCAAAGCCCGGGCGTCGGGCGACCTTTGGTCGCCCGGCCTCAGTGAGCGAGCGAGCGCGCAGAGA
GGGAGTGGCCAACTCCATCACTAGGGGTTCCTTGTAGTTAATGATTAACCCGCCATGCTACTTATCTAC
GTAGCCATGCTCTAGGAAGATCGGAATTCGCCCTTAAGCTAGCAGATCTTCCCCACCTAGCCACCTGGC
AAACTGCTCCTTCTCTCAAAGGCCCAAACATGGCCTCCCAGACTGCAACCCCCAGGCAGTCAGGCCCTG
TCTCCACAACCTCACAGCCACCCTGGACGGAATCTGCTTCTTCCCACATTTGAGTCCTCCTCAGCCCCT
GAGCTCCTCTGGGCAGGGCTGTTTCTTTCCATCTTTGTATTCCCAGGGGCCTGCAAATAAATGTTTAAT
GAACGAACAAGAGAGTGAATTCCAATTCCATGCAACAAGGATTGGGCTCCTGGGCCCTAGGCTATGTGT
CTGGCACCAGAAACGGAAGCTGCAGGTTGCAGCCCCTGCCCTCATGGAGCTCCTCCTGTCAGAGGAGTG
TGGGGACTGGATGACTCCAGAGGTAACTTGTGGGGGAACGAACAGGTAAGGGGCTGTGTGACGAGATGA
GAGACTGGGAGAATAAACCAGAAAGTCTCTAGCTGTCCAGAGGACATAGCACAGAGGCCCATGGTCCCT
ATTTCAAACCCAGGCCACCAGACTGAGCTGGGACCTTGGGACAGACAAGTCATGCAGAAGTTAGGGGAC
CTTCTCCTCCCTTTTCCTGGATCCTGAGTACCTCTCCTCCCTGACCTCAGGCTTCCTCCTAGTGTCACC
TTGGCCCCTCTTAGAAGCCAATTAGGCCCTCAGTTTCTGCAGCGGGGATTAATATGATTATGAACACCC
CCAATCTCCCAGATGCTGATTCAGCCAGGAGCTTAGGAGGGGAGGTCACTTTATAAGGGTCTGGGGGG
GTCAGAACCCAGAGTCATCCGCCTGAATTCTGCAGATATCCATCACACTGGCGGCCGC<u>CTGTTCAGGAC
TTGGCTAAGCATTGCTTTGAACAAAATATCAAACAAGGACTCAAGGGGCAGAGAATGCTGGTCAGTGGC
TAAGATGCCGGAGAATCAAGATGAGCAGGAAATGAAGAGGTTGGCTAAGAGGGGCAGAGGAGGCAGGCG
GAGGAGCTCCTGACCGTGTACCATGGCTACAGTCCTTCTTCATGTGACTCGTGGACTTCCCTTTGTCAT
CCTATGCCTGAGAATATATGAAGGAGGCTGGAAGGCAAAGGGACGTTCAATTGTCATCACTGGCATCT
TTTTTGATCATTACACCATCATCAAAAGCATTTGGATAACCATAACATGAAAATTACCATCATTGAGCC
CATAACTTTCCTAAGACAAGGGTGACAATTTGAAACATCAAAGAACCTTACCCAGGGAATTCAAGAAGT
GAGAAGAGTGAATCAGATTCTCCCAGATTAACAACCCCATGTTGGATCCAATCAACCTCTGGATTACAA</u>
AATTTGTGAAAGATTGACTGGTATTCTTAACTATGTTGCTCCTTTTACGCTATGTGGATACGCTGCTTT
```

| Material and Methods |
|---|
| AATGCCTTTGTATCATGCTATTGCTTCCCGTATGGCTTTCATTTTCTCCTCCTTGTATAAATCCTGGTT
GCTGTCTCTTTATGAGGAGTTGTGGCCCGTTGTCAGGCAACGTGGCGTGGTGTGCACTGTGTTTGCTGA
CGCAACCCCCACTGGTTGGGGCATTGCCACCACCTGTCAGCTCCTTTCCGGGACTTTCGCTTTCCCCCT
CCCTATTGCCACGGCGGAACTCATCGCCGCCTGCCTTGCCCGCTGCTGGACAGGGGCTCGGCTGTTGGG
CACTGACAATTCCGTGGTGTTGTCGGGGAAGCTGACGTCCTTTCCATGGCTGCTCGCCTGTGTTGCCAC
CTGGATTCTGCGCGGGACGTCCTTCTGCTACGTCCCTTCGGCCCTCAATCCAGCGGACCTTCCTTCCCG
CGGCCTGCTGCCGGCTCTGCGGCCTCTTCCGCGTCTTCGAGATCTGCCTCGACTGTGCCTTCTAGTTGC
CAGCCATCTGTTGTTTGCCCCTCCCCCGTGCCTTCCTTGACCCTGGAAGGTGCCACTCCCACTGTCCTT
TCCTAATAAAATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGCTGGGGACTCGAGTTAAGGGCGA
ATTCCCGATTAGGATCTTCCTAGAGCATGGCTACGTAGATAAGTAGCATGGCGGGTTAATCATTAACTA
CAAGGAACCCCTAGTGATGGAGTTGGCCACTCCCTCTCTGCGCGCTCGCTCGCTCACTGAGGCCGGGCG
ACCAAAGGTCGCCCGACGCCCGGGCTTTGCCCGGGCGGCCTCAGTGAGCGAGCGAGCGCGCAGCCTTAA
TTAACCTAATTCACTGGCCGTCGTTTTACAACGTCGTGACTGGGAAAACCCTGGCGTTACCCAACTTAA
TCGCCTTGCAGCACATCCCCCTTTCGCCAGCTGGCGTAATAGCGAAGAGGCCCGCACCGATCGCCCTTC
CCAACAGTTGCGCAGCCTGAATGGCGAATGGGACGCGCCCTGTAGCGGCGCATTAAGCGCGGCGGGTGT
GGTGGTTACGCGCAGCGTGACCGCTACACTTGCCAGCGCCCTAGCGCCCGCTCCTTTCGCTTTCTTCCC
TTCCTTTCTCGCCACGTTCGCCGGCTTTCCCCGTCAAGCTCTAAATCGGGGGCTCCCTTTAGGGTTCCG
ATTTAGTGCTTTACGGCACCTCGACCCCAAAAAACTTGATTAGGGTGATGGTTCACGTAGTGGGCCATC
GCCCCGATAGACGGTTTTTCGCCCTTTGACGCTGGAGTTCACGTTCGCCAATAGTGGACTCTTGTTCCA
AACTGGAACAACACTCAACCCTATCTCGGTCTATTCTTTTGATTTATAAGGGATTTTTCCGATTTCGGC
CTATTGGTTAAAAAATGAGCTGATTTAACAAAAATTTAACGCGAATTTTAACAAAATATTAACGTTTAT
AATTTCAGGTGGCATCTTTCGGGGAAATGTGCGCGGAACCCCTATTTGTTTATTTTTCTAAATACATTC
AAATATGTATCCGCTCATGAGACAATAACCCTGATAAATGCTTCAATAATATTGAAAAAGGAAGAGTAT
GAGTATTCAACATTTCCGTGTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCACGAGTGGGTTACATCGAACT
GGATCTCAATAGTGGTAAGATCCTTGAGAGTTTTCGCCCCGAAGAACGTTTTCCAATGATGAGCACTTT
TAAAGTTCTGCTATGTGGCGCGGTATTATCCCGTATTGACGCCGGGCAAGAGCAACTCGGTCGCCGCAT
ACACTATTCTCAGAATGACTTGGTTGAGTACTCACCAGTCACAGAAAAGCATCTTACGGATGGCATGAC
AGTAAGAGAATTATGCAGTGCTGCCATAACCATGAGTGATAACACTGCGGCCAACTTACTTCTGACAAC
GATCGGAGGACCGAAGGAGCTAACCGCTTTTTTGCACAACATGGGGGATCATGTAACTCGCCTTGATCG
TTGGGAACCGGAGCTGAATGAAGCCATACCAAACGACGAGCGTGACACCACGATGCCTGTAGTAATGGT
AACAACGTTGCGCAAACTATTAACTGGCGAACTACTTACTCTAGCTTCCCGGCAACAATTAATAGACTG
GATGGAGGCGGATAAAGTTGCAGGACCACTTCTGCGCTCGGCCCTTCCGGCTGGCTGGTTTATTGCTGA
TAAATCTGGAGCCGGTGAGCGTGGGTCTCGCGGTATCATTGCAGCACTGGGGCCAGATGGTAAGCCCTC
CCGTATCGTAGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACTTTAGATTGA
TTTAAAACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAGAGCGCAGATACCAAATAC
TGTCCTTCTAGTGTAGCCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGTGCACACAGCCCAGCTTGGA
GCGAACGACCTACACCGAACTGAGATACCTACAGCGTGAGCTATGAGAAAGCGCCACGCTTCCCGAAGG
GAGAAAGGCGGACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCGATTTTTGTG
ATGCTCGTCAGGGGGCGGAGCCTATGGAAAAACGCCAGCAACGCGGCCTTTTTACGGTTCCTGGCCTT
TTGCTGCGGTTTTGCTCACATGTTCTTTCCTGCGTTATCCCCTGATTCTGTGGATAACCGTATTACCGC
CTTTGAGTGAGCTGATACCGCTCGCCGCAGCCGAACGACCGAGCGCAGCGAGTCAGTGAGCGAGGAAGC
GGAAG | pAAV.RHO.premiR211
underscore sequence is the sequence of the pre-miR211
SEQ ID NO: 13

AGCGCCCAATACGCAAACCGCCTCTCCCCGCGCGTTGGCGATTCATTAATGCAGCTGGCACGACAGGT
TTCCCGACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACACAG
GAAACAGCTATGACCATGATTACGCCAGATTTAATTAAGGCTGCGCGCTCGCTCGCTCACTGAGGCCGC
CCGGGCAAAGCCCGGGCGTCGGGCGACCTTTGGTCGCCCGGCCTCAGTGAGCGAGCGAGCGCGCAGAGA
GGGAGTGGCCAACTCCATCACTAGGGGTTCCTTGTAGTTAATGATTAACCTGCATGCTACTTATCTAC
GTAGCCATGCTCTAGGAAGATCGGAATTCGCCCTTAAGCTAGCAGATCTTCCCCACCTAGCCACCTGGC
AAACTGCTCCTTCTCTCAAAGGCCCAAACATGGCCTCCCAGACTGCAACCCCAGGCAGTCAGGCCCTG
TCTCCACAACCTCACAGCCACCCTGGACGGAATCTGCTTCTTCCCACATTTGAGTCCTCCTCAGCCCCT
GAGCTCCTCTGGGCAGGGCTGTTTCTTTCCATCTTTGTATTCCCAGGGGCCTGCAAATAAATGTTTAAT
GAACGAACAAGAGAGTGAATTCCAATTCCATGCAACAAGGATTGGGCTCCTGGGCCCTAGGCTATGTGT
CTGGCACCAGAAACGGAAGCTGCAGGTTGCAGCCCCTGCCCTCATGGAGCTCCTCCTGTCAGAGGAGTG
TGGGGACTGGATGACTCCAGAGGTAACTTGTGGGGAACGAACAGGTAAGGGGCTGTGTGACGAGATGA
GAGACTGGGAGAATAAACCAGAAAGTCTCTAGCTGTCCAGAGGACATAGCACAGAGGCCCATGGTCCCT
ATTTCAAACCCAGGCCACCAGACTGAGCTGGGACCTTGGGACAGACAAGTCATGCAGAAGTTAGGGGAC
CTTCTCCTCCCTTTTCCTGGATCTGAGTACCTCTCCTCCCTGACCTCAGGCTTCCTCCTAGTGTCACC
TTGGCCCCTCTTAGAAGCCAATTAGGCCCTCAGTTTCTGCAGCGGGGATTAATATGATTATGAACACCC
CCAATCTCCCAGATGCTGATTCAGCCAGGAGCTTAGGAGGGGAGGTCACTTTATAAGGGTCTGGGGGG
GTCAGAACCCAGAGTCATCCGCTGAATTCTGCAGATATCCATCACACTGGCGGCCGCTCGACCATGC
AATCACAGGTGTGGGGCATCCACTAGAGTGTGGTCAACCTATCAGGGCCGCACACTTAAAAAAAAAAA
CTGACTCCCTTCCCACAGAAGGGAATTTGTCAACTCCTCCCCACCCTCATGCTGGAATACTGACCGGCT
TGATCCTGTGCAGCCAGCCACACTGTGAGTTCATGAGTGCGGAGGTCCTAAGAATCAGATCTTGGTGGA

| Material and Methods |
|---|
| TAAATCAGTTTGATTTAGTGTTTTGGACTTGTAAATTCTGCTTGGACCTGTGACCTGTGGGCTTCCCT |
| TTGTCATCCTTTGCCTAGGCCTCTGAGTGAGGCAAGGACAGCAAAGGGGGGCTCAGTGGTCACCTCTAC |
| TGCAGAGAGTTCAGAAGCCTAGCCTGAGCCAAGAGCAAGTTCTTCTCTGCTTCTGGAAATGAAGTCGCC |
| ATGATCCTGACGATGTAAAAATCCCAAGCACGCTTGGATGGAAATCTCAGAGACAGACGATGCCACCCT |
| GATCCATTGGATCCAATCAACCTCTGGATTACAAAATTTGTGAAAGATTGACTGGTATTCTTAACTATG |
| TTGCTCCTTTTACGCTATGTGGATACGCTGCTTTAATGCCTTTGTATCATGCTATTGCTTCCCGTATGG |
| CTTTCATTTTCTCCTCCTTGTATAAATCCTGGTTGCTGTCTCTTTATGAGGAGTTGTGGCCCGTTGTCA |
| GGCAACGTGGCGTGGTGTGCACTGTGTTTGCTGACGCAACCCCCACTGGTTGGGGCATTGCCACCACCT |
| GTCAGCTCCTTTCCGGGACTTTCGCTTTCCCCCTCCCTATTGCCACGGCGGAACTCATCGCCGCCTGCC |
| TTGCCCGCTGCTGGACAGGGGCTCGGCTGTTGGGCACTGACAATTCCGTGGTGTTGTCGGGGAAGCTGA |
| CGTCCTTTCCATGGCTGCTCGCCTGTGTTGCCACCTGGATTCTGCGCGGGACGTCCTTCTGCTACGTCC |
| CTTCGGCCCTCAATCCAGCGGACCTTCCTTCCCGCGGCCTGCTGCCGGCTCTGCGGCCTCTTCCGCGTC |
| TTCGAGATCTGCCTCGACTGTGCCTTCTAGTTGCCAGCCATCTGTTGTTTGCCCCTCCCCCGTGCCTTC |
| CTTGACCCTGGAAGGTGCCACTCCCACTGTCCTTTCCTAATAAAATGAGGAAATTGCATCGCATTGTCT |
| GAGTAGGTGTCATTCTATTCTGGGGGGTGGGGTGGGGCAGGACAGCAAGGGGGAGGATTGGGAAGACAA |
| TAGCAGGCATGCTGGGGACTCGAGTTAAGGGCGAATTCCCGATTAGGATCTTCCTAGAGCATGGCTACG |
| TAGATAAGTAGCATGGCGGGTTAATCATTAACTACAAGGAACCCTAGTGATGGAGTTGGCCACTCCCT |
| CTCTGCGCGCTCGCTCGCTCACTGAGGCCGGGCGACCAAAGGTCGCCCGACGCCCGGGCTTTGCCCGGG |
| CGGCCTCAGTGAGCGAGCGAGCGCGCAGCCTTAATTAACCTAATTCACTGGCCGTCGTTTTACAACGTC |
| GTGACTGGGAAAACCCTGGCGTTACCCAACTTAATCGCCTTGCAGCACATCCCCTTTCGCCAGCTGGC |
| GTAATAGCGAAGAGGCCCGCACCGATCGCCCTTCCCAACAGTTGCGCAGCCTGAATGGCGAATGGGACG |
| CGCCCTGTAGCGGCGCATTAAGCGCGGCGGGTGTGGTGGTTACGCGCAGCGTGACCGCTACACTTGCCA |
| GCGCCCTAGCGCCCGCTCCTTTCGCTTTCTTCCCTTCCTTTCTCGCCACGTTCGCCGGCTTTCCCCGTC |
| AAGCTCTAAATCGGGGGCTCCCTTTAGGGTTCCGATTTAGTGCTTTACGGCACCTCGACCCCAAAAAAC |
| TTGATTAGGGTGATGGTTCACGTAGTGGGCCATCGCCCCGATAGACGGTTTTTCGCCCTTTGACGCTGG |
| AGTTCACGTTCCTCAATAGTGGACTCTTGTTCCAAACTGGAACAACACTCAACCCTATCTCGGTCTATT |
| CTTTTGATTTATAAGGGATTTTTCCGATTTCGGCCTATTGGTTAAAAAATGAGCTGATTTAACAAAAAT |
| TTAACGCGAATTTTAACAAAATATTAACGTTTATAATTTCAGGTGGCATCTTTCGGGGAAATGTGCGCG |
| GAACCCCTATTTGTTTATTTTTCTAAATACATTCAAATATGTATCCGCTCATGAGACAATAACCCTGAT |
| AAATGCTTCAATAATATTGAAAAAGGAAGAGTATGAGTATTCAACATTTCCGTGTCGCCCTTATTCCCT |
| TTTTTGCGGCATTTTGCCTTCCTGTTTTTGCTCACCCAGAAACGCTGGTGAAAGTAAAAGATGCTGAAG |
| ATCAGTTGGGTGCACGAGTGGGTTACATCGAACTGGATCTCAATAGTGGTAAGATCCTTGAGAGTTTTC |
| GCCCCGAAGAACGTTTTCCAATGATGAGCACTTTTAAAGTTCTGCTATGTGGCGCGGTATTATCCCGTA |
| TTGACGCCGGGCAAGAGCAACTCGGTCGCCGCATACACTATTCTCAGAATGACTTGGTTGAGTACTCAC |
| CAGTCACAGAAAAGCATCTTACGGATGGCATGACAGTAAGAGAATTATGCAGTGCTGCCATAACCATGA |
| GTGATAACACTGCGGCCAACTTACTTCTGACAACGATCGGAGGACCGAAGGAGCTAACCGCTTTTTTGC |
| ACAACATGGGGGATCATGTAACTCGCCTTGATCGTTGGGAACCGGAGCTGAATGAAGCCATACCAAACG |
| ACGAGCGTGACACCACGATGCCTGTAGTAATGGTAACAACGTTGCGCAAACTATTAACTGGCGAACTAC |
| TTACTCTAGCTTCCCGGCAACAATTAATAGACTGGATGGAGGCGGATAAAGTTGCAGGACCACTTCTGC |
| GCTCGGCCCTTCCGGCTGGCTGGTTTATTGCTGATAAATCTGGAGCCGGTGAGCGTGGGTCTCGCGGTA |
| TCATTGCAGCACTGGGGCCAGATGGTAAGCCCTCCCGTATCGTAGTTATCTACACGACGGGGAGTCAGG |
| CAACTATGGATGAACGAAATAGACAGATCGCTGAGATAGGTGCCTCACTGATTAAGCATTGGTAACTGT |
| CAGACCAAGTTTACTCATATATACTTTAGATTGATTTAAAACTTCATTTTTAATTTAAAAGGATCTAGG |
| TGAAGATCCTTTTTGATAATCTCATGACCAAAATCCCTTAACGTGAGTTTTCGTTCCACTGAGCGTCAG |
| ACCCCGTAGAAAAGATCAAAGGATCTTCTTGAGATCCTTTTTTTCTGCGCGTAATCTGCTGCTTGCAAA |
| CAAAAAAACCACCGCTACCAGCGGTGGTTTGTTTGCCGGATCAAGAGCTACCAACTCTTTTTCCGAAGG |
| TAACTGGCTTCAGCAGAGCGCAGATACCAAATACTGTCCTTCTAGTGTAGCCGTAGTTAGGCCACCACT |
| TCAAGAACTCTGTAGCACCGCCTACATACCTCGCTCTGCTAATCCTGTTACCAGTGGCTGCTGCCAGTG |
| GCGATAAGTCGTGTCTTACCGGGTTGGACTCAAGACGATAGTTACCGGATAAGGCGCAGCGGTCGGGCT |
| GAACGGGGGGTTCGTGCACACAGCCCAGCTTGGAGCGAACGACCTACACCGAACTGAGATACCTACAGCG |
| TGAGCTATGAGAAAGCGCCACGCTTCCCGAAGGGAGAAAGGCGGACAGGTATCCGGTAAGCGGCAGGGT |
| CGGAACAGGAGAGCGCACGAGGGAGCTTCCAGGGGGAAAGCCTGGTATCTTTATAGTCCTGTCGGGTT |
| TCGCCACCTCTGACTTGAGCGTCGATTTTTGTGATGCTCGTCAGGGGGGCGGAGCCTATGGAAAAACGC |
| CAGCAACGCGGCCTTTTTACGGTTCCTGGCCTTTTGCTGCGGTTTTGCTCACATGTTCTTTCCTGCGTT |
| ATCCCCTGATTCTGTGGATAACCGTATTACCGCCTTTGAGTGAGCTGATACCGCTCGCCGCAGCCGAAC |
| GACCGAGCGCAGCGAGTCAGTGAGCGAGGAAGCGGAAG | pAAV.RHO.EGFP

SEQ ID NO: 14

| |
|---|
| AGCGCCCAATACGCAAACCGCCTCTCCCCGCGCGTTGGCCGATTCATTAATGCAGCTGGCACGACAGGT |
| TTCCCGACTGGAAAGCGGGCAGTGAGCGCAACGCAATTAATGTGAGTTAGCTCACTCATTAGGCACCCC |
| AGGCTTTACACTTTATGCTTCCGGCTCGTATGTTGTGTGGAATTGTGAGCGGATAACAATTTCACACAG |
| GAAACAGCTATGACCATGATTACGCCAGATTTAATTAAGGCTGCGCGCTCGCTCGCTCACTGAGGCCGC |
| CCGGGCAAAGCCCGGGCGTCGGGCGACCTTTGGTCGCCCGGCCTCAGTGAGCGAGCGAGCGCGCAGAGA |
| GGGAGTGGCCAACTCCATCACTAGGGGTTCCTTGTAGTTAATGATTAACCCGCCATGCTACTTATCTAC |
| GTAGCCATGCTCTAGGAAGATCGGAATTCGCCCTTAAGCTAGCAGATCTTCCCCACCTAGCCACCTGGC |
| AAACTGCTCCTTTCTCTCAAAGGCCCAAACATGGCCTCCCAGACTGCAACCCCCAGGCAGTCAGGCCCTG |
| TCTCCACAACCTCACAGCCACCCTGGACGGAATCTGCTTCTTCCCACATTTGAGTCCTCCTCAGCCCCT |
| GAGCTCCTCTGGGCAGGGCTGTTTCTTTCCATCTTTGTATTCCCAGGGGCCTGCAAATAAATGTTTAAT |
| GAACGAACAAGAGAGTGAATTCCAATTCCATGCAACAAGGATTGGGCTCCTGGGCCCTAGGCTATGTGT |
| CTGGCACCAGAAACGGAAGCTGCAGGTTGCAGCCCCTGCCCTCATGGAGGTCCTCCTGTCAGGAGGTG |
| TGGGGACTGGATGACTCCAGAGGTAACTTGTGGGGGAACGAACAGGTAAGGGCTGTGTGACGAGATGA |
| GAGACTGGAGAATAAACCAGAAAGTCTCTAGCTGTCCAGAGGACATAGCACAGAGGCCCATGGTCCCT |
| ATTTCAAACCCAGGCCACCAGACTGAGCTGGGACCTTGGGACAGACAAGTCATGCAGAAGTTAGGGGAC |
| CTTCTCCTCCCTTTTCCTGGATCCTGAGTACCTCTCCTCCCTGACCTCAGGCTTCCTCCTAGTGTCACC |
| TTGGCCCCTCTTAGAAGCCAATTAGGCCCTCAGTTTCTGCAGCGGGATTAATATGATTATGAACACCC |
| CCAATCTCCCAGATGCTGATTCAGCCAGGAGCTTAGGAGGGGAGGTCACTTTATAAGGGTCTGGGGGG |

| Material and Methods |
|---|
| GTCAGAACCCAGAGTCATCCGCCTGAATTCTGCAGATATCCATCACACTGGCGGCCGCCATGGTGAGCA
AGGGCGAGGAGCTGTTCACCGGGGTGGTGCCCATCCTGGTCGAGCTGGACGGCGACGTAAACGGCCACA
AGTTCAGCGTGTCCGGCGAGGGCGAGGGCGATGCCACCTACGGCAAGCTGACCCTGAAGTTCATCTGCA
CCACCGGCAAGCTGCCCGTGCCCTGGCCCACCCTCGTGACCACCCTGACCTACGGCGTGCAGTGCTTCA
GCCGCTACCCCGACCACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTGGGGCACAAGC
TGGAGTACAACTACAACAGCCACAACGTCTATATCATGGCCGACAAGCAGAAGAACGGCATCAAGGTGA
ACTTCAAGATCCGCCACAACATCGAGGACGGCAGCGTGCAGCTCGCCGACCACTACCAGCAGAACACCC
CCATCGGCGACGGCCCCGTGCTGCTGCCCGACAACCACTACCTGAGCACCCAGTCCGCCCTGAGCAAAG
ACCCCAACGAGAAGCGCGATCACATGGTCCTGCTGGAGTTCGTGACCGCCGCCGGGATCACTCTCGGCA
TGGACGAGCTGTACAAGTAATAAGCTTGGATCCAATCAACCTCTGGATTACAAAATTTGTGAAAGATTG
ACTGGTATTCTTAACTATGTTGCTCCTTTTACGCTATGTGGATACGCTGCTTTAATGCCTTTGTATCAT
GCTATTGCTTCCCGTATGGCTTTCATTTTCTCCTCCTTGTATAAATCCTGGTTGCTGTCTCTTTATGAG
GAGTTGTGGCCCGTTGTCAGGCAACGTGGCGTGGTGTGCACTGTGTTTGCTGACGCAACCCCCACTGGT
TGGGGCATTGCCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGACAATTCCGTG
GTGTTGTCGGGGAAATCATCGTCCTTTCCTTGGCTGCTCGCCTGTGTTGCCACCTGGATTCTGCGCGGG
ACGTCCTTCTGCTACGTCCCTTCGGCCCTCAATCCAGCGGACCTTCCTTCCCGCGGCCTGCTGCCGGCT
CTGCGGCCTCTTCCGCGTCTTCGAGATCTGCCTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATAAAATGAGG
AAATTGCATCGCATTGTCTGAGTAGGTGTCATTCTATTCTGGGGGGTGGGGTGGGGCAGGACAGCAAGG
GGGAGGATTGGGAAGACAATAGCAGGCATGCTGGGGACTCGAGTTAAGGGCGAATTCCCGATTAGGATC
TTCCTAGAGCATGGCTACGTAGATAAGTAGCATGGCGGGTTAATCATTAACTACAAGGAACCCCTAGTG
ATGGAGTTGGCCACTCCCTCTCTGCGCGCTCGCTCGCTCACTGAGGCCGGGCGACCAAAGGTCGCCCGA
CGCCCGGGCTTTGCCCGGGCGGCCTCAGTGAGCGAGCGAGCGCGCAGCCTTAATTAACCTAATTCACTG
GCCGTCGTTTTACAACGTCGTGACTGGGAAAACCCTGGCGTTACCCAACTTAATCGCCTTGCAGCACAT
CCCCCTTTCGCCAGCTGGCGTAATAGCGAAGAGGCCCGCACCGATCGCCCTTCCCAACAGTTGCGCAGC
CTGAATGGCGAATGGGACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCCTTTCTCGCCACG
TTCGCCGGCTTTCCCCGTCAAGCTCTAAATCGGGGGCTCCCTTTAGGGTTCCGATTTAGTGCTTTACGG
CACCTCGACCCCAAAAAACTTGATTAGGGTGATGGTTCACGTAGTGGGCCATCGCCCTGATAGACGGTT
TTTCGCCCTTTGACGCTGGAGTTCACGTTCCTCAATAGTGGACTCTTGTTCCAAACTGGAACAACACTC
AACCCTATCTCGGTCTATTCTTTTGATTTATAAGGGATTTTCCGATTTCGGCCTATTGGTTAAAAAAT
GAGCTGATTTAACAAAAATTTAACGCGAATTTTAACAAAATATTAACGTTTATAATTTCAGGTGGCATC
TTTCGGGGAAATGTGCGCGGAACCCCTATTTGTTTATTTTTCTAAATACATTCAAATATGTATCCGCTC
ATGAGACAATAACCCTGATAAATGCTTCAATAATATTGAAAAAGGAAGAGTATGAGTATTCAACATTTC
CGTGTCGCCCTTATTCCCTTTTTTGCGGCATTTTGCCTTCCTGTTTTTGCTCACCCAGAAACGCTGGTG
AAAGTAAAAGATGCTGAAGATCAGTTGGGTGCACGAGTGGGTTACATCGAACTGGATCTCAATAGTGGT
AAGATCCTTGAGAGTTTTCGCCCCGAAGAACGTTTTCCAATGATGAGCACTTTTAAAGTTCTGCTATGT
GGCGCGGTATTATCCCGTATTGACGCCGGGCAAGAGCAACTCGGTCGCCGCATACACTATTCTCAGAAT
GACTTGGTTGAGTACTCACCAGTCACAGAAAAGCATCTTACGGATGGCATGACAGTAAGAGAATTATGC
AGTGCTGCCATAACCATGAGTGATAACACTGCGGCCAACTTACTTCTGACAACGATCGGAGGACCGAAG
GAGCTAACCGCTTTTTTGCACAACATGGGGGATCATGTAACTCGCCTTGATCGTTGGGAACCGGAGCTG
AATGAAGCCATACCAAACGACGAGCGTGACACCACGATGCCTGTAGTAATGGTAACAACGTTGCGCAAA
CTATTAACTGGCGAACTACTTACTCTAGCTTCCCGGCAACAATTAATAGACTGGATGGAGGCGGATAAA
GTTGCAGGACCACTTCTGCGCTCGGCCCTTCCGGCTGGCTGGTTTATTGCTGATAAATCTGGAGCCGGT
GAGCGTGGGTCTCGCGGTATCATTGCAGCACTGGGGCCAGATGGTAAGCCCTCCCGTATCGTAGTTATC
TACACGACGGGGAGTCAGGCAACTATGGATGAACGAAATAGACAGATCGCTGAGATAGGTGCCTCACTG
ATTAAGCATTGGTAACTGTCAGACCAAGTTTACTCATATATACTTTAGATTGATTTAAAACTTCATTTT
TAATTTAAAAGGATCTAGGTGAAGATCCTTTTTGATAATCTCATGACCAAAATCCCTTAACGTGAGTTT
TCGTTCCACTGAGCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTTCTAGTGTAG
CCGTAGTTAGGCCACCACTTCAAGAACTCTGTAGCACCGCCTACATACCTCGCTCTGCTAATCCTGTTA
CCAGTGGCTGCTGCCAGTGGCGATAAGTCGTGTCTTACCGGGTTGGACTCAAGACGATAGTTACCGGAT
AAGGCGCAGCGGTCGGGCTGAACGGGGGGTTCGTGCACACAGCCCAGCTTGGAGCGAACGACCTACACC
GAACTGAGATACCTACAGCGTGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCGTCAGGGGGG
CGGAGCCTATGGAAAAACGCCAGCAACGCGGCCTTTTTACGGTTCCTGGCCTTTTGCTGCGGTTTTGCT
CACATGTTCTTTCCTGCGTTATCCCCTGATTCTGTGGATAACCGTATTACCGCCTTTGAGTGAGCTGAT
ACCGCTCGCCGCAGCCGAACGACCGAGCGCAGCGAGTCAGTGAGCGAGGAAGCGGAAG | pAAV 2.1 CMV hAIPL1 (bold CMV promoter; double underscore <u>hAIPL1 cds</u>)

SEQ ID NO: 15

AGCGCCCAATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACACAG
GAAACAGCTATGACCATGATTACGCCAGATTTAATTAAGGCTGCGCGCTCGCTCGCTCACTGAGGCCGC
CCGGGCAAAGCCCGGGCGTCGGGCGACCTTTGGTCGCCCGGCCTCAGTGAGCGAGCGAGCGCGCAGAGA
GGGAGTGGCCAACTCCATCACTAGGGGTTCCTTGTAGTTAATGATTAACCCGCCATGCTACTTATCTAC
GTAGCCATGCTCTAGGAAGATCGGAATTCGCCCTTAAGCTAGCTAGT**TATTAATAGTAATCAATTACGG
GGTCATTAGTTCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGTACATCAAGTGTATC
ATATGCCAAGTACGCCCCCTATTGACGTCAATGACGGTAAATGGCCCGCCTGGCATTATGCCCAGTACA**

Material and Methods

```
TGACCTTATGGGACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAAGTCTCCACCCCA
TTGACGTCAATGGGAGTTTGTTTTGGCACCAAAATCAACGGGACTTTCCAAAATGTCGTAACAACTCCG
CCCCATTGACGCAAATGGGCGGTAGGCGTGTACGGTGGGAGGTCTATATAAGCAGAGCTGGTTTAGTGA
ACCGTCAGATCCTGCAGAAGTTGGTCGTGAGGCACTGGGCAGGTAAGTATCAAGGTTACAAGACAGGTT
TAAGGAGACCAATAGAAACTGGGCTTGTCGAGACAGAGAAGACTCTTGCGTTTCTGATAGGCACCTATT
GGTCTTACTGACATCCACTTTGCCTTTCTCTCCACAGGTGTCCAGGCGGCCGCCATGGATGCCGCTCTG
CTCCTGAACGTGGAAGGGGTCAAGAAAACCATTCTGCACGGGGGCACGGGCGAGCTCCCAAACTTCATC
ACCGGATCCCGAGTGATCTTTCATTTCCGCACCATGAAATGTGATGAGGAGCGGACAGTCATTGACGAC
AGTCGGCAGGTGGGCCAGCCCATGCACATCATCATCGGAAACATGTTCAAGCTCGAGGTCTGGGAGATC
CTGCTTACCTCCATGCGGGTGCACGAGGTGGCCGAGTTCTGGTGCGACACCATCCACACGGGGGTCTAC
CCCATCCTATCCCGGAGCCTGAGGCAGATGGCCCAGGGCAAGGACCCCACAGAGTGGCACGTGCACACG
TGCGGGCTGGCCAACATGTTCGCCTACCACACGTGGGCTACGAGGACCTGGACGAGCTGCAGAAGGAG
CCTCAGCCTCTGGTCTTTGTGATCGAGCTGCTGCAGGTTGATGCCCCGAGTGATTACCAGAGGGAGACC
TGGAACCTGAGCAATCATGAGAAGATGAAGGCGGTGCCCGTCCTCCACGGAGAGGGAAATCGGCTCTTC
AAGCTGGGCCGCTACGAGGAGGCCTCTTCCAAGTACCAGGAGGCCATCATCTGCCTAAGGAACCTGCAG
ACCAAGGAGAAGCCATGGGAGGTGCAGTGGCTGAAGCTGGAGAAGATGATCAATACTCTGATCCTCAAC
TACTGCCAGTGCCTGCTGAAGAAGGAGGAGTACTATGAGGTGCTGGAGCACACCAGTGATATTCTCCGG
CACCACCCAGGCATCGTGAAGGCCTACTACGTGCGTGCCCGGCTCACGCAGAGGTGTGGAATGAGGCC
GAGGCCAAGGCGGACCTCCAGAAAGTGCTGGAGCTGGAGCCGTCATGCAGAAGGCGGTGCGCAGGGAG
CTGAGGCTGCTGGAGAACCGCATGGCGGAGAAGCAGGAGGAGGAGCGGCTGCGCTGCCGAACATGCTG
AGCCAGGGTGCCACGCAGCCTCCCGCAGAGCCACCCACAGAGCCACCCGCACAGTCATCCACAGAGCCA
CCTGCAGAGCCACCCACTGACCATCTGCAGAGCTGTCCGCAGGGCCCCCTGCAGAGCCAGCCACAGAGC
CACCCCCGTCCCCAGGGCACTCGCTGCAGCACTGAAAGCTTGGATCCAATCAACCTCTGGATTACAAAA
TTTGTGAAAGATTGACTGGTATTCTTAACTATGTTGCTCCTTTTACGCTATGTGGATACGCTGCTTTAA
TGCCTTTGTATCATGCTATTGCTTCCCGTATGGCTTTCATTTTCTCCTCCTTGTATAAATCCTGGTTGC
TGTCTCTTTATGAGGAGTTGTGGCCCGTTGTCAGGCAACGTGGCGTGGTGTGCACTGTGTTTGCTGACG
CAACCCCCACTGGTTGGGGCATTGCCACCACCTGTCAGCTCCTTTCCGGGACTTTCGCTTTCCCCCTCC
CTATTGCCACGCGGAACTCATCGCCGCCTGCCTTGCCCGCTGCTGGACAGGGGCTCGGCTGTTGGGCA
CTGACAATTCCGTGGTGTTGTCGGGGAAGCTGACGTCCTTTCCATGGCTGCTCGCCTGTGTTGCCACCT
GGATTCTGCGCGGGACGTCCTTCTGCTACGTCCCTTCGGCCCTCAATCCAGCGGACCTTCCTTCCCGCG
GCCTGCTGCCGGCTCTGCGGCCTCTTCCCGCGTCTTCGAGATCTGCCTCGACTGTGCCTTCTAGTTGCCA
GCCATCTGTTGTTTGCCCCTCCCCCGTGCCTTCCTTGACCCTGGAAGGTGCCACTCCCACTGTCCTTTC
CTAATAAAATGAGGAAATTGCATCGCATTGTCTGAGTAGGTGTCATTCTATTCTGGGGGGTGGGGTGGG
GCAGGACAGCAAGGGGGAGGATTGGGAAGACAATAGCAGGCATGCTGGGGACTCGAGTTAAGGGCGAAT
TCCCGATTAGGATCTTCCTAGAGCATGGCTACGTAGATAAGTAGCATGGCGGGTTAATCATTAACTACA
AGGAACCCCTAGTGATGGAGTTGGCCACTCCCTCTCTGCGCGCTCGCTCGCTCACTGAGGCCGGGCGAC
CAAAGGTCGCCCGACGCCCGGGCTTTGCCCGGGCGGCCTCAGTGAGCGAGCGAGCGCGCAGCCTTAATT
AACCTAATTCACTGGCCGTCGTTTTACAACGTCGTGACTGGGAAAACCCTGGCGTTACCCAACTTAATC
GCCTTGCAGCACATCCCCCTTTCGCCAGCTGGCGTAATAGCGAAGAGGCCCGCACCGATCGCCCTTCCC
AACAGTTGCGCAGCCTGAATGGCGAATGGGACGCGCCCTGTAGCGGCGCATTAAGCGCGGCGGGTGTGG
TGGTTACGCGCAGCGTGACCGCTACACTTGCCAGCGCCCTAGCGCCCGCTCCTTTCGCTTTCTTCCCTT
CCTTTCTCGCCACGTTCGCCGGCTTTCCCCGTCAAGCTCTAAATCGGGGGCTCCCTTTAGGGTTCCGAT
TTAGTGCTTTACGGCACCTCGACCCCAAAAAACTTGATTAGGGTGATGGTTCACGTAGTGGGCCATCGC
CCCGATAGACGGTTTTTCGCCCTTTGACGCTGGAGTTCACGTTCCTCAATAGTGGACTCTTGTTCCAAA
CTGGAACAACACTCAACCCTATCTCGGTCTATTCTTTTGATTTATAAGGGATTTTTCCGATTTCGGCCT
ATTGGTTAAAAAATGAGCTGATTTAACAAAAATTTAACGCGAATTTTAACAAAATATTAACGTTTATAA
TTTCAGGTGGCATCTTTCGGGGAAATGTGCGCGGAACCCCTATTTGTTTATTTTTCTAAATACATTCAA
ATATGTATCCGCTCATGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTGTTTTTGCTCACC
CAGAAACGCTGGTGAAAGTAAAAGATGCTGAAGATCAGTTGGGTGCACGAGTGGGTTACATCGAACTGG
ATCTCAATAGTGGTAAGATCCTTGAGAGTTTTCGCCCCGAAGAACGTTTTCCAATGATGAGCACTTTTA
AAGTTCTGCTATGTGGCGCGGTATTATCCCGTATTGACGCCGGGCAAGAGCAACTCGGTCGCCGCATAC
ACTATTCTCAGAATGACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACTTACTTCTGACAACGA
TCGGAGGACCGAAGGAGCTAACCGCTTTTTTGCACAACATGGGGGATCATGTAACTCGCCTTGATCGTT
GGGAACCGGAGCTGAATGAAGCCATACCAAACGACGAGCGTGACACCACGATGCCTGTAGTAATGGTAA
CAACGTTGCGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTATTGCTGATA
AATCTGGAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGATCGCTTGA
GATAGGTGCCTCACTGATTAAGCATTGGTAACTGTCAGACCAAGTTTACTCATATATACTTTAGATTGA
TTTAAAACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAGAGCGCAGATACCAAATAC
TGTCCTTCTAGTGTAGCCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGTGCACACAGCCCAGCTTGGA
GCGAACGACCTACACCGAACTGAGATACCTACAGCGTGAGCTATGAGAAAGCGCCACGCTTCCCGAAGG
GAGAAAGGCGGACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCGATTTTTGTG
ATGCTCGTCAGGGGGCGGAGCCTATGGAAAAACGCCAGCAACGCGGCCTTTTTACGGTTCCTGGCCTT
```

Material and Methods

TTGCTGCGGTTTTGCTCACATGTTCTTTCCTGCGTTATCCCCTGATTCTGTGGATAACCGTATTACCGC
CTTTGAGTGAGCTGATACCGCTCGCCGCAGCCGAACGACCGAGCGCAGCGAGTCAGTGAGCGAGGAAGC
GGAAG pAAV2.1 CMV-eGFP (CMV promoter; green <u>EGFP_cds</u>)

SEQ ID NO: 16

AGCGCCCAATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACACAG
GAAACAGCTATGACCATGATTACGCCAGATTTAATTAAGGCTGCGCGCTCGCTCGCTCACTGAGGCCGC
CCGGGCAAAGCCCGGGCGTCGGGCGACCTTTGGTCGCCCGGCCTCAGTGAGCGAGCGAGCGCGCAGAGA
GGGAGTGGCCAACTCCATCACTAGGGGTTCCTTGTAGTTAATGATTAACCCGCCATGCTACTTATCTAC
GTAGCCATGCTCTAGGAAGATCGGAATTCGCCCTTAAGCTAGCTAGTTATTAATAGTAATCAATTACGG
GGTCATTAGTTCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGTACATCAAGTGTATC
ATATGCCAAGTACGCCCCCTATTGACGTCAATGACGGTAAATGGCCCGCCTGGCATTATGCCCAGTACA
TGACCTTATGGGACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAAGTCTCCACCCCA
TTGACGTCAATGGGAGTTTGTTTTGGCACCAAAATCAACGGGACTTTCCAAAATGTCGTAACAACTCCG
CCCCATTGACGCAAATGGGCGGTAGGCGTGTACGGTGGGAGGTCTATATAAGCAGAGCTGGTTTAGTGA
ACCGTCAGATCCTGCAGAAGTTGGTCGTGAGGCACTGGGCAGGTAAGTATCAAGGTTACAAGACAGGTT
TAAGGAGACCAATAGAAACTGGGCTTGTCGAGACAGAGAAGACTCTTGCGTTTCTGATAGGCACCTATT
GGTCTTACTGACATCCACTTTGCCTTTCTCTCCACAGGTGTCCAGGCGGCCGC<u>ATGGTGAGCAAGGGC</u>
<u>GAGGAGCTGTTCACCGGGGTGGTGCCCATCCTGGTCGAGCTGGACGGCGACGTAAACGGCCACAAGTTC</u>
<u>AGCGTGTCCGGCGAGGGCGAGGGCGATGCCACCTACGGCAAGCTGACCCTGAAGTTCATCTGCACCACC</u>
<u>GGCAAGCTGCCCGTGCCCTGGCCCACCCTCGTGACCACCCTGACCTACGGCGTGCAGTGCTTCAGCCGC</u>
<u>TACCCCGACCACATGAAGCAGCACGACTTCTTCAAGTCCGCCATGCCCGAAGGCTACGTCCAGGAGCGC</u>
<u>ACCATCTTCTTCAAGGACGACGGCAACTACAAGACCCGCGCCGAGGTGAAGTTCGAGGGCGACACCCTG</u>
<u>GTGAACCGCATCGAGCTGAAGGGCATCGACTTCAAGGAGGACGGCAACATCCTGGGGCACAAGCTGGAG</u>
<u>TACAACTACAACAGCCACAACGTCTATATCATGGCCGACAAGCAGAAGAACGGCATCAAGGTGAACTTC</u>
<u>AAGATCCGCCACAACATCGAGGACGGCAGCGTGCAGCTCGCCGACCACTACCAGCAGAACACCCCCATC</u>
<u>GGCGACGGCCCCGTGCTGCTGCCCGACAACCACTACCTGAGCACCCAGTCCGCCCTGAGCAAAGACCCC</u>
<u>AACGAGAAGCGCGATCACATGGTCCTGCTGGAGTTCGTGACCGCCGCCGGGATCACTCTCGGCATGGAC</u>
<u>GAGCTGTACAAG</u>TAATAAGCTTGGATCCAATCAACCTCTGGATTACAAAATTTGTGAAAGATTGACTGG
TATTCTTAACTATGTTGCTCCTTTTACGCTATGTGGATACGCTGCTTTAATGCCTTTGTATCATGCTAT
TGCTTCCCGTATGGCTTTCATTTTCTCCTCCTTGTATAAATCCTGGTTGCTGTCTCTTTATGAGGAGTT
GTGGCCCGTTGTCAGGCAACGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCCCTATTGCCACGGCGGAACT
CATCGCCGCCTGCCTTGCCCGCTGCTGGACAGGGGCTCGGCTGTTGGGCACTGACAATTCCGTGGTGTT
GTCGGGGAAATCATCGTCCTTTCCTTGGCTGCTCGCCTGTGTTGCCACCTGGATTCTGCGCGGGACGTC
CTTCTGCTACGTCCCTTCGGCCCTCAATCCAGCGGACCTTCCTTCCCGCGGCCTGCTGCCGGCTCTGCG
GCCTCTTCCGCGTCTTCGAGATCTGCCTCGACTGTGCCTTCTAGTTGCCAGCCATCTGTTGTTTGCCCC
TCCCCCGTGCCTTCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGCAGGACAGCAAGGGGGAG
GATTGGGAAGACAATAGCAGGCATGCTGGGGACTCGAGTTAAGGGCGAATTCCCGATTAGGATCTTCCT
AGAGCATGGCTACGTAGATAAGTAGCATGGCGGGTTAATCATTAACTACAAGGAACCCCTAGTGATGGA
GTTGGCCACTCCCTCTCTGCGCGCTCGCTCGCTCACTGAGGCCGGGCGACCAAAGGTCGCCCGACGCCC
GGGCTTTGCCCGGGCGGCCTCAGTGAGCGAGCGAGCGCGCAGCCTTAATTAACCTAATTCACTGGCCGT
CGTTTTACAACGTCGTGACTGGGAAAACCCTGGCGTTACCCAACTTAATCGCCTTGCAGCACATCCCCC
TTTCGCCAGCTGGCGTAATAGCGAAGAGGCCCGCACCGATCGCCCTTCCCAACAGTTGCGCAGCCTGAA
TGGCGAATGGGACGCGCCCTGTAGCGGCGCATTAAGCGCGGCGGGTGTGGTGGTTACGCGCAGCGTGAC
CGCTACACTTGCCAGCGCCCTAGCGCCCGCTCCTTTCGCTTTCTTCCCTTCCTTTCTCGCCACGTTCGC
CGGCTTTCCCCGTCAAGCTCTAAATCGGGGGCTCCCTTTAGGGTTCCGATTTAGTGCTTTACGGCACCTC
GACCCCAAAAACTTGATTAGGGTGATGGTTCACGTAGTGGGCCATCGCCCCGATAGACGGTTTTTCGCC
CTTTGACGCTGGAGTTCACGTTCCTCAATAGTGGACTCTTGTTCCAAACTGGAACAACACTCAACCCTA
TCTCGGTCTATTCTTTTGATTTATAAGGGATTTTCCGATTTCGGCCTATTGGTTAAAAAATGAGCTGA
TTTAACAAAAATTTAACGCGAATTTTAACAAAATATTAACGTTTATAATTTCAGGTGGCATCTTTCGGG
GAAATGTGCGCGGAACCCCTATTTGTTTATTTTTCTAAATACATTCAAATATGTATCCGCTCATGAGAC
AATAACCCTGATAAATGCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAACGCTGGTGAAAGTAA
AAGATGCTGAAGATCAGTTGGGTGCACGAGTGGGTTACATCGAACTGGATCTCAATAGTGGTAAGATCC
TTGAGAGTTTTCGCCCCGAAGAACGTTTTCCAATGATGAGCACTTTTAAAGTTCTGCTATGTGGCGCGG
TATTATCCCGTATTGACGCCGGGCAAGAGCAACTCGGTCGCCGCATACACTATTCTCAGAATGACTTGG
TTGAGTACTCACCAGTCACAGAAAAGCATCTTACGGATGGCATGACAGTAAGAGAATTATGCAGTGCTG
CCATAACCATGAGTGATAACACTGCGGCCAACTTACTTCTGACAACGATCGGAGGACCGAAGGAGCTAA
CCGCTTTTTTGCACAACATGGGGGATCATGTAACTCGCCTTGATCGTTGGGAACCGGAGCTGAATGAAG
CCATACCAAACGACGAGCGTGACACCACGATGCCTGTAGTAATGGTAACAACGTTGCGCAAACTATTAA
CTGGCGAACTACTTACTCTAGCTTCCCGGCAACAATTAATAGACTGGATGGAGGCGGATAAAGTTGCAG
GACCACTTCTGCGCTCGGCCCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGTATCGTAGTTATCTACACGA
CGGGGAGTCAGGCAACTATGGATGAACGAAATAGACAGATCGCTGAGATAGGTGCCTCACTGATTAAGC
ATTGGTAACTGTCAGACCAAGTTTACTCATATATACTTTAGATTGATTTAAAACTTCATTTTTAATTTA
AAAGGATCTAGGTGAAGATCCTTTTTGATAATCTCATGACCAAAATCCCTTAACGTGAGTTTTCGTTCC
ACTGAGCGTCAGACCCCGTAGAAAAGATCAAAGGATCTTCTTGAGATCCTTTTTTTCTGCGCGTAATCT
GCTGCTTGCAAACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTCCTTCTAGTGTAGCCGTAGT

Material and Methods

```
TAGGCCACCACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGGATAAGGCGC
AGCGGTCGGGCTGAACGGGGGGTTCGTGCACAGCCCAGCTTGGCAGCGAACGACCTACACCGAACTGAGA
TACCTACAGCGTAGAGCTATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTTTATAG
TCCTGTCGGGTTTCGCCACCTCTGACTTGAGCGTCGATTTTTGTGATGCTCGTCAGGGGGGAGCCTATG
GAAAAACGCCAGCAACGCGGCCTTTTTACGGTTCCTGGCCTTTTGCTGCGGTTTTGCTCACATGTTCTT
TCCTGCGTTATCCCCTGATTCTGTGGATAACCGTATTACCGCCTTTGAGTGAGCTGATACCGCTCGCCG
CAGCCGAACGACCGAGCGCAGCGAGTCAGTGAGCGAGGAAGCGGAAG
```

Plasmid Construction

Recombinant AAV vectors containing the murine precursor sequence of miR-204 and miR-211 under the cytomegalovirus (CMV) promoter were constructed by a two-step cloning protocol. Initially, the cassettes containing the precursor of miR-204 and miR-211 were amplified from mouse genomic DNA using the following two sets of oligonucleotides: 5'-ATAAGAATGCGGCCGCCTGTTCAGGACT-TGGCTAAG-3' (SEQ ID NO: 17) and 5'-CGCGGATC-CAACATGGGGTTGTTAATCTG-3' (SEQ ID NO: 18) for miR-204; 5'-ATAAGAATGCGGCCGCTCTGACCATG-CAATCACAG-3' (SEQ ID NO: 19) and 5'-CGCGGATC-CAATGGATCAGGGTGGCATC-3' (SEQ ID NO: 20) for miR-211. The obtained amplimers were subcloned in the TOPO® TA Cloning® vector (Invitrogen) and released following digestion with Not I and BamH I. The fragment was then cloned into the Not I-BamH I sites of the pAAV2.1-CMV-EGFP plasmid (25) and used for the production of AAV2/8 vectors.

The vector in which expression of the precursor miR-204 is under the control of a photoreceptor-specific promoter (pAAV.RHO.premiR-204) was generated by exchanging the CMV promoter of pAAV.CMV.premiR204 with the Rhodopsin (RHO) promoter sequence. Briefly, the sequence corresponding to the human Rhodopsin promoter was released from pAAV2.1-RHO-EGFP plasmid (25) by restriction with Nhe I and Not I and was cloned in the pAAV.CMV.premiR204 backbone, previously digested with the same enzymes.

To generate the vectors expressing hAIPL1 (pAAV2.1-CMV-hAIPL1), the coding sequence of the hAIPL1 gene was amplified from human retina cDNA (BioChain, Hayward, Calif.) using the primers hAIPL1-NotI-forward (5'-ATATGCGGCCGCCATGGATGCCGCTCTGCTCCT-3') SEQ ID NO: 21 and hAIPL1-HindIII-reverse (5'-ACGCG-TAAGCTTTTATCAGTGCTGCAGCGAGTGCC-3') SEQ ID NO: 22 and cloned into the pAAV2.1-CMV-EGFP following digestion with Not I and Hind III.

AAV Virus Production

Recombinant AAV2/8 viruses were produced by the TIGEM AAV Injection Core according to protocols described elsewhere (26). For each viral preparation, physical titers [genome copies per milliliter (GC/ml)] were determined by PCR quantification using Taqman (27).

Animal Procedures

All studies on mice were conducted in strict accordance with the institutional guidelines for animal research and with the Association for Research in Vision and Ophthalmology (ARVO) Statement for the Use of Animal in Ophthalmic and Vision Research. All surgery was performed under anesthesia, and all efforts were made to minimize suffering.

Postnatal mice were anesthetized by hypothermia for 2 min at 4° C. and injected subretinally in the dorsal retinal areas with 1 µl of AAV vectors corresponding to $1 \times 10^9$ genome copies (GC). The same individual performed all the surgical procedures to minimize variability in the injection technique. Animals were sacrificed by cervical dislocation.

Adult mice (were anesthetized with an intraperitoneal injection of avertin (1.25% w/v of 2,2,2-tribromoethanol and 2.5% v/v of 2-methyl-2-Butanol; Sigma-Aldrich, St. Louis, Mo.) at 2 ml/100 g of body weight, and viral vectors were delivered via a trans-scleral transchoroidal approach, as previously described (28). Mice were injected in one eye with 1 ul of a mix comprised of 9:1 v/v AAV.CMV.premiR204/211 and AAV.CMV.EGF. The contralateral eye was injected with 1 ul of AAV.CMV.EGFP and served as control. Following injection (17-30 days later), the extent of transduction was assessed by ophthalmoscopy and eyes were harvested.

Laser Capture Microdissection

Frozen retinal sections on PEN-membrane slices were microdissected using an LMD 6500 microscope. Slices were fixed for 2 minutes in precold 75% Ethanol (EtOH) in DEPC water, then washed twice in DEPC water for 30 seconds and stained in Meyer's hematoxylin 7 µM for 1 minute. After the nuclei hematoxylin staining, the slices were washed twice in DEPC water for 30 seconds and dehydrated in EtOH 70%, EtOH 80%, EtOH 90%, twice EtOH 100% (30 seconds each) and dried on air for 15 minutes. The laser parameters used for the microdissection were: Power 60, Aperture 7, Speed 7, Specimen balance 46 and Offset 25.

miRNA Expression Analysis miRNA expression analysis in mice administered with the AAV.CMV.EGFP and AAV.CMV.premiR204/211 constructs was performed on samples from whole retinas and optic cups, respectively. Total RNA was extracted using the miRNeasy kit (Qiagen, Inc., Hilden, Germany) according to the manufacturer's instructions and quantified using the NanoDrop 1000 (Thermo Fischer Scientific, Waltham, Mass.). RNA quality was assessed by gel electrophoresis.

Quantitative (q) Reverse Transcriptase (RT-) PCR-based detection of mature miR-204, miR-124a and sno234 was performed using the TaqMan® microRNA assays (Applied Biosystems, Foster City, Calif.). All reactions were performed in triplicate. The qRT-PCR results, recorded as threshold cycle numbers (Ct), were normalized to the sno234 reference small RNA and the relative fold-change of expression was calculated using the $2^{-ddCT}$ method.

Electroretinography

For electrophysiological recordings, mice were dark-adapted for 3 hours, accommodated in a stereotaxic apparatus under dim red light, their pupils dilated with a drop of 1% tropicamide (Alcon Laboratories, Inc., Fort Worth, Tex.) and the body temperature maintained at 37.5° C. ERGs were evoked by 10-ms flashes of different light intensities ranging from $10^4$ to 20 cd·s/m$^2$ generated through a Ganzfeld stimulator (CSO, Florence, Italy). To minimize the noise, three different responses evoked by light were averaged for each luminance step (the time interval between light stimuli was 4-5 min). The electrophysiological signals were recorded with gold-plated electrodes inserted under the lower eyelids in contact with the cornea. Electrodes in each eye were referred to a needle electrode inserted subcutaneously at the level of the corresponding frontal region. The different electrodes were connected to a two-channel amplifier. Amplitudes of a- and b-waves were plotted as a function of increasing light intensities. After completion of responses obtained in dark-adapted conditions (scotopic) the recording session continued with the aim to dissect the cone pathway mediating the light response (photopic). To this end, the ERG in response to light of 20 $cd \cdot s/m^2$ was recorded in the presence of a continuous background light (background light set at 50 $cd/m^2$). For each group, the mean b-wave amplitude was plotted as a function of luminance (transfer curve) under scotopic and photopic conditions.

Histological Analysis

Mice were sacrificed, and their eyeballs were then harvested and fixed overnight by immersion in 4% paraformaldehyde (PFA). Before harvesting the eyeballs, the temporal aspect of the sclerae was marked by cautery in order to orient the eyes with respect to the injection site at the moment of the inclusion. The eyes were infiltrated with 30% sucrose for cryopreservation and embedded in tissue freezing medium (O.C.T. matrix, Kaltek, Padua, Italy) in pairs (i.e. left and right eye) to facilitate comparative analysis. For each eye, 150 to 200 serial sections (10 µm-thick) were cut along the horizontal plane and the sections were progressively distributed on 10 slides so that each slide contained 10 to 15 sections, each representative of the whole eye at different levels. The sections were stained with 4',6'-diamidino-2-phenylindole (Vectashield, Vector Lab Inc., Peterborough, UK) and EGFP was monitored with a Zeiss Axiocam (Carl Zeiss, Oberkochen, Germany) at different magnifications.

Immunofluorescence Staining

Frozen retinal sections were washed once with PBS and then fixed for 10 min in 4% PFA. Sections were then permeabilized either for 15 min in PBS containing 1% NP-40 (for anti-Rhodopsin, anti-cone arrestin, anti-Glutamine Synthetase) or in citrate buffer (for the anti-M- and S-Opsin). Blocking solution containing 10% normal goat serum (Sigma-Aldrich, St. Louis, Mo.) was applied for 1 hour. Primary antibodies were diluted in PBS and incubated overnight at 4° C. The secondary antibody (Alexa Fluor® 594, anti-rabbit or anti-mouse, 1:1000; Molecular Probes, Invitrogen, Carlsbad, Calif.) was incubated for 45 min. The primary antibodies used were anti-hCAR (29), Opn1mw (AB5405; Millipore), Opn1sw (AB5407; Millipore), Rhodopsin (Abcam) and anti-Glutamine Synthetase (MAB302; Millipore). Vectashield (Vector Lab Inc., Peterborough, UK) was used to visualize nuclei. Sections were photographed using Zeiss (LSM 710) Confocal microscopy.

TUNEL Assay

Apoptotic nuclei in frozen retinal sections were detected by the TdT-mediated dUTP terminal nick-end labeling kit according to the manufacturer's instructions (In Situ Cell Death Detection Kit, TMR red; Roche).

Results

Here, the authors propose to use two miRNAs, namely miR-204 and miR-211, to protect the retina from neuronal degeneration. In this study, the authors set to determine the effect that the delivery of miR-204/211 to retinal cells has on the progression of neurodegeneration.

Towards this goal, the authors decided to deliver the precursor forms of miR-204 (premiR-204) and of miR-211 (premiR-211) in the retina (namely in the subretinal space) of either wild-type mice or mouse models of retinal degeneration. In particular, the authors used the following injection scheme: each mouse analyzed was injected in one eye with an Adeno-associated viral (AAV) construct containing the precursor sequence of either miR-204 or of miR-211 (see Methods for details). The contralateral eye of each animal was injected, using the same strategy, with an AAV construct containing a reporter gene cassette (Enhanced Green Fluorescent Protein, EGFP) only and served as an experimental control. For these experiments, the authors decided to use the AAV serotype 2/8, which was previously shown to effectively transduce the mammalian retina, predominantly the retinal pigment epithelium and the photoreceptors (19). In order to drive the expression of either pre-miR-204/211 or EGFP in the injected retina, the authors initially used the constitutive cytomegalovirus (CMV) promoter.

Assessment of Proper miRNA Processing and Overexpression in Photoreceptors

Before carrying out the experiments in mouse models of photoreceptor degeneration, the authors first sought to determine whether the AAV-mediated delivery of the precursor sequences of miR-204 and miR-211 was followed by proper miRNA processing and formation of miR-204 and miR-211 mature forms in the transduced photoreceptor cells. Towards this goal, the authors injected three wild-type mice with the AAV.CMV.premiR204 viral construct in one eye and with the control AAV.CMV.EGFP construct in the contralateral eye. The authors then performed Laser Capture Microdissection (LCM) of all the injected eyes in order to specifically collect the outer nuclear layer, which contains photoreceptor cells (FIG. 1A). The authors extracted total RNA from the collected samples and measured the expression levels of the mature form of miR-204 by quantitative (q) Reverse Transcriptase (RT) PCR using the TaqMan microRNA assay kit. The authors found that the administration of the AAV.CMV.premiR204 vector conferred an 1.5 to 2-fold increase of mature miR-204 compared to the endogenous levels (FIG. 1B).

These results demonstrate that administration of the AAV.CMV.premiR204 vector induced an increase in the levels of properly processed miR-204. In order to exclude that the delivery and processing of the premiR-204 transgenes could interfere with the miRNA processing machinery in the retina, and therefore affect the physiological endogenous levels of other miRNAs, the authors also measured in injected eyes the expression of an unrelated miRNA, miR-124, which is abundantly expressed in the retina (16). The authors found that miR-124 expression levels were not significantly modified in the photoreceptors of injected eyes (FIG. 1B). Therefore, the authors conclude that the AAV-mediated delivery of premiR-204 leads to appropriate processing and increased expression levels of the mature forms of this miRNAs in photoreceptors and does not alter the proper processing and expression of other miRNAs expressed in the retina. Similar results were obtained with AAV-mediated delivery of premiR-211.

AAV-Mediated Delivery of miR-204/211 Leads to Amelioration of Retinal Morphology and Function in Mouse Models of Photoreceptor Degeneration To assess the beneficial effect of miR-204/211 in IRDs, the authors used the following two mouse models:

1) a model for an autosomal recessive form of IRD caused by a homozygous null mutation in the Aryl hydrocarbon interacting protein like 1 (Aipl1) gene (Aipl1 knockout mice) (20). Mutations in the AIPL1 gene are responsible for a severe form of LCA in humans. In Aipl1$^{-/-}$ mice the retina develops normally until postnatal day (P) 12. After this stage, rod and cone photoreceptors start to quickly degenerate leading to disorganization, fragmentation and notable size reduction of the photoreceptor outer segments and of the thickness of the ONL. The loss both of rod and cone function, due to the impaired phototransduction and the undergoing degeneration, is reflected by a complete absence of electroretinogram (ERG) in Aipl1$^{-/-}$ mice (20, 21).

2) a model for an autosomal dominant form of IRD (P347S Rhodopsin transgenic mouse). This transgenic mouse line carries a copy of the human Rhodopsin gene harboring a proline-to-serine substitution in position 347 of the protein. This mutation is responsible for a form of RP in human patients. The retinal phenotype in this mouse model is less severe compared to Aipl1$^{-/-}$ mice and an ERG response, although severely impaired, can be obtained up to 2-3 months of postnatal life (22).

The authors found that delivery of the premiR-204 transgene leads to a notable preservation of retinal structure in the injected eyes of the Aipl1$^{-/-}$ and Rhodopsin P347S models, as compared to the EGFP-injected contralateral eyes.

In particular, the authors obtained the following results:
a) Aipl1$^{-/-}$ Model.

The authors injected Aipl1$^{-/-}$ mice at postnatal day (P) 4 using the above-described scheme and sacrificed the mice at P21. At this stage, only a single row of photoreceptor nuclei is present in EGFP-injected eyes (FIG. 2A). In contrast, the authors observed a significant increase in the number of preserved rows as well as in the density of photoreceptor nuclei in the contralateral eyes of the above animals, which were injected with the AAV.CMV.premiR204 construct (FIG. 2B-C). These results clearly demonstrate a slower progression of retinal degeneration in miR-204 injected eyes. Moreover, the authors observed an increased staining for both rod (rhodopsin) and cone photoreceptor (cone arrestin and M-opsin) markers in the ONL of eyes injected with the AAV.CMV.premiR204 vector compared to the contralateral eyes injected with the control vector, as assessed by immunofluorescence analysis (FIGS. 3 and 4). Finally, the cone structure and outer segments were better preserved in the eyes injected with miR-204 vector, compared to the contralateral ones, as shown by immunolabelling with cone arrestin (FIGS. 3C and 3D). Similar results were obtained with AAV-mediated delivery of premiR-211.

In order to assess whether the protective effect that miR-204/211 conferred to the retina can be exploited in combination with gene replacement approaches, the authors carried out the injection procedure described above (i.e. subretinal injection at P4) in Aipl1$^{-/-}$ mice combining the AAV.CMV.premiR204 vector with an AAV vector driving expression of the humanAIPL1 cDNA under the control of CMV. This strategy would enable us to evaluate whether the combination of retinal neuroprotection (conferred by the delivery of miR-204/211) and replacement of the Aipl1 gene (humanAIPL1) deficiency could have a synergistic therapeutic effect. As shown in FIG. 5, retinal histological analysis at P30 demonstrated that combination of both miR-204 and humanAIPL1 preserved retinal thickness more efficiently compared to the contralateral eye injected with the humanAIPL1 alone. These preliminary data suggest that the combination of both miR-204 injection and humanAIPL1 gene delivery can yield additive therapeutic effects, i.e. slowing down of the progression of retinal degeneration (miR-204 effect) and enhancing potential restoration of AIPL1 activity (humanAIPL1 gene supplementation).

Similar results were obtained with AAV-mediated delivery of premiR-211.

b) Rhodopsin P347S Mouse Model.

The authors injected P347S transgenic mice at P4 following the same procedure described above for the Aipl1$^{-/-}$ mouse and sacrificed the animals at two different time points, i.e., P30 and P60. First, the authors detected at P30 a notable improvement of the ERG response in the miR-204-injected eyes of P347S mice, compared to the contralateral EGFP-injected eyes (FIG. 6). The authors found that this improvement was persistent also at P60, i.e., two months after the injection (FIG. 7). At both stages (i.e. P30 and P60), the enhanced ERG response was prevalent under photopic conditions that reflect cone activity, indicating that cone photoreceptors represented the main target of the beneficial effect provided by the miR-204 injection. In agreement with the above finding, immunofluorescence analysis revealed a significant preservation in the expression of cone photoreceptor markers, such as Opn1mw (M-Opsin) and Opn1sw (S-Opsin) proteins, in miR-204 injected eyes as opposed to EGFP-injected eyes (FIG. 8).

In further support of the above results, the authors also found that the injection of the premiR-204 AAV constructs determined a statistically significant decrease in the number of apoptotic cells in the photoreceptor layer compared to EGFP-injected eyes, as revealed by TUNEL staining (FIG. 9). Moreover, the authors determined that miR-204 injection led to a dramatic reduction of retinal gliosis, which represents a physiological response to photoreceptor damage, as assessed by immunofluorescence staining with the anti-Glutamine Synthetase (anti-GS6) antibody (FIG. 10).

The authors expanded these observations by increasing the number of murine retinas analyzed and further confirmed the results (FIG. 16).

Taken together, these findings strongly suggest that the subretinal delivery of the miR-204/211 vectors slows down the retinal degeneration in P347S and preserves retinal function, particularly in both scotopic and photopic conditions.

All the above-described injection experiments were carried out using an AAV construct containing the CMV constitutive promoter, which drives transgene expression in all transduced cells. To verify whether the restricted expression of miR-204/211 in photoreceptors was sufficient to ensure the beneficial effect of these two miRNAs in IRD models, the authors generated an AAV construct in which expression of the miR-204 precursor is under the control of the Rhodopsin promoter that drives transgene expression specifically in photoreceptors (Allocca et al, J of Virology, 2007 and Mussolino et al, Gene Therapy 2011). The authors then injected a group of P347S transgenic mice with this construct (AAV.RHO.premiR204) at P4 following the same strategy used for the AAV.CMV.premiR204 construct. The authors obtained a notable improvement of the ERG response in the RHO.miR204 injected eyes compared to the contralateral EGFP-injected controls at P30 (FIG. 11). The authors expanded these observations by increasing the number of murine retinas analyzed and further confirmed the results (FIG. 17). Similar to what shown for use of the CMV promoter (FIG. 14), also the injection of the RHO.miR204 construct did not lead to any significant alteration of the amplitude of 'b' waves in the retinas of miR-204/211 injected eyes compared to contralateral EGFP-injected controls eyes of wild type mice (FIG. 17). The above data clearly demonstrate that the restricted expression of miR- 204 transgenes in photoreceptors is sufficient to ensure the protective role of these two miRNAs in IRD conditions in vivo.

It is important to point out that all the previously described experiments have also been performed with either the premiR-204 or the premiR-211 sequences whose injection produced very similar results in all the models analyzed (see example in FIGS. 12 and 13). Therefore, the authors conclude that they both exert the same beneficial effect in IRD conditions in vivo. All of the above data demonstrate that the injection of miR-204/211 in the retina (and particularly in photoreceptors) of in vivo models of IRDs exerts a protective effect on photoreceptors, particularly on cones, by enhancing their survival. This is particularly surprising when considering the fact that miR-204/211 are not detectable in photoreceptor cells (FIG. 18).

Figure 19:
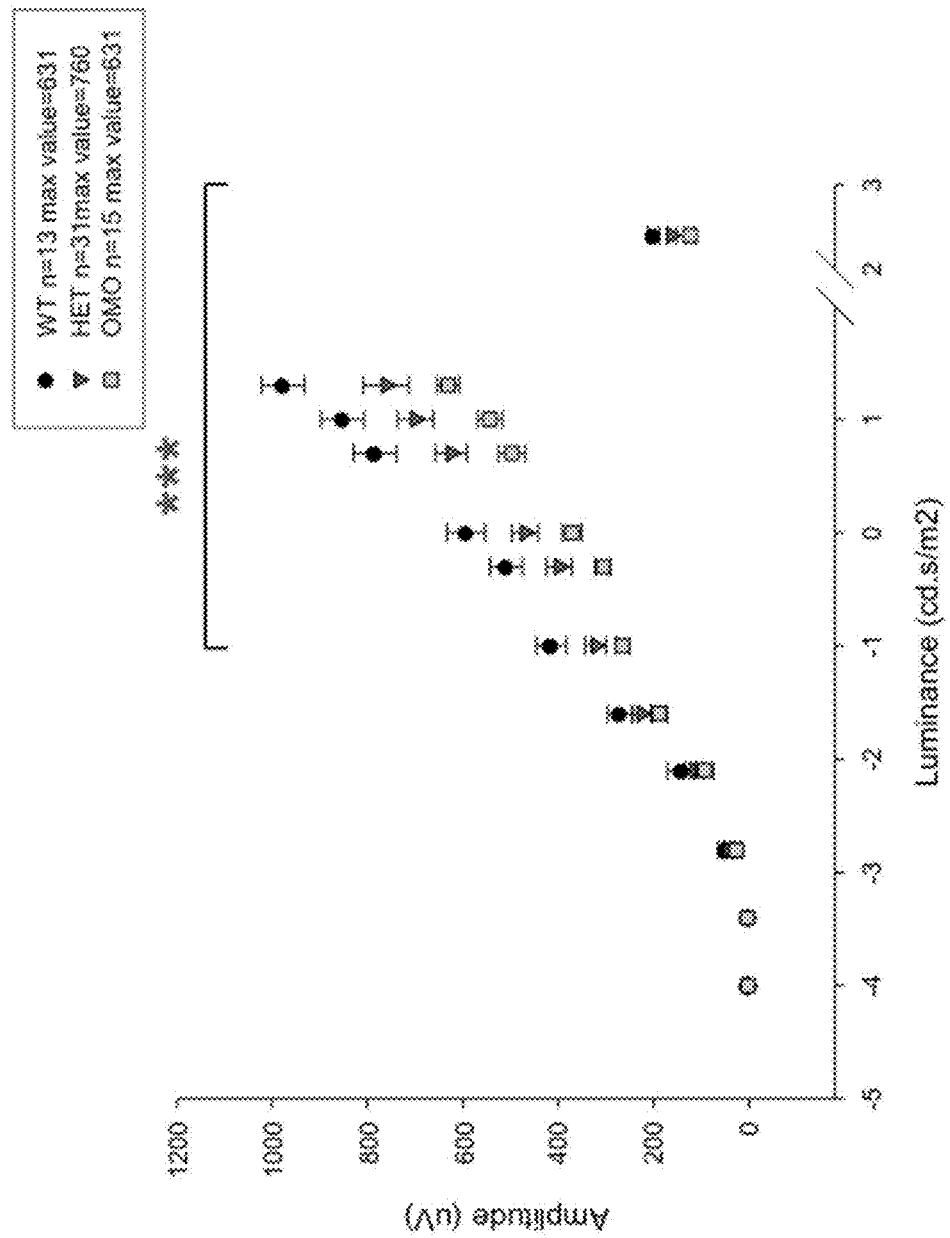

The strong effect of miR-204/211 on photoreceptors is further strengthened by the evidence that in the retina of a mouse knockout for miR-211, that the authors are currently characterizing, a significant deficit of photoreceptor function was observed (FIG. 19).

Safety Assessment of miR-204/miR-211 Delivery to the Retina of Wild-Type Mice

To assess safety of miR-204/211 delivery on retinal physiology, the authors carried out subretinal AAV-mediated delivery of miR-204 in a large cohort of adult C56BL/6 mice using the same scheme described above. As shown in FIG. 14, electroretinographic (ERG) analysis demonstrated that the 'b' waves were unaltered in miR-204 injected eyes compared to contralateral EGFP-injected controls eyes one month after the injection. Moreover, the authors carried out a similar analysis in wild-type mice injected at P4 and the authors performed ERG analysis at P30. Also in this case, the authors could not detect any significant alteration of the amplitude of 'b' waves in the retinas of miR-204 injected eyes compared to contralateral EGFP-injected controls eyes (FIG. 15). Similar results were obtained with AAV-mediated delivery of premiR-211.

These data support the safety of miR-204/211 delivery to healthy retinas.

The authors propose that the intraretinal administration of miR-204/211, particularly in photoreceptor cells, exerts a beneficial effect in photoreceptor degeneration, and particularly in IRDs, including retinitis pigmentosa (both isolated and syndromic forms), Leber congenital amaurosis, cone-rod dystrophies and cone dystrophies. Notably, this demonstrates a therapeutic effect obtained by the administration of individual miRNAs in photoreceptors in vivo.

In the present invention, the authors demonstrate that miR-204/211 have a protective effect in the process of photoreceptor degeneration and death, which are the primary conditions that underlie inherited retinal dystrophies. In such diseases, abnormal RPE differentiation and proliferation do not play key pathogenic roles.

BIBLIOGRAPHIC REFERENCES

1. J. Couzin, *Science* 319, 1782 (Mar. 28, 2008).
2. N. Meola, V. A. Gennarino, S. Banfi, *Pathogenetics* 2, 7 (2009).
3. R. Garzon, G. Marcucci, C. M. Croce, *Nat Rev Drug Discov* 9, 775 (October, 2010).
4. J. Kota et al., *Cell* 137, 1005 (Jun. 12, 2009).
5. A. Care et al., *Nat. Med.* 13, 613 (May, 2007).
6. T. Thum et al., *Nature* 456, 980 (Dec. 18, 2008).
7. D. Cacchiarelli et al., *EMBO Rep* 12, 136 (Feb. 1, 2011).
8. J. Elmen et al., *Nature* 452, 896 (Apr. 17, 2008).
9. R. E. Lanford et al., *Science* 327, 198 (Jan. 8, 2010).
10. A. G. Seto, Int. *J. Biochem. Cell Biol.* 42, 1298 (August, 2010).
11. E. L. Berson, *Invest Ophtalmol Vis Sci* 34, 1659 (1993).
12. F. P. Cremers, et al., *Hum. Mol. Genet.* 11, 1169 (May 15, 2002).
13. C. P. Hamel, *Orphanet J Rare Dis* 2, 7 (2007).
14. M. Michaelides, et al. *Surv. Ophthalmol.* 51, 232 (May-June, 2006).
15. M. Karali et al., *BMC Genomics* 11, 715 (2010).
16. M. Karali, et al., *Invest. Ophthalmol. Vis. Sci.* 48, 509 (February, 2007).
17. I. Conte et al., *Proc. Natl. Acad. Sci. U.S.A* 107, 15491 (Aug. 31, 2010).
18. B. P. Lewis, C. B. Burge, D. P. Bartel, *Cell* 120, 15 (Jan. 14, 2005).
19. C. Mussolino et al., *Gene Ther.* 18, 637 (July, 2011).
20. V. Ramamurthy, et al. *Proc. Natl. Acad. Sci. U.S.A* 101, 13897 (Sep. 21, 2004).
21. X. Liu et al., *Proc. Natl. Acad. Sci. U.S.A* 101, 13903 (Sep. 21, 2004).
22. T. Li, et al., *Proc. Natl. Acad. Sci. U.S.A* 93, 14176 (Nov. 26, 1996).
23. F. E. Wang et al., *FASEB journal* 24, 1552 (May, 2010).
24. S. Wang, K. M. Koster, Y. He, Q. Zhou, *Future Med Chem* 4, 277 (March, 2012).
25. M. Allocca et al., *J. Virol.* 81, 11372 (October, 2007).
26. M. Hildinger et al., *J. Virol.* 75, 6199 (July, 2001).
27. G. Gao et al., *Hum. Gene Ther.* 11, 2079 (Oct. 10, 2000).
28. F. Q. Liang, V. Anand, A. M. Maguire, J. Bennett, in *Methods in Molecular Medicine*, P. E. Rakoczy, Ed. (Humana Press Inc., 2000), vol. 47, pp. 125-39.
29. A. Li, X. Zhu, C. M. Craft, *Invest. Ophthalmol. Vis. Sci.* 43, 1375 (May, 2002).
30. Graham, F. L. and van der Eb, A. J., Virology 52:456-467, 1973.
31. McCutchan, J. H. and Pagano, J. S., Natl. Cancer Inst. 41:351-357, 1968.
32. Chu G, Hayakawa H, Berg P Nucleic Acids Research 15 (3): 1311-1326, 1987.
33. Fraley, R. et al., (1980), J. Biol. Chem. 255, 10431.
34. Capecchi, M. R. (1980). Cell 22: 479-488.
35. Felgner, P. L., et al., Proc. Natl. Acad. Sci. USA, Vol. 84, pp. 7413-7417, 1987.
36. Acheampong A A et al, 2002, Drug Metabol. and Disposition 30: 421-429.
37. Bennett J, Pakola S, Zeng Y, Maguire A M. Hum Gene Ther. 1996; 7:1763-1769.
38. Ambatia, J., and Adamis, A. P., Progress in Retinal and Eye Res. 2002; 21: 145-151.
39. Cheng Y, Ji R, Yue J, et al. Am J Pathol 2007; 170: 1831-1840.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10369231B2). An electronic copy of the "Sequence Listing" will also be available from the USPTO upon request and payment of the fee set forth in 37 CFR 1.19(b)(3).

The invention claimed is:

1. A method for treating and/or preventing an inherited retinal dystrophy disease or disorder in a subject, the method comprising administering to the subject a member selected from the group consisting of:
   a) an agent selected from the group consisting of an miRNA, an miRNA precursor, a mature miRNA, an miRNA mimetic or a mixture of miRNA mimetics, an RNA or DNA molecule encoding for said miRNA, for said miRNA precursor, for said mature miRNA, for said miRNA mimetic or mixture of miRNA mimetics, and combinations thereof,
   b) a pharmaceutical composition containing said agent of a) and pharmaceutically acceptable excipients and/or diluents,
   c) a recombinant expression vector comprising a coding sequence for the agent of a), under the control of a suitable promoter,
   d) a host cell transformed by the recombinant expression vector of c) comprising a coding sequence for the agent, and
   e) combinations of a) through d);
   wherein the agent of a) comprises the seed sequence UUCCCUU or encodes a nucleotide sequence comprising a seed sequence UUCCCUU; and
   wherein the inherited retinal dystrophy disease or disorder is retinitis pigmentosa, Leber congenital amaurosis, a cone-rod dystrophy, or a cone dystrophy.

2. The method according to claim 1, wherein said agent of a) comprises the mature sequence of miR-204 or the mature sequence of miR-211.

3. The method according to claim 1, wherein said agent is provided by a delivery vehicle.

4. The method according to claim 1, wherein the inherited retinal dystrophy disease or disorder is Retinitis Pigmentosa.

5. The method according to claim 1, wherein the suitable promoter is the Rhodopsin promoter sequence.

6. The method according to claim 1, wherein the recombinant expression vector of d) further comprises one or more sequences coding for a wild type version of a sequence responsible for the inherited retinal dystrophy, under the control of a suitable promoter.

7. The method according to claim 6, wherein the one or more wild-type version of the coding sequence responsible for the retinal dystrophy is selected from the group consisting of: SEQ ID NO: 23 through SEQ ID NO: 414.

8. The method according to claim 1, wherein the recombinant expression vector of d) is an adeno-associated virus (AAV) derivative.

9. The method according to claim 1, wherein the nucleic acid sequence or the recombinant expression vector or the host cell is administered as part of a pharmaceutical composition containing pharmaceutically acceptable excipients and/or diluents for use in the treatment and/or prevention of a retinal dystrophy.

10. The method according to claim 6, wherein the sequences coding for a wild type version of a sequence responsible for the inherited retinal dystrophy are inserted in a recombinant expression vector that is separate from the recombinant expression vector of d).

11. The method according to 26, wherein said agent is delivered via intraocular administration to said subject.

12. The method according to claim 3, wherein the delivery vehicle is selected from the group consisting of viral vectors, microspheres, liposomes, colloidal gold particles, lipopolysaccharides, polypeptides, polysaccharides, and pegylated viral vehicles.

13. The method according to claim 3, wherein the delivery vehicle is an adeno-associated virus (AAV) derivative.

14. The method according to claim 1, wherein the agent of a) protects the retina from the inherited retinal dystrophy disease or disorder.

15. The method according to claim 1, wherein the agent of a) treats the retina for the inherited retinal dystrophy disease or disorder.

* * * * *